(12) United States Patent
MacDermott et al.

(10) Patent No.: US 10,702,454 B2
(45) Date of Patent: Jul. 7, 2020

(54) SOLID COSMETIC COMPOSITION IN PRESSED POWDER FORM

(71) Applicant: L'OREAL, Paris (FR)

(72) Inventors: Padraig MacDermott, Meudon (FR); Catherine Sautel, L'Hay-les-Roses (FR); Gwenola Le Gars, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/647,010

(22) PCT Filed: Dec. 2, 2013

(86) PCT No.: PCT/EP2013/075235
§ 371 (c)(1),
(2) Date: May 22, 2015

(87) PCT Pub. No.: WO2014/086710
PCT Pub. Date: Jun. 12, 2014

(65) Prior Publication Data
US 2015/0305988 A1    Oct. 29, 2015

Related U.S. Application Data

(60) Provisional application No. 61/763,046, filed on Feb. 11, 2013.

(30) Foreign Application Priority Data

Dec. 4, 2012 (FR) ...................... 12 61630

(51) Int. Cl.
| | |
|---|---|
| *A61K 8/02* | (2006.01) |
| *A61K 8/25* | (2006.01) |
| *A61K 8/26* | (2006.01) |
| *A61K 8/37* | (2006.01) |
| *A61K 8/58* | (2006.01) |
| *A61K 8/81* | (2006.01) |
| *A61K 8/88* | (2006.01) |
| *A61K 8/891* | (2006.01) |
| *A61K 8/96* | (2006.01) |
| *A61Q 1/02* | (2006.01) |
| *A61Q 1/08* | (2006.01) |
| *A61Q 1/10* | (2006.01) |
| *A61Q 1/12* | (2006.01) |

(52) U.S. Cl.
CPC ............. *A61K 8/022* (2013.01); *A61K 8/025* (2013.01); *A61K 8/0254* (2013.01); *A61K 8/25* (2013.01); *A61K 8/26* (2013.01); *A61K 8/37* (2013.01); *A61K 8/585* (2013.01); *A61K 8/8117* (2013.01); *A61K 8/8147* (2013.01); *A61K 8/8152* (2013.01); *A61K 8/88* (2013.01); *A61K 8/891* (2013.01); *A61K 8/965* (2013.01); *A61Q 1/02* (2013.01); *A61Q 1/08* (2013.01); *A61Q 1/10* (2013.01); *A61Q 1/12* (2013.01); *A61K 2800/43* (2013.01)

(58) Field of Classification Search
None
See application file for complete search history.

(56) References Cited

U.S. PATENT DOCUMENTS

| | | |
|---|---|---|
| 2012/0164091 A1 | 6/2012 | Cruz et al. |
| 2013/0295148 A1 | 11/2013 | Claude-Foly et al. |
| 2013/0323192 A1 | 12/2013 | Nakamura |
| 2015/0320647 A1 | 11/2015 | Shirai et al. |

FOREIGN PATENT DOCUMENTS

| | | | | |
|---|---|---|---|---|
| JP | 56-108703 | * | 8/1981 | ............... A61K 8/00 |
| JP | S56-108703 | | 8/1981 | |
| JP | S61-54766 B2 | * | 11/1986 | ............... A61K 7/02 |
| JP | 2000-191424 | | 7/2000 | |
| JP | 2000-302625 | | 10/2000 | |
| JP | 2012-184211 | | 9/2012 | |
| JP | 2012-214420 | | 11/2012 | |
| WO | 2012 066457 | | 5/2012 | |
| WO | 2012/066457 | | 5/2012 | |

OTHER PUBLICATIONS

English Abstract, JP 56-108703 (1981).*
Machine translation, JP S61-54766 B2 (Year: 1986).*
International Search Report dated Nov. 19, 2014 in PCT/EP2013/075235 Filed Dec. 2, 2013.
Office Acton as received in the corresponding European Patent Application No. 13 799 522.1-1114 dated Jun. 12, 2018.
Office Action as received in the corresponding Japanese patent application No. 2015-545759 dated Nov. 6, 2017.

* cited by examiner

*Primary Examiner* — Bethany P Barham
*Assistant Examiner* — Barbara S Frazier
(74) *Attorney, Agent, or Firm* — Oblon, McClelland, Maier & Neustadt, L.L.P.

(57) ABSTRACT

The present invention relates to a solid cosmetic composition in the form of a preferably pressed powder, comprising, in a physiologically acceptable medium, at least: —an oily phase greater than or equal to 20% by weight relative to the total weight of the composition, —a pulverulent phase greater than or equal to 40% by weight relative to the total weight of the composition, comprising at least one spherical filler and at least one lamellar filler, the spherical filler(s) and the lamellar filler(s) being present in a respective total weight content such that the weight ratio of the spherical filler(s) to the lamellar filler(s) is greater than or equal to 0.01 and preferably between 0.02 and 15. The present invention also relates to a product obtained by means of a particular process, to a process for manufacturing a cosmetic composition, and to a process for coating the face with said cosmetic composition.

15 Claims, No Drawings

SOLID COSMETIC COMPOSITION IN PRESSED POWDER FORM

The present invention targets the field of solid cosmetic care and/or makeup compositions, and more specifically compositions in pressed powder form. It also relates to a process for coating the skin, in particular of the face, with said cosmetic composition.

The galenical forms conventionally adopted for solid compositions are generally loose or compact powders. As non-limiting illustrations of the solid galenical forms more particularly considered in the field of makeup, mention may be made in particular of loose or compact powders such as foundation powders, face powders or eyeshadows.

The main function of the abovementioned powders is to provide colour and matting or else to confer coverage.

Generally, loose powders comprise exclusively particles. However, in some cases, 2% or 3% by weight of fatty phase relative to the total weight of the composition may be envisaged in order to serve as a binder for said particles.

Generally, compact powders combine a largely predominant pulverulent phase with a binding fatty phase, which is at least partly liquid, these two phases both being present according to a respective total content such that the weight ratio of the pulverulent phase to the fatty phase is generally approximately 90/10.

A pulverulent phase is made up essentially of fillers combined with colouring agents, the amount of these colouring agents being modified to afford the desired colour, masking or matting makeup effect.

To obtain a composition in solid form of the 90/10 type, it is known from the prior art to use compacted makeup powders made up of a mixture of powders with the fatty phase, which are formed by compacting (at more than one hundred bar). This compacting is generally carried out during a process described as a dry process, consisting in mixing together the pulverulent phase and the fatty phase and in compacting under high pressure the composition resulting therefrom, in a case.

However, it is possible, to a minor extent, to carry out a process described as a wet process in order to prepare such compositions. In this type of process, the pulverulent phase and the fatty phase of said composition are brought into contact with a volatile solvent so as to produce a suspension which is subsequently pressed to give a compact solid pulverulent composition, the volatile solvent being removed from the composition.

Thus, the amount of fatty phase, and in particular of oily phase, in such compositions obtained by dry process or wet process generally does not exceed 10% by weight relative to the total weight of the composition, so as to obtain good compacting of the powder via mechanical means, and also to avoid any overspill of the composition out of the case.

For these reasons, these formulation routes quite often mean that formulaters have to limit the amount of fatty phase, and in particular of oil(s), in order to provide good compacting of the powder.

Furthermore, such solid compositions with a high content of pulverulent phase may have the drawback of being too compacting, difficult to disintegrate, uncomfortable, too dry and too powdery and, for some, of being fragile and brittle, with poor impact resistance.

Likewise, such powders with a high content of pulverulent phase may have the drawback of not being very sensory (i.e. not very pleasant to the touch, not disintegrating well, not very comfortable on application, too powdery when taken up and when applied, too granular and/or with uneven deposition on application).

A subsequent problem is that it is difficult to obtain a good wear property of the composition, unless the constituents of the pulverulent phase, predominantly present in such a composition, are adjusted.

To do this, another solution would consist in increasing the amount of fatty phase, and in particular of oil(s), but this composition, in addition to the abovementioned drawbacks associated with the manufacturing processes, may have a tendency to become waxy, i.e. to harden during use, until it can no longer be taken up.

There is therefore a need to develop makeup compositions which are not very brittle and which have good impact resistance.

An aim of the present invention is also to obtain makeup compositions which exhibit good cohesion and good homogenization, while at the same time offering satisfactory cosmetic qualities.

An aim of the present invention is also to obtain makeup compositions which do not become waxy over time.

An aim of the present invention is also to obtain makeup compositions which do not crack over time.

An aim of the present invention is also to obtain makeup compositions which exhibit good disintegration (in terms of amount of product taken up to be applied).

An aim of the present invention is also to obtain makeup compositions which have an appropriate hardness.

An aim of the present invention is also to obtain makeup compositions which have a silky feel which is pleasant when they are taken up, optionally reducing the powdery effect.

An aim of the present invention is also to obtain makeup compositions which are pleasant to wear (without any effect of skin dryness or tautness).

An aim of the present invention is also to obtain makeup compositions which confer a fresh effect on application.

An aim of the present invention is also to obtain makeup compositions which thus allow a makeup result that is smooth, uniform, and/or without any overthickness or any material effect.

An aim of the present invention is also to obtain makeup compositions which exhibit good adhesion to the keratin material to be made up, in particular the skin of the face, in particular good wear property over time (for example 8 to 24 hours) and with respect to water and/or rubbing.

To do this, according to a first aspect, a subject of the present invention is a solid cosmetic makeup and/or care composition in the form of a preferably pressed powder, comprising, in a physiologically acceptable medium, at least:
  an oily phase greater than or equal to 20% by weight relative to the total weight of the composition,
  a pulverulent phase greater than or equal to 40% by weight relative to the total weight of the composition, comprising at least one spherical filler and at least one lamellar filler,
the spherical filler(s) and the lamellar filler(s) being present in a respective total weight content such that the weight ratio of the spherical filler(s) to the lamellar filler(s) is greater than or equal to 0.01 and preferably between 0.02 and 15.

According to one preferred embodiment, the composition can be obtained, and preferably is obtained, by means of a process in which the oily phase, optionally one or more hydrophobic film-forming polymer(s), the pulverulent phase, and at least one additional volatile solvent are mixed together to produce a suspension, said suspension resulting therefrom being subsequently formed by pressing, preferably accompanied by a suctioning step.

The oily phase and the hydrophobic film-forming polymer(s) form a fatty phase which is preferably liquid (in particular at 25° C. and at atmospheric pressure).

Such a composition preferably obtained by pressing by means of the process described above is obtained by subjecting the powder to a low pressure of a few bar to a few tens of bar, example from 2 to 100 bar, better still from 2 to 50 bar, even better still from 2 to 30 bar, more preferentially from 2 to 10 bar, for example from 2 to 5 bar.

Such a composition, preferably obtained by means of the process described above, makes it possible to obtain a composition with advantageous sensory properties.

Furthermore, despite an optional high content of spherical filler(s), this composition exhibits good impact resistance.

Furthermore, despite an optional presence of nacres, this composition can exhibit good impact resistance by adjusting the fatty phase.

Such a composition makes it possible to obtain a texture which is pleasant to the touch, when taken up and when applied.

The texture of such a composition allows the deposition on the skin of a smooth, uniform film, which has good wear properties.

The weight ratio of the spherical filler(s) to the lamellar filler(s) in said composition allows good cosmeticity of said composition obtained and resolves at least any one of the abovementioned technical problems, in particular the disintegration, the comfort to the touch, upon application and while wearing it, the texture and the makeup result.

This composition having a considerable liquid fatty phase which forms a binder for the pulverulent phase makes it possible not only to adjust the fillers, but also to adjust the fatty, or hydrophobic, compounds in order to solve any one of the abovementioned technical problems, in particular for the wear property, the fresh effect, the comfort to the touch, upon application and while wearing it, and the texture.

For the purposes of the present invention, the following definitions apply:
  the term "solid" is intended to denote the state of the composition at ambient temperature (25° C.) and at atmospheric pressure (760 mmHg), i.e. a composition of high consistency, which conserves its form during storage. In contrast to "fluid" compositions, it does not flow under its own weight. It is advantageously characterized by a hardness as defined hereinafter;
  the term "pressed powder" is intended to denote a mass of product, the cohesion of which is at least partly provided by virtue of a pressing during manufacture. In particular, by carrying out a measurement using a TA.XT.plus Texture Analyser sold by the company Stable Micro Systems, the pressed powder according to the invention can advantageously exhibit a resistance to pressure of between 0.1 and 1 kg and in particular between 0.2 and 0.8 kg, with respect to the surface area of the spindle used (in the case in point, 7.07 mm$^2$). The measurement of this resistance is performed by moving an SMS P/3 flat-headed cylindrical spindle in contact with the powder, over a distance of 2 mm and at a speed of 0.5 mm/second;
  the term "physiologically acceptable medium" is intended to denote a medium that is particularly suitable for the application of a composition according to the invention to the skin;
  the term "filler" and by extension the term "spherical filler" or "lamellar filler" should be understood throughout the text as "distinct from a colouring agent".

Preferably, the composition according to the invention comprises less than 3% by weight and preferably less than 2% by weight of water relative to the total weight of the composition, or even is free of water.

The composition according to the invention advantageously comprises a solids content of greater than or equal to 90%, better still greater than or equal to 95%, even greater than or equal to 98%, or even equal to 100%.

For the purposes of the present invention, the "solids content" denotes the content of non-volatile matter.

The solids content (abbreviated to SC) of a composition according to the invention is measured using a Halogen Moisture Analyzer HG 53 commercial halogen drying device from Mettler Toledo. The measurement is carried out on the basis of the weight loss of a sample dried by halogen heating and thus represents the percentage of residual matter once the water and the volatile matter have evaporated.

This technique is fully described in the documentation of the device supplied by Mettler Toledo.

The measurement protocol is as follows:

Approximately 2 g of the composition, hereinafter the sample, are spread out over a metal dish, which is introduced into the abovementioned halogen drying device. The sample is then subjected to a temperature of 105° C. until an unchanging weight is obtained. The wet weight of the sample, corresponding to its initial weight, and the dry weight of the sample, corresponding to its weight after halogen heating, are measured using a precision balance.

The experimental error associated with the measurement is of the order of plus or minus 2%.

The solids content is calculated in the following way:

Solids content(expressed as % by weight)=100×(dry weight/wet weight).

According to preferred embodiments corresponding to at least one of the abovementioned technical problems:
  the pulverulent phase is present in a content greater than or equal to 50% by weight, better still greater than or equal to 60% by weight, advantageously between 50% and 80% by weight, better still between 55% and 75% by weight, and even better still between 58% and 70% by weight, relative to the total weight of the composition;
  the spherical filler(s) is (are) chosen from:
    silica powders;
    powders of acrylic (co)polymers, and derivatives thereof, in particular powders of acrylate (co)polymer, and derivatives thereof;
    polyurethane powders;
    silicone powders;
    polyamide powders;
    perlite powders;
    and mixture(s) thereof, preferably from powders of acrylic (co)polymers, and derivatives thereof, in particular powders of acrylate (co)polymer, and derivatives thereof, silicone powders, polyamide powders, and mixture(s) thereof;
  the pulverulent phase also comprises at least one colouring agent chosen from nacres, pigments, reflective particles, and mixtures thereof, preferably from pigments, more preferentially from inorganic pigments, and even more preferentially from metal oxides;

the pulverulent phase comprises a plurality of spherical fillers and a plurality of lamellar fillers;

the spherical filler(s) is (are) present in a total content greater than or equal to 1% by weight, relative to the total weight of the composition, for example between 5% and 70% by weight, preferably between 8% and 60% by weight, better still between 10% and 55% by weight and even better still between 15% and 50% by weight, relative to the total weight of the composition;

the lamellar filler(s) is (are) present in a total content greater than or equal to 1% by weight relative to the total weight of the composition, for example between 5% and 70% by weight, preferably between 10% and 60% by weight and better still between 20% and 55% by weight, relative to the total weight of the composition;

the spherical filler(s) and (i.e. plus) the lamellar filler(s) are present in a total content greater than or equal to 5% by weight, relative to the total weight of the composition, for example between 5% and 70% by weight, relative to the total weight of the composition, preferably between 10% and 60% by weight, better still between 20% and 58% by weight and even better still between 40% and 55% by weight, relative to the total weight of the composition;

the spherical filler(s) and the lamellar filler(s) plus the colouring agent(s) are present in a respective total weight content such that the weight ratio of the spherical filler(s) to the lamellar filler(s) plus the colouring agent(s) is greater than or equal to 0.01 and preferably between 0.02 and 5;

the pulverulent phase comprises at least one colouring agent, preferably at least one pigment, preferentially at least one organic pigment, in particular at least one metal oxide, the colouring agent(s) being present in a total content greater than or equal to 1% by weight, relative to the total weight of the composition, for example between 2% and 60% by weight, better still between 3% and 50% by weight and even better still between 5% and 30% by weight, relative to the total weight of the composition;

the filler(s) and at least one colouring agent are present in a respective total content such that the weight ratio of the filler(s) to the colouring agent(s) is between 0.5 and 5 and preferably between 1.5 and 2.5;

the oily phase, and preferably the non-volatile oil(s), is (are) present in a total content greater than or equal to 25% by weight, more preferably greater than or equal to 28% by weight, still more preferably greater or equal to 30% by weight, advantageously in a content of between 25% and 50% by weight and better still between 28% and 42% by weight, relative to the total weight of the composition;

said oily phase comprises at least one hydrocarbon-based oil, preferentially at least one non-volatile hydrocarbon-based oil, preferably chosen from at least one synthetic ester chosen from oils of formula $R_1COOR_2$ in which $R_1$ represents a residue of at least one linear or branched fatty acid comprising from 1 to 40 carbon atoms and $R_2$ represents a hydrocarbon-based chain that is in particular branched, containing from 1 to 40 carbon atoms, on condition that $R_1+R_2$ is greater than or equal to 10;

this non-volatile hydrocarbon-based oil preferably comprises at least one $C_{12}$-$C_{15}$ alkyl benzoate;

the preferentially non-volatile, hydrocarbon-based oil(s), preferably the at least one $C_{12}$-$C_{15}$ alkyl benzoate, is (are) present in a content ranging from 10% to 40% by weight, in particular from 15% to 35% by weight and better still from 20% to 30% by weight, relative to the total weight of the composition;

the oily phase comprises at least one silicone oil, preferentially at least one non-volatile silicone oil;

the oily phase comprises at least one silicone oil, preferably non-volatile silicone oil, preferentially chosen from linear or phenyl, preferably phenyl, non-volatile silicone oils, the total content of the silicone oil(s), preferably non-volatile silicone oil(s), preferably representing from 1% to 20% by weight, preferably from 2% to 15% by weight and better still from 4% to 13% by weight, relative to the total weight of the composition—said oily phase comprises at least one non-volatile oil, preferably chosen from non-volatile hydrocarbon-based oils, non-volatile silicone oils, and mixture(s) thereof, more preferentially comprises at least one non-volatile hydrocarbon-based oil and at least one non-volatile silicone oil;

the oily phase comprises at least one hydrocarbon-based oil, preferably non-volatile hydrocarbon-based oil, and at least one silicone oil, preferably non-volatile silicone oil, the hydrocarbon-based oil(s), preferably non-volatile hydrocarbon-based oil(s), and the silicone oil(s), preferably non-volatile silicone oil(s), preferably being present according to a respective total content such that the weight ratio of the hydrocarbon-based oil(s), preferably non-volatile hydrocarbon-based oil(s), to the silicone oil(s), preferably non-volatile silicone oil(s), is preferably greater than or equal to 1, preferably greater than or equal to 2, advantageously between 1.2 and 10, better still between 1.5 and 6, even better still between 1.6 and 3 and even more preferentially between 1.8 and 2.5;

the composition comprises at least one hydrophobic film-forming polymer chosen from homopolymers and copolymers of a compound comprising an ethylenic unit, acrylic polymers and copolymers, polyurethanes, polyesters, polyureas, cellulose-based polymers for instance nitrocellulose, silicone polymers such as silicone resins, silicone polyamides, polymers with a non-silicone organic backbone grafted with monomers containing a polysiloxane, polyamide polymers and copolymers, polyisoprenes, hydrocarbon-based block copolymers, which are preferably amorphous, formed by polymerization of an olefin, and mixture(s) thereof, preferably from hydrocarbon-based block copolymers, which are preferably amorphous, formed by polymerization of an olefin;

the composition comprises at least one hydrophobic film-forming polymer chosen from hydrocarbon-based block copolymers, which are preferably amorphous, formed by polymerization of an olefin, comprising at least one amorphous hydrocarbon-based block copolymer which comprises an amorphous block copolymer of styrene and of an olefin, more preferentially comprising at least one hydrocarbon-based block copolymer, which is preferably amorphous and preferably hydrogenated, comprising styrene blocks and ethylene/$C_3$-$C_4$ alkylene blocks;

the composition comprises at least one hydrophobic film-forming polymer chosen from hydrocarbon-based block copolymers, which are preferably amorphous, formed by polymerization of an olefin, chosen from a styrene-ethylene/butylene diblock copolymer, a styrene/ethylene-propylene diblock copolymer, a styrene-ethylene/isoprene diblock copolymer, a styrene-ethylene/propylene diblock copolymer, a styrene-ethylene/butylene-styrene triblock copolymer, and mixture(s) thereof, even more preferably from a styrene/ethylene-propylene diblock copolymer, a styrene-ethylene/butylene-styrene triblock copolymer, and mixture(s) thereof;

the hydrophobic film-forming polymer(s), preferably the hydrocarbon-based block copolymer(s), is (are) present in a (total) content greater than or equal to 0.1% by weight, in particular greater than or equal to 0.5% by weight relative to the total weight of the composition, preferably between 0.8% and 10% by weight relative to the total weight of the composition and better still between 1% and 8% by weight relative to the total weight of the composition;

the hydrophobic film-forming polymer(s), preferably the hydrocarbon-based block copolymer(s), and the oily phase are present in the composition in a respective total content such that the weight ratio of the hydrophobic film-forming polymer(s), and preferentially of the hydrocarbon-based block copolymer(s), to the oily phase is inclusively between 0.02 and 0.5 and better still between 0.05 and 0.2;

the hydrophobic film-forming polymer(s), preferably the hydrocarbon-based block copolymer(s), and the non-volatile hydrocarbon-based oils(s), preferably chosen from $C_{12}$-$C_{15}$ alkyl benzoate(s), are present in the composition in a respective total content such that the weight ratio of the hydrophobic film-forming polymer(s), and preferentially of the hydrocarbon-based block copolymer(s), to the non-volatile hydrocarbon-based oil(s), preferably the (said) $C_{12}$-$C_{15}$ alkyl benzoate(s), is inclusively between 0.01 and 0.3 and better still between 0.04 and 0.2;

the hydrophobic film-forming polymer(s), preferably the hydrocarbon-based block copolymer(s), and the non-volatile silicone oil(s) are present in the composition in a respective total content such that the weight ratio of the hydrophobic film-forming polymer(s), and preferentially of the hydrocarbon-based block copolymer(s), to the non-volatile silicone oil(s), is inclusively between 0.03 and 0.5 and better still between 0.1 and 0.3;

the composition is a face powder, preferably chosen from a blusher, a bronzer or a powder with a healthy appearance effect.

According to one particularly preferred embodiment, said solid cosmetic makeup and/or care composition that is in the form of a pressed powder comprises, in a physiologically acceptable medium, limits inclusive and expressed as weight of dry matter for each of the compounds considered, relative to the total weight of the composition, at least:

0.5% to 8% of hydrophobic film-forming polymer(s), preferably of hydrocarbon-based block copolymer(s), which are preferably amorphous, 20% to 40% of non-volatile hydrocarbon-based oil(s) alone or preferably as a mixture with at least one additional non-volatile silicone oil, 5% to 30% of colouring agent(s), preferably comprising 0.5% to 15% of pigments, in particular chosen from metal (poly)oxides, preferably iron oxides and/or titanium oxides, 45% to 60% of filler(s), preferably comprising 10% to 30% of spherical filler(s) and 20% to 45% of lamellar filler(s), and less than 5% of water, preferably 0% of water.

According to a second aspect of the invention, a subject of the present invention is also a process for coating, in particular making up and/or caring for, keratin materials, in particular the skin, preferably the face, in which a composition as defined previously is applied to said keratin materials, in particular to the skin, preferably to the face.

According to a third aspect of the invention, a subject of the present invention is also a process for manufacturing a composition for making up and/or caring for keratin materials, in particular the skin, preferably as defined previously, comprising the steps of:

mixing an oily phase present according to a content greater than or equal to 20% by weight, relative to the total weight of the composition, preferably at least one hydrophobic film-forming polymer, a pulverulent phase present according to a content greater than or equal to 40% by weight, and at least one additional volatile solvent, forming said composition by pressing, and at least partially, and preferably totally, removing the additional volatile solvent(s), preferably by suctioning.

According to one particular embodiment, the hydrophobic film-forming polymer(s) is (are) heated, preferentially during the mixing with the oily phase.

According to one particular embodiment, the liquid fatty phase (oily phase and optionally hydrophobic, film-forming polymer(s)) and the pulverulent phase are heated during the mixing thereof.

According to one particular embodiment, said suspension undergoes a suctioning step, preferably simultaneously with the forming step, so as to remove the additional volatile solvent(s).

According to one particular embodiment, said suspension which has been formed can undergo a heating step so as to accelerate the removal of the additional volatile solvent(s).

According to one particular embodiment, the pulverulent phase and the liquid fatty phase can be mixed in a first step, for example via an extruder, before, in a second step, adding the additional volatile solvent(s) to this mixture.

The additional volatile solvent(s) is (are) preferably a volatile oil, intended to be evaporated from the composition such that it is at least partially, and preferably totally, removed from the cosmetic composition in accordance with the invention.

The additional solvent(s) is (are) preferably a volatile hydrocarbon-based oil, such as a volatile isoparaffin oil.

It should be noted that all the characteristics mentioned for the cosmetic composition in accordance with the invention are also valid for a composition prepared using this particular process.

Pulverulent Phase

A solid composition according to the invention advantageously has a content of pulverulent phase greater than or equal to 50% by weight, better still greater than or equal to 60% by weight, relative to the total weight of the composition, advantageously between 50% and 80% by weight, better still between 55% and 75% by weight, and better still between 58% and 70% by weight, relative to the total weight of the composition.

The composition, and in particular the pulverulent phase, comprises at least one spherical filler and at least one lamellar filler, the spherical filler(s) and the lamellar filler(s) being present in a respective total weight content such that the weight ratio of the spherical filler(s) to the lamellar filler(s) is greater than or equal to 0.01, preferably between 0.02 and 15, advantageously between 0.1 and 10, more preferably between 0.35 and 5 and more preferably between 0.45 and 2.

The pulverulent phase also advantageously comprises at least one colouring agent.

Fillers

The term "fillers" should be understood to mean colourless or white solid particles of any shape, which are in a form that is insoluble and dispersed in the medium of the composition. Inorganic or organic in nature, they make it possible to confer softness, mattness and uniformity of makeup on the composition.

The fillers may or may not be surface-coated, and in particular they may be surface-treated with silicones, amino acids, fluoro derivatives or any other substance that promotes the dispersion and compatibility of the filler in the composition.

Such fillers are distinct from what is referred to in the following section as "colouring agents".

Spherical Fillers

The term "spherical fillers" should be understood to mean fillers comprising at least one rounded general portion, preferably defining at least one sphere portion, preferably defining on the inside a cavity or a hollow.

Such "spherical" fillers may be perfectly spherical fillers, globular fillers, hemi-spherical fillers, bowl-shaped fillers or else horseshoe-shaped fillers.

The spherical filler(s) is (are) preferably hollow, or more generally capable of absorbing and/or adsorbing at least partly the oily phase, and more generally the fatty phase.

The spherical filler(s) in accordance with the invention is (are) advantageously a sebum-absorbing particle or particles having a sebum uptake. The term "sebum-absorbing particle" is intended to mean a powder that is capable of absorbing and/or adsorbing sebum.

The sebum uptake corresponds to the amount of sebum absorbed and/or adsorbed by the particle. It is measured according to the wet point method as follows.

Method for Measuring Sebum Uptake of a Powder:

The sebum uptake of a powder is measured according to the method for determining oil uptake of powder described in standard NF T 30-022. It corresponds to the amount of sebum adsorbed onto the available surface of the powder, by measuring the wet point.

An amount m (in grams) of powder of between about 0.5 g and 5 g (the amount depends on the density of the powder) is placed on a glass plate and artificial sebum having the composition below is then added dropwise:

| | |
|---|---|
| triolein | 29% |
| oleic acid | 28.5% |
| oleyl oleate | 18.5% |
| squalene | 14% |
| cholesterol | 7% |
| cholesteryl palmitate | 3% |

After addition of 4 to 5 drops of artificial sebum, the artificial sebum is incorporated into the powder using a spatula, and the addition of the artificial sebum is continued until conglomerates of artificial sebum and of powder form. From this point, the artificial sebum is added one drop at a time and the mixture is then triturated with the spatula. The addition of artificial sebum is stopped when a firm, smooth paste is obtained. This paste must be able to be spread over the glass plate without cracks or the formation of lumps. The volume Vs (expressed in ml) of artificial sebum used is then noted.

The sebum uptake corresponds to the ratio Vs/m.

Advantageously, the spherical fillers in accordance with the invention have a sebum uptake greater than or equal to 10 ml/100 g, in particular greater than or equal to 20 ml/100 g, and in particular greater than or equal to 30 ml/100 g, preferably greater than or equal to 40 ml/100 g and in particular inclusively between 45 and 1500 ml/100 g, or else between 45 and 300 ml/100 g.

The spherical filler(s) advantageously has (have) an average diameter, also called median diameter or number-average size, indicated by a value $D_{50}$, which ranges from 0.05 µm to 50 µm, and preferably ranges from 2 to 40 µm. This size $D_{50}$ is given by the statistical particle size distribution for half the population, referred to as D50.

Advantageously, the spherical fillers in accordance with the invention have a BET specific surface area of greater than or equal to 300 $m^2/g$, preferably greater than 500 $m^2/g$, and preferentially greater than 600 $m^2/g$, and in particular less than 1500 $m^2/g$.

The BET specific surface area is determined according to the BET (Brunauer-Emmett-Teller) method described in the Journal of the American Chemical Society, Vol. 60, page 309, February 1938 and corresponding to the international standard ISO 5794/1 (appendix D). The BET specific surface area corresponds to the total specific surface area (thus including micropores) of the particle and in particular of the powder.

It is also possible to characterize these particles by their density, said density being capable of varying in particular according to the size of the at least partly spherical cavity of said particles.

In the context of the present invention, this density is assessed according to the following protocol, known as the tapped density protocol:

m=40 g of powder are poured into a graduated cylinder; the cylinder is then placed on the Stay 2003 instrument from Stampfvolumeter; the cylinder is then subjected to 1500 tapping operations; then the final volume Vf of tapped powder is measured directly on the cylinder. The tapped density is determined by the ratio m/Vf, in this instance 40/Vf (Vf being expressed in $cm^3$ and m in g).

In particular, the density of the spherical fillers which can be used according to the invention can range from 0.3 to 0.95, in particular from 0.45 to 0.80 and more particularly from 0.5 to 0.75.

The spherical filler(s) in accordance with the invention advantageously has (have) an expansion coefficient of 2 to 70.

Preferentially, the spherical filler(s) in accordance with the invention has (have) an untapped density at 25° C. ranging from 10 to 400 $kg/m^3$ (standard DIN 53468) and preferably from 10 to 300 $kg/m^3$.

The spherical fillers in accordance with the invention may be inorganic or organic, preferably organic.

Preferably, a composition according to the invention comprises at least one organic filler.

According to one advantageous embodiment, a composition according to the invention comprises at least one organic filler and at least one spherical filler.

As non-limiting illustrations of fillers according to the invention, mention may be made quite particularly of the particles below.

The spherical fillers in accordance with the invention advantageously have the effects of absorbing sebum and mattifying the skin (reducing its shine) and in particular in the present invention guarantee a possible forming of said cosmetic composition in powder form, by pressing, while at the same time conferring advantageous disintegration, texture and touch properties.

The spherical filler(s) is (are) present in a total content greater than or equal to 1% by weight, relative to the total weight of the composition, for example between 5% and 70% by weight, relative to the total weight of the composition, preferably between 8% and 60% by weight, better still between 10% and 55% by weight and even better still between 15% and 50% by weight.

The spherical filler(s) and the pulverulent phase are present in a respective total weight content such that the weight ratio of the spherical filler(s) to the pulverulent phase plus the colouring agent(s) is greater than or equal to 0.01 and preferably between 0.015 and 0.99.

The spherical filler(s) and the oily phase are advantageously present in the composition in a respective total content such that the weight ratio of the spherical filler(s) to the oily phase ranges from 0.02 to 4, preferably from 0.05 to 3.5 and more preferentially 0.1 to 1.

The spherical filler(s) and the liquid fatty phase are advantageously present in the composition in a respective total content such that the weight ratio of the spherical filler(s) to the liquid fatty phase ranges from 0.02 to 3.5, preferably from 0.05 to 2.5 and more preferentially 0.1 to 1.

According to one particular embodiment of the invention, the composition according to the invention comprises at least two spherical fillers that are distinct by virtue of their chemical nature, their size or their shape, preferably at least by virtue of their chemical nature.

According to one particular embodiment of the invention, the composition according to the invention comprises at least three spherical fillers that are distinct at least by virtue of their chemical nature, preferably at least by virtue of their chemical nature.

Such fillers are advantageously chosen from:
silica powders;
powders of acrylic (co)polymers, and derivatives thereof, in particular powders of acrylate (co)polymer, and derivatives thereof, advantageously chosen from a poly (methyl methacrylate) powder, a poly(methyl methacrylate/ethylene glycol dimethacrylate) powder, a poly(allyl methacrylate/ethylene glycol dimethacrylate) powder, an ethylene glycol dimethacrylate/lauryl methacrylate copolymer powder, an optionally crosslinked acrylate/alkyl acrylate copolymer powder, expanded hollow particles of acrylonitrile (co-)polymer, and mixture(s) thereof;
polyurethane powders;
silicone powders advantageously chosen from a polymethylsilsesquioxane powder, a silicone-resin-coated organopolysiloxane elastomer powder, and a powder of organosilicone particles;
powders of polyamide, such as Nylon®, in particular Nylon 12;
perlite powders.

Such spherical fillers may be coated with a hydrophobic treatment agent. The hydrophobic treatment agent may be chosen from fatty acids, for instance stearic acid; metal soaps, for instance aluminium dimyristate, the aluminium salt of hydrogenated tallow glutamate; amino acids; N-acylamino acids or salts thereof; lecithin, isopropyl triisostearyl titanate, and mixtures thereof. The N-acylamino acids can comprise an acyl group having from 8 to 22 carbon atoms, such as, for example, a 2-ethylhexanoyl, caproyl, lauroyl, myristoyl, palmitoyl, stearoyl or cocoyl group. The salts of these compounds can be aluminium, magnesium, calcium, zirconium, zinc, sodium or potassium salts. The amino acid can, for example, be lysine, glutamic acid or alanine. The term "alkyl" mentioned in the compounds cited above denotes in particular an alkyl group having from 1 to 30 carbon atoms and preferably having from 5 to 16 carbon atoms.

The spherical filler(s) is (are) present in a total content greater than or equal to 1% by weight, relative to the total weight of the composition, for example between 5% and 70% by weight, relative to the total weight of the composition, preferably between 8% and 60% by weight, better still between 10% and 55% by weight and even better still between 15% and 50% by weight.

Silica Powders

Mention may be made, as silica powder, of:
the porous silica microspheres sold under the name Silica Beads SB-700 by the company Myoshi or Sunsphere® H51 or Sunsphere® H33 by the company Asahi Glass;
the polydimethylsiloxane-coated amorphous silica microspheres sold under the name SA Sunsphere® H33 and SA Sunsphere® H53 by the company Asahi Glass.

Powders of Acrylic (Co)Polymers, and Derivatives Thereof

As powders of acrylic (co)polymers, and in particular of acrylate (co)polymer, mention may be made of:
the poly(methyl methacrylate) powders sold under the name Covabead® LH85 by the company Wackherr;
the poly(methyl methacrylate/ethylene glycol dimethacrylate) powders sold under the name Dow Corning 5640 Microsponge® Skin Oil Adsorber by the company Dow Corning or Ganzpearl® GMP-0820 by the company Ganz Chemical;
the poly(allyl methacrylate/ethylene glycol dimethacrylate) powders sold under the name Poly-Pore® L200 or Poly-Pore® E200 by the company Amcol Health and Beauty Solutions Inc.;
the ethylene glycol dimethacrylate/lauryl methacrylate copolymer powders sold under the name Polytrap® 6603 by the company Dow Corning;
the crosslinked acrylate/ethylhexyl acrylate copolymer powders sold under the name Techpolymer ACP-8C by the company Sekisui Plastics;
the expanded hollow particles of acrylonitrile (co)polymer sold under the name Expancel by the company Expancel;
and mixture(s) thereof.

The poly(methyl methacrylate)s are generally in the form of white-coloured hollow or solid spherical particles, the number-average size D50 of which is generally on the scale of a micrometer, in particular ranges from 5 to 20 microns and generally ranges from 7 to 15 microns.

The density of the poly(methyl methacrylate) particles which can be used according to the invention may range from 0.3 to 0.95, in particular from 0.45 to 0.80 and more particularly from 0.5 to 0.75.

As a non-limiting representation of the poly(methyl methacrylate)s suitable for the invention, mention may particularly be made of the poly(methyl methacrylate) particles sold by the company Wackherr under the name Covabead LH 85 and those sold by the company Nihon Junyaku under the name Jurymer MB1.

The expanded hollow particles of acrylonitrile (co)polymer are thus derived from at least one acrylonitrile polymer or copolymer. They are made of any expanded acrylonitrile polymer or copolymer which is non-toxic and non-irritant to the skin.

These particles are advantageously spherical in shape. The density of the particles is chosen in the range from 15 kg/m$^3$ to 200 kg/m$^3$, better still from 30 kg/m$^3$ to 120 kg/m$^3$ and even better still from 40 kg/m$^3$ to 80 kg/m$^3$. To obtain this low density, particles of expanded polymers or copolymers based on acrylonitrile and preferably on an acrylic or styrene monomer and/or vinylidene chloride are advantageously used.

It is possible, for example, to use a copolymer containing: from 0% to 60% of units derived from vinylidene chloride, from 20% to 90% of units derived from acrylonitrile and from 0% to 50% of units derived from an acrylic or styrene monomer, the sum of the percentages (by weight) being equal to 100. The acrylic monomer is, for example, a methyl or ethyl acrylate or methacrylate. The styrene monomer is, for example, 1-methylstyrene or styrene.

Preferably, the particles used in the present invention are hollow particles of an expanded copolymer of vinylidene chloride and of acrylonitrile, an expanded copolymer of vinylidene chloride, of acrylonitrile and of methacrylate, or a mixture thereof. These particles may be dry or hydrated.

The particles of the invention may be obtained, for example, according to the processes of patents and patent applications EP-56219, EP-348372, EP-486080, EP-320473, EP-112807 and U.S. Pat. No. 3,615,972.

The internal cavity of the particles contains in principle a gas which may be air, nitrogen or a hydrocarbon, for instance isobutane or isopentane, preferably isobutane.

Advantageously, the particles of the invention have a particle size ranging from 1 μm to 80 μm, even better still ranging from 10 μm to 50 μm and even better still from 20 μm to 40 μm.

The particles which can be used in the invention are, for example, the microspheres of expanded terpolymer of vinylidene chloride, of acrylonitrile and of methacrylate, sold under the brand Expancel by the company Expancel under the references 551 DE 40 (particle size of approximately 40 μm), 551 DE 20 (particle size of approximately 20 μm and density of approximately 65 kg/m$^3$), 551 DE 12 (particle size of approximately 12 μm), 551 DE 80 (particle size of approximately 80 μm), 461 DE 50 (particle size of approximately 50 μm). Use may also be made of the microspheres made of the same expanded terpolymer having a particle size of approximately 18 μm and a density of approximately 70 kg/m$^3$, referred to below as EL 23, or having a particle size of approximately 34 μm and a density of approximately 20 kg/m$^3$, referred to below as EL 43.

The pulverulent phase also advantageously comprises additional fillers and colouring agents.

The expanded hollow particles of acrylonitrile (co)polymers are preferably chosen from an expanded copolymer of vinylidene chloride and of acrylonitrile, an expanded copolymer of vinylidene chloride, of acrylonitrile and of methacrylate, and a mixture thereof.

Polyurethane Powders

The polyurethane powder is advantageously a powder of a copolymer of hexamethylene diisocyanate and of trimethylol hexyl lactone.

Advantageously, the composition according to the invention contains a polyurethane powder that is not film-forming, i.e. which does not form a continuous film when it is deposited onto a support such as the skin.

Such a polyurethane powder is in particular sold under the names Plastic Powder D-400, Plastic Powder D-800 and Plastic Powder T-75 by the company Toshiki.

Another polyurethane powder that may be used is the one sold under the name Plastic Powder CS-400 by the company Toshiki Silicone Powders The silicone powder(s) is (are) advantageously chosen from a polymethylsilsesquioxane powder, a silicone-resin-coated organopolysiloxane elastomer powder and a powder of organosilicone particles.

Polymethylsilsesquioxane Powder

The composition according to the invention comprises at least one silicone filler, and preferably this silicone filler is a polymethylsilsesquioxane powder.

The presence of such a filler makes it possible especially to improve the wear property, and in particular the colour-fastness, of the deposit on the skin or the lips made with the composition, without any loss of sheen. The composition according to the invention also makes it possible to obtain a deposit which is not very tacky or not at all tacky.

As polymethylsilsesquioxane powder, use may be made of the product sold under the name Tospearl by the company Momentive Performance Materials, and in particular under the reference Tospearl 145 A.

Silicone-Resin-Coated Organopolysiloxane Elastomer Powder

The composition according to the invention comprises at least one organopolysiloxane elastomer powder coated with silicone resin, in particular with silsesquioxane resin, as described, for example, in U.S. Pat. No. 5,538,793, the content of which is incorporated by way of reference.

Such elastomer powders are sold under the names KSP-100, KSP-101, KSP-102, KSP-103, KSP-104 and KSP-105 by the company Shin-Etsu, and have the INCI name: Vinyl Dimethicone/Methicone Silsesquioxane Crosspolymer.

Preferably, the silicone-resin-coated organopolysiloxane elastomer powder is a compound having the INCI name: Vinyl Dimethicone/Methicone Silsesquioxane Crosspolymer.

Silicone elastomer powders that may be mentioned include the powders sold under the names Trefil® Powder E-505C and Trefil® Powder E-506C by the company Dow Corning.

Organosilicone Particles

According to one particular embodiment of the invention, bowl-shaped hollow sphere portions are used. They can be obtained as described in patent application JP-2003 128 788; horseshoe-shaped hollow sphere portions are also described in patent application JP-A-2000-191789, or else in patent application EP 1 579 841.

As concave particles of sphere portions that may be used according to the invention, mention may in particular be made of:
  bowl-shaped particles constituted of the crosslinked organosilicone TAK-110 (methylsilanol/silicate crosslinked polymer) from the company Takemoto Oil & Fat, of width 2.5 μm, height 1.2 μm and thickness 150 nm (particles sold under the name NLK506 by the company Takemoto Oil & Fat);
  bowl-shaped particles constituted of the crosslinked organosilicone TAK-110 (methylsilanol/silicate crosslinked polymer) from the company Takemoto Oil & Fat, of width 2.5 μm, height 1.5 μm and thickness 350 nm;
  bowl-shaped particles constituted of the crosslinked organosilicone TAK-110 (methylsilanol/silicate crosslinked polymer) from the company Takemoto Oil & Fat, of width 0.7 μm, height 0.35 μm and thickness 100 nm;

bowl-shaped particles constituted of the crosslinked organosilicone TAK-110 (methylsilanol/silicate crosslinked polymer) from the company Takemoto Oil & Fat, of width 7.5 µm, height 3.5 µm and thickness 200 nm.

Polyamide Powders

Preferably, the polyamide particles have a number-average size ranging from 50 nm to 350 microns, better still between 100 nm and 100 microns and even more preferentially between 0.5 and 100 microns.

The polyamide particles are chosen from particles of nylon 12.

Mention may also be made, as polyamide powder, of the nylon powders sold under the name Orgasol® 2002 EXS NAT COS by the company Arkema.

Perlite Particles

Perlite is generally obtained from natural glass of volcanic origin, of light-grey or glossy black colour, resulting from the rapid cooling of lava, and which is in the form of small particles resembling pearl. When heated above 800° C., perlite has the particular feature of losing the water it contains and of adopting a porous expanded form (representing from four to twenty times its initial volume), enabling it to absorb large amounts of liquid, in particular of oil and water. It then has a white colour.

Perlite, which is of inorganic origin, is directly extracted from the ground and then finely milled to obtain a very fine white powder: perlite powder or perlite particles.

Perlite particles are thus particles of amorphous inorganic materials, which are advantageously expanded, derived from at least one volcanic rock.

These particles comprise at least two elements chosen from silicon, aluminium and magnesium.

More particularly, these inorganic materials are obtained by thermal expansion of a volcanic or "effusive" rock comprising from 1% to 10% by weight of water and preferably 1% to 5% by weight of water and less than 10% by weight of crystalline rock relative to the total weight of the rock composition and preferably followed by grinding. The temperature of the expansion process may range from 700 to 1500° C. and preferably from 800 to 1100° C. The expansion process described in U.S. Pat. No. 5,002,698 may in particular be used.

Volcanic or "effusive" rocks are generally produced by the rapid cooling of liquid magma in contact with air or water (quenching phenomenon giving a hyaline rock). The volcanic rocks that may be used according to the present invention are chosen from those defined according to the Streckeisen classification (1974). Among these volcanic rocks, mention may be made in particular of trachytes, latites, andesites, basalts, rhyolites and dacites. Rhyolites and dacites are particularly suitable, and even more particularly rhyolites.

The perlite particles that may be used according to the invention are preferably aluminosilicates of volcanic origin. They advantageously have the following composition:
70.0-75.0% by weight of silica $SiO_2$
12.0-15.0% by weight of aluminum oxide $Al_2O_3$
3.0-5.0% of sodium oxide $Na_2O$
3.0-5.0% of potassium oxide $K_2O$
0.5-2% of iron oxide $Fe_2O_3$→
0.2-0.7% of magnesium oxide MgO
0.5-1.5% of calcium oxide CaO
0.05-0.15% of titanium oxide $TiO_2$ In the implementation of the present invention, the perlite undergoes a first milling step so as to form perlite particles, and is dried and then calibrated. The product obtained, known as perlite ore, is gray in colour and has a size of the order of 100 µm. The perlite ore is then expanded (1000° C./2 seconds) to give more or less white particles. When the temperature reaches 850-900° C., the water trapped in the structure of the material evaporates and brings about the expansion of the material with respect to its original volume. The expanded perlite particles in accordance with the invention can be obtained by the expansion process described in U.S. Pat. No. 5,002,698.

Preferably, the perlite particles used are then milled in a second milling step in order further to reduce the size of the perlite particles used; in this case, they are referred to as expanded milled perlite (EMP). They preferably have a particle size defined by a median diameter $D_{50}$ ranging from 0.5 to 50 µm and preferably from 1 to 40 µm.

Preferentially, the perlite particles have a platelet shape; they are consequently usually called lamellar fillers, as opposed to spherical fillers, of globular shape.

The perlite particles advantageously have a coefficient of expansion of from 2 to 70.

Preferentially, the perlite particles have an untapped density at 25° C. ranging from 10 to 400 kg/m³ (standard DIN 53468) and preferably from 10 to 300 kg/m³.

According to one particular embodiment of the invention, the perlite particles have a silica content of greater than or equal to 65% by weight, relative to the total weight of the composition of the material. According to one particular embodiment of the invention, the perlite particles have a spontaneous pH, measured at 25° C. in a dispersion in water at 10% by weight, ranging from 6 to 8.

Preferably, the expanded perlite particles according to the invention have a water-absorbing capacity, measured at the wet point, ranging from 200% to 1500% and preferably from 250% to 800%.

The perlite particles used according to the invention are in particular commercially available from the company World Minerals under the trade name Perlite P1430, Perlite P2550, Perlite P2040 or OpTiMat™ 1430 OR or 2550 OR.

The spherical filler(s) which can preferentially be used in the compositions according to the invention is (are) chosen from powders of acrylic (co)polymers, and derivatives thereof, in particular powders of acrylate (co)polymer, and derivatives thereof, silicone powders, polyamide powders, and mixture(s) thereof.

Lamellar Fillers

The pulverulent phase comprises at least one lamellar filler.

The lamellar filler(s) is (are) preferably inorganic.

The lamellar filler(s) which can be used in the compositions according to the invention is (are) preferably chosen from talc, natural or synthetic mica, certain silicas, clays such as magnesium aluminium silicate, trimethyl siloxysilicate, kaolin, bentone, calcium carbonate and magnesium hydrogen carbonate, hydroxyapatite, boron nitride, fluorphlogopite, and mixtures thereof.

As representatives of such fillers preferably used in the context of the present invention, mention may be made in particular of talc, mica, fluorphlogopite, and clays such as magnesium aluminium silicate.

The lamellar filler(s) is (are) advantageously present in a composition in accordance with the present invention in a total content greater than or equal to 1% by weight, relative to the total weight of the composition, for example between 5% and 70% by weight, relative to the total weight of the composition, preferably between 10% and 60% by weight and better still between 20% and 55% by weight.

The lamellar filler(s) and the pulverulent phase are advantageously present in the composition in a respective total content such that the weight ratio of the lamellar filler(s) to the pulverulent phase is greater than or equal to 0.01, preferably between 0.015 and 0.99.

The lamellar filler(s) and the oily phase are advantageously present in the composition in a respective total content such that the weight ratio of the lamellar filler(s) to the oily phase ranges from 0.02 to 4, preferably from 0.05 to 3.5 and more preferentially 0.1 to 1.

The lamellar filler(s) and the liquid fatty phase are advantageously present in the composition in a respective total content such that the weight ratio of the lamellar filler(s) to the liquid fatty phase ranges from 0.02 to 3.5, preferably from 0.05 to 2.5 and more preferentially 0.1 to 1.

The spherical filler(s) and the lamellar filler(s) are present in a total content greater than or equal to 5% by weight, relative to the total weight of the composition, for example between 5% and 70% by weight, relative to the total weight of the composition, preferably between 10% and 60% by weight, better still between 20% and 58% by weight and even better still between 40% and 55%.

Colouring Agents

The colouring agent, or colorant, is preferably chosen from pigments, nacres and reflective particles, and mixtures thereof.

According to one particular embodiment, a composition according to the invention is free of nacres.

According to one particular embodiment, a composition according to the invention is free of pigments.

According to one particular embodiment, a composition according to the invention comprises at least one nacre, the nacre(s) being present in a higher (total) weight content than the (total) content of pigment(s).

According to one particular embodiment, a composition according to the invention comprises at least one pigment.

According to one advantageous embodiment, a composition according to the invention comprises a total content of colouring agent(s) greater than or equal to 1% by weight, in particular between 2% and 60% by weight, relative to the total weight of the composition, better still between 3% and 50% and even better still between 5% and 30% by weight, relative to the total weight of the composition.

The colouring agent(s) and the pulverulent phase are advantageously present in the composition in a respective total content such that the weight ratio of the colouring agent(s) to the pulverulent phase ranges from 0.015 to 0.5 and preferably from 0.1 to 0.2.

The colouring agent(s) and the oily phase are advantageously present in the composition in a respective total content such that the weight ratio of the colouring agent(s) to the oily phase ranges from 0.01 to 0.6, better still from 0.05 to 0.5 and even better still from 0.1 to 0.4.

The colouring agent(s) and the liquid fatty phase are advantageously present in the composition in a respective total content such that the weight ratio of the colouring agent(s) to the liquid fatty phase ranges from 0.01 to 0.6, better still from 0.05 to 0.5 and even better still from 0.1 to 0.4.

Pigments

The term "pigments" should be understood as meaning white or coloured, inorganic or organic particles of any shape, which are insoluble in the physiological medium, and which are intended to colour the composition.

The pigments may be white or coloured, and inorganic and/or organic.

Among the inorganic pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminium powder and copper powder.

The organic pigments may be chosen from the materials below, and mixtures thereof:
 cochineal carmine,
  organic pigments of azo dyes, anthraquinone dyes, indigoid dyes, xanthene dyes, pyrene dyes, quinoline dyes, triphenylmethane dyes or fluoran dyes.

Among the organic pigments, mention may be made in particular of the D&C certified pigments known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The chemical materials corresponding to each of the organic colorants mentioned previously are mentioned in the publication "International Cosmetic Ingredient Dictionary and Handbook", 1997 edition, pages 371 to 386 and 524 to 528, published by The Cosmetic, Toiletry and Fragrance Association, the content of which is incorporated into the present patent application by reference.

A composition according to the invention may comprise a total content of pigment(s) greater than or equal to 1% by weight, relative to the total weight of the composition, for example between 2% and 60% by weight, relative to the total weight of the composition, better still between 3% and 50% and even better still between 5% and 30% by weight, relative to the total weight of the composition.

The pigment(s) and the pulverulent phase are advantageously present in the composition in a respective total content such that the weight ratio of the pigment(s) to the pulverulent phase ranges from 0.015 to 0.5 and preferably from 0.1 to 0.2.

The pigment(s) and the oily phase are advantageously present in the composition in a respective total content such that the weight ratio of the colouring agent(s) to the oily phase ranges from 0.01 to 0.6, better still from 0.05 to 0.5 and even better still from 0.1 to 0.4.

The pigment(s) and the liquid fatty phase are advantageously present in the composition in a respective total content such that the weight ratio of the pigment(s) to the liquid fatty phase ranges from 0.01 to 0.6, better still from 0.05 to 0.5 and even better still from 0.1 to 0.4.

Nacres

The term "nacres" should be understood as meaning coloured particles of any shape, which may or may not be iridescent, in particular produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, and nacreous pigments based on bismuth oxychloride. They may also be mica particles at the surface of which are superposed at least two successive layers of metal oxides and/or of organic colorants.

The nacres may more particularly have a yellow, pink, red, bronze, orangey, brown, gold and/or coppery colour or tint.

As illustrations of nacres that may be introduced into the composition, mention may be made of the gold-coloured nacres sold in particular by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold in particular by the company Merck under the name Bronze fine (17384) (Colorona) and Bronze (17353) (Colorona) and by the company Engelhard under the name Super bronze (Cloisonne); the orange nacres sold in particular by the company Engelhard under the name Orange 363C (Cloisonne) and Orange MCR 101 (Cosmica) and by the company Merck under the name Passion orange (Colorona) and Matte orange (17449) (Microna); the brown nacres sold in particular by the company Engelhard under the name Nu-antique copper 340XB (Cloisonne) and Brown CL4509 (Chromalite); the nacres with a copper tint sold in particular by the company Engelhard under the name Copper 340A (Timica); the nacres with a red tint sold in particular by the company Merck under the name Sienna fine (17386) (Colorona); the nacres with a yellow tint sold in particular by the company Engelhard under the name Yellow (4502) (Chromalite); the red nacres with a gold tint sold in particular by the company Engelhard under the name Sunstone G012 (Gemtone); the pink nacres sold in particular by the company Engelhard under the name Tan opale G005 (Gemtone); the black nacres with a gold tint sold in particular by the company Engelhard under the name Nu antique bronze 240 AB (Timica), the blue nacres sold in particular by the company Merck under the name Matte blue (17433) (Microna), the white nacres with a silvery tint sold in particular by the company Merck under the name Xirona Silver, and the golden-green pinky-orangey nacres sold in particular by the company Merck under the name Indian summer (Xirona), and mixtures thereof.

Mention may also be made, still as examples of nacres, of particles comprising a borosilicate substrate coated with titanium oxide.

Particles comprising a glass substrate coated with titanium oxide are in particular sold under the name Metashine MC1080RY by the company Toyal.

Finally, examples of nacres that may also be mentioned are polyethylene terephthalate flakes, in particular those sold by the company Meadowbrook Inventions under the name Silver 1P 0.004×0.004 (silvery flakes).

According to one preferred embodiment, a composition according to the invention comprises a total content of nacre(s) less than or equal to 20% by weight, preferably less than or equal to 10% by weight and more preferentially less than or equal to 5% by weight, relative to the total weight of the composition, or is even free of nacre(s).

Such an embodiment of a composition in accordance with the invention with a high percentage of liquid fatty phase, which is provided with such a low content of nacres, or is even totally devoid of nacres, is all the more difficult to implement since the nacre generally contributes to the texture of said composition by absorbing part of the liquid fatty phase.

Reflective Particles

The term "reflective particles" denotes particles of which the size, structure, in particular the thickness of the layer(s) of which they are made and their physical and chemical nature, and surface state, allow them to reflect incident light. This reflection may, if appropriate, have an intensity sufficient to create, at the surface of the composition or mixture, when the latter is applied to the support to be made up, highlight points visible to the naked eye, that is to say more luminous points which contrast with their surroundings by appearing to sparkle.

The reflective particles may be selected so as not to significantly alter the colouration effect generated by the colouring agents with which they are combined, and more particularly so as to optimize this effect in terms of colour yield. They can more particularly have a yellow, pink, red, bronze, orangey, brown, gold and/or coppery colour or tint.

These particles can exhibit varied forms and can in particular be in the platelet or globular form, in particular the spherical form.

The reflective particles, whatever their form, may or may not exhibit a multilayer structure and, in the case of a multilayer structure, may exhibit, for example, at least one layer of uniform thickness, in particular of a reflective material.

When the reflective particles do not exhibit a multilayer structure, they can be composed, for example, of metal oxides, in particular of titanium or iron oxides obtained synthetically.

When the reflective particles exhibit a multilayer structure, they can, for example, comprise a natural or synthetic substrate, in particular a synthetic substrate, at least partially coated with at least one layer of a reflective material, in particular of at least one metal or metal material. The substrate can be made of one or more organic and/or inorganic materials.

More particularly, it can be chosen from glasses, ceramics, graphite, metal oxides, aluminas, silicas, silicates, in particular aluminosilicates and borosilicates, synthetic mica and mixtures thereof, this list not being limiting.

The reflective material can comprise a layer of metal or of a metal material.

Reflective particles are described in particular in documents JP-A-09188830, JP-A-10158450, JP-A-10158541, JP-A-07258460 and JP-A-05017710.

Still as an example of reflective particles comprising an inorganic substrate coated with a layer of metal, mention may also be made of particles comprising a silver-coated borosilicate substrate.

Particles comprising a glass substrate coated with silver, in the form of platelets, are sold under the name Microglass Metashine REFSX 2025 PS by the company Toyal. Particles comprising a glass substrate coated with nickel/chromium/molybdenum alloy are sold under the names Crystal Star GF 550 and GF 2525 by this same company.

Use may also be made of particles comprising a metal substrate, such as silver, aluminium, iron, chromium, nickel, molybdenum, gold, copper, zinc, tin, magnesium, steel, bronze or titanium, said substrate being coated with at least one layer of at least one metal oxide, such as titanium oxide, aluminium oxide, iron oxide, cerium oxide, chromium oxide, silicon oxides and mixtures thereof.

Examples that may be mentioned include the aluminium powder, bronze powder or copper powder coated with $SiO_2$ sold under the name Visionaire by the company Eckart.

According to one preferred embodiment, a composition according to the invention comprises a total content of reflective particle(s) less than or equal to 10% by weight, preferably less than 2% by weight, relative to the total weight of the composition, or is even free of reflective particle(s).

Preferably, the colouring agents comprise inorganic pigments such as a mixture of iron oxide and titanium oxide.

Oily Phase

A solid cosmetic composition according to the invention comprises at least one oily phase present in a content greater than or equal to 20% by weight, better still greater than or equal to 25% by weight, more preferably greater than or equal to 28% by weight, still more preferably greater than or equal to 30% by weight, advantageously in a content of between 25% and 50% by weight and better still from 28% to 42% by weight, relative to the total weight of the composition.

This oily phase advantageously serves as a binder in said pulverulent phase.

An oily phase comprises one or more oils.

An oily phase preferably comprises at least one non-volatile oil, and preferably consists of a mixture of non-volatile oil(s).

The term "oil" is intended to mean a water-immiscible non-aqueous compound that is liquid at ambient temperature (25° C.) and at atmospheric pressure (760 mmHg).

The term "non-volatile oil" is understood to mean an oil which remains on the skin or the keratin fibre at ambient temperature and pressure. More specifically, a non-volatile oil exhibits an evaporation rate of strictly less than 0.01 mg/cm$^2$/min.

Preferably, the oily phase, and when present the hydrophobic film-forming polymer(s), form(s) a liquid fatty phase of the compositions according to the invention.

The oily phase according to the invention preferably comprises at least one hydrocarbon-based oil, preferably non-volatile hydrocarbon-based oil.

The oily phase according to the invention preferably comprises at least one silicone oil, preferably non-volatile silicone oil.

The oily phase according to the invention preferably comprises at least one hydrocarbon-based oil, preferably non-volatile hydrocarbon-based oil, and at least one silicone oil, preferably non-volatile silicone oil.

The hydrocarbon-based oil(s), preferably non-volatile hydrocarbon-based oil(s), and the silicone oil(s), preferably non-volatile silicone oil(s), are present according to a respective total content such that the weight ratio of the hydrocarbon-based oil(s), preferably non-volatile hydrocarbon-based oil(s), to the silicone oil(s), preferably non-volatile silicone oil(s), is preferably greater than or equal to 1, preferably greater than or equal to 2, advantageously between 1.2 and 10, better still between 1.5 and 6, even better still between 1.6 and 3 and even more preferentially between 1.8 and 2.5.

Non-Volatile Hydrocarbon-Based Oil

The oily phase according to the invention advantageously comprises one or more non-volatile hydrocarbon-based oil(s) chosen from:

hydrocarbon-based oils of vegetable origin, such as phytostearyl esters, such as phytostearyl oleate, phytostearyl isostearate and lauroyl/octyldodecyl/phytostearyl glutamate; triglycerides formed from fatty acid esters of glycerol, in particular whose fatty acids may have chain lengths ranging from $C_{18}$ to $C_{36}$, these oils possibly being linear or branched, and saturated or unsaturated; these oils may in particular be heptanoic or octanoic triglycerides, shea oil, alfalfa oil, poppy oil, pumpkin oil, millet oil, barley oil, *quinoa* oil, rye oil, candlenut oil, passionflower oil, shea butter, aloe oil, sweet almond oil, peach stone oil, groundnut oil, argan oil, avocado oil, baobab oil, borage oil, broccoli oil, calendula oil, camellina oil, carrot oil, safflower oil, hemp oil, rapeseed oil, cottonseed oil, coconut oil, marrow seed oil, wheatgerm oil, jojoba oil, lily oil, macadamia oil, corn oil, meadowfoam oil, St-John's wort oil, monoi oil, hazelnut oil, apricot kernel oil, walnut oil, olive oil, evening primrose oil, palm oil, blackcurrant pip oil, kiwi seed oil, grape seed oil, pistachio oil, squash oil, pumpkin oil, *quinoa* oil, musk rose oil, sesame oil, soybean oil, sunflower oil, castor oil and watermelon oil, and mixtures thereof, or alternatively caprylic/capric acid triglycerides, such as, in particular, those sold by the company Stéarineries Dubois or, in particular, those sold under the names Miglyol 810®, 812® and 818® by the company Dynamit Nobel;

synthetic ethers containing from 10 to 40 carbon atoms;

synthetic esters, for instance oils of formula $R_1COOR_2$, in which $R_1$ represents a residue of at least one linear or branched fatty acid comprising from 1 to 40 carbon atoms and $R_2$ represents a hydrocarbon-based chain, which is in particular branched, containing from 1 to 40 carbon atoms, on condition that $R_1+R_2$ is greater than or equal to 10. The esters may be chosen in particular from fatty acid and alcohol esters, such as, for example, cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, octyldodecy stearoyl stearate, hydroxylated esters, for instance isostearyl lactate, octyl hydroxystearate, diisopropyl adipate, heptanoates, and in particular isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, in particular $C_{12}$-$C_{15}$ alkyl benzoates, polyethylene glycol diheptanoate, propylene glycol 2-diethylhexanoate, and mixtures thereof, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate;

polyol esters and pentaerythritol esters, for instance dipentaerythrityl tetrahydroxystearate/tetraisostearate;

esters of diol dimers and of diacid dimers;

copolymers of diol dimer and of diacid dimer and esters thereof, such as dilinoleyl diol dimer/dilinoleic dimer copolymers, and esters thereof;

copolymers of polyols and of diacid dimers, and esters thereof;

fatty alcohols that are liquid at ambient temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol;

$C_{12}$-$C_{22}$ higher fatty acids, such as oleic acid, linoleic acid and linolenic acid, and mixtures thereof;

dialkyl carbonates, the 2 alkyl chains possibly being identical or different, such as dicaprylyl carbonate;

oils with a molar mass of between about 400 and about 10 000 g/mol, in particular about 650 to about 10 000 g/mol, in particular from about 750 to about 7500 g/mol and more particularly ranging from about 1000 to about 5000 g/mol; mention may be made in particular, alone or as a mixture, of (i) lipophilic polymers such as polybutylenes, polyisobutylenes, for example hydrogenated, polydecenes and hydrogenated polydecenes, vinylpyrrolidone copolymers, such as the vinylpyrrolidone/1-hexadecene copolymer, and polyvinylpyrrolidone (PVP) copolymers, such as the copolymers of a $C_2$-$C_{30}$ alkene, such as a $C_3$-$C_{22}$ alkene and combinations thereof; (ii) linear fatty acid esters containing a total carbon number ranging from 35 to 70, for instance pentaerythrityl tetrapelargonate; (iii) hydroxylated esters such as polyglyceryl-2 triisostearate; (iv) aromatic esters such as tridecyl trimellitate; (v) esters of fatty alcohols or of branched $C_{24}$-$C_{28}$ fatty acids, such as those described in U.S. Pat. No. 6,491,927 and pentaerythritol esters, and in particular triisoarachidyl citrate, pentaerythrityl tetraisononanoate, glyceryl triisostearate, glyceryl 2-tridecyltetradecanoate, pentaerythrityl tetraisostearate, poly(2-glyceryl)tetraisostearate or pentaerythrityl 2-tetradecyltetradecanoate; (vi) diol dimer esters and polyesters, such as esters of diol dimer and of fatty acid, and esters of diol dimer and of diacid.

According to one advantageous embodiment, the oily phase according to the invention comprises at least one non-volatile hydrocarbon-based oil chosen from at least one synthetic ester chosen from oils of formula $R_1COOR_2$ in which $R_1$ represents a residue of at least one linear or branched fatty acid comprising from 1 to 40 carbon atoms and $R_2$ represents a hydrocarbon-based chain that is in particular branched, containing from 1 to 40 carbon atoms, on condition that $R_1+R_2$ is greater than or equal to 10. The total content of one (of) such non-volatile hydrocarbon-based oil(s) preferably represents from 10% to 40% by weight, relative to the total weight of the composition, preferably from 12% to 35% by weight and better still from 15% to 30% by weight, relative to the total weight of the composition.

According to one preferred embodiment, the oily phase preferably comprises at least one non-volatile hydrocarbon-based oil chosen from the $C_{12}$-$C_{15}$ alkyl benzoates of formula (A) below:

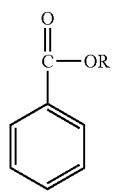

(A)

in which formula (A) R is a $C_{12}$-$C_{15}$ alkyl group.

This non-volatile oil is derived from the esterification of benzoic acid with one or more $C_{12}$-$C_{15}$ alcohol(s).

The $C_{12}$-$C_{15}$ alkyl benzoate(s) may be provided in a composition according to the invention, alone or, preferably, as a mixture with one or more additional non-volatile hydrocarbon-based or silicone oil(s), and mixtures thereof, more preferentially with at least one non-volatile silicone oil.

The content of non-volatile hydrocarbon-based oil(s), preferably of $C_{12}$-$C_{15}$ alkyl benzoates, in said composition may range from 10% to 40% by weight, in particular from 15% to 35% by weight and better still from 20% to 30% by weight relative to the total weight of the composition.

Non-Volatile Silicone Oils

According to one preferred embodiment of the invention, the oily phase according to the invention comprises at least one non-volatile silicone oil.

Advantageously, the oily phase according to the invention comprises at least one non-volatile hydrocarbon-based oil chosen from at least one synthetic ester chosen from oils of formula $R_1COOR_2$ in which $R_1$ represents a residue of at least one linear or branched fatty acid comprising from 1 to 40 carbon atoms and $R_2$ represents a hydrocarbon-based chain that is in particular branched, containing from 1 to 40 carbon atoms, on condition that $R_1+R_2$ is greater than or equal to 10, as a mixture with one or more non-volatile silicone oil(s).

Preferentially, the oily phase comprises at least one volatile hydrocarbon-based oil, advantageously chosen from $C_{12}$-$C_{15}$ alkyl benzoates, as a mixture with one or more non-volatile silicone oil(s).

The non-volatile silicone oil(s) that may be used in the invention may be chosen from silicone oils with a viscosity at 25° C. of greater than or equal to 8 centistokes (cSt) ($8\times10^{-6}$ $m^2$/s) and less than 800 000 cSt, preferably between 10 and 600 000 cSt. The viscosity of this silicone may be measured according to standard ASTM D-445.

Among these silicone oils, two types of oils may be distinguished, according to whether or not they contain phenyl. In another way, a composition according to the invention advantageously comprises at least one non-volatile silicone oil chosen from linear silicone oils and phenyl silicone oils, and mixture(s) thereof.

Representative examples of these non-volatile linear silicone oils that may be mentioned include polydimethylsiloxanes; alkyl dimethicones; vinyl methyl methicones; and also silicones modified with optionally fluorinated aliphatic groups, or with functional groups such as hydroxyl, thiol and/or amine groups.

As non-phenyl non-volatile silicone oils, mention may be made of:
  PDMSs comprising alkyl or alkoxy groups, which are pendent and/or at the ends of the silicone chain, these groups each containing from 2 to 24 carbon atoms,
  PDMSs comprising aliphatic groups, or functional groups such as hydroxyl, thiol and/or amine groups,
  polyalkylmethylsiloxanes optionally substituted with a fluorinated group, such as polymethyltrifluoropropyldimethylsiloxanes,
  polyalkylmethylsiloxanes substituted with functional groups such as hydroxyl, thiol and/or amine groups,
  polysiloxanes modified with fatty acids, fatty alcohols or polyoxyalkylenes, and mixtures thereof.

According to one particular embodiment, the oily phase comprises at least one non-phenyl linear silicone oil.

The non-phenyl linear silicone oil may be chosen in particular from the silicones of formula:

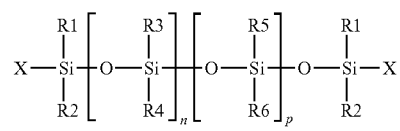

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p being integers chosen so as to have a fluid compound.

As non-volatile silicone oils that may be used according to the invention, mention may be made of those for which:
- the substituents $R_1$ to $R_6$ and X represent a methyl group, and p and n are such that the viscosity is 500 000 cSt, such as the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning,
- the substituents $R_1$ to $R_6$ and X represent a methyl group, and p and n are such that the viscosity is 60 000 cSt, such as the product sold under the name Dow Corning 200 Fluid 60000 CS by the company Dow Corning, and the product sold under the name Wacker Belsil DM 60 000 by the company Wacker,
- the substituents $R_1$ to $R_6$ and X represent a methyl group, and p and n are such that the viscosity is 350 cSt, such as the product sold under the name Dow Corning 200 Fluid 350 CS by the company Dow Corning,
- the substituents $R_1$ to $R_6$ represent a methyl group, the group X represents a hydroxyl group, and n and p are such that the viscosity is 700 cSt, such as the product sold under the name Baysilone Fluid T0.7 by the company Momentive.

According to one particular embodiment, the oily phase comprises at least one non-volatile linear oil chosen from polydimethylsiloxanes and in particular those with a viscosity of between 10 and 20 cSt.

According to one preferred embodiment variant, the oily phase comprises at least one phenyl silicone oil.

Representative examples of these non-volatile phenyl silicone oils that may be mentioned include:
- the phenyl silicone oils corresponding to the following formula:

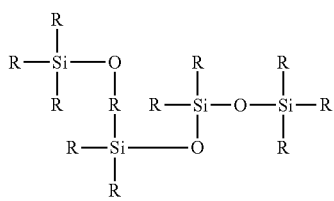

(I)

in which formula (I) the groups R represent, independently of each other, a methyl or a phenyl, with the proviso that at least one group R represents a phenyl. Preferably, in this formula, the phenyl silicone oil comprises at least three phenyl groups, for example at least four, at least five or at least six;
- the phenyl silicone oils corresponding to the following formula:

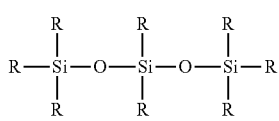

(II)

in which formula (II) the groups R represent, independently of each other, a methyl or a phenyl, with the proviso that at least one group R represents a phenyl. Preferably, in this formula, said organopolysiloxane comprises at least three phenyl groups, for example at least four or at least five. Mixtures of the phenyl organopolysiloxanes described previously may be used. Examples that may be mentioned include mixtures of triphenyl, tetraphenyl or pentaphenyl organopolysiloxanes;
- the phenyl silicone oils corresponding to the following formula:

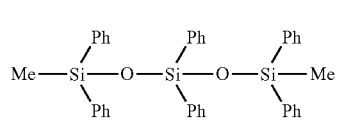

(III)

in which formula (III) Me represents methyl, Ph represents phenyl. Such a phenyl silicone is in particular manufactured by Dow Corning under the reference PH-1555 HRI or else Dow Corning 555 Cosmetic Fluid (chemical name: 1,3,5-trimethyl-1,1,3,5,5-pentaphenyl trisiloxane; INCI name: trimethyl pentaphenyl trisiloxane). The reference Dow Corning 554 Cosmetic Fluid may also be used;
- the phenyl silicone oils corresponding to the following formula:

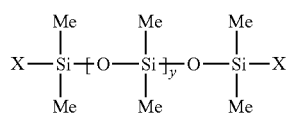

(IV)

in which formula (IV) Me represents methyl, y is between 1 and 1000 and X represents
—$CH_2$—$CH(CH_3)(Ph)$;
- the phenyl silicone oils corresponding to formula (V) below:

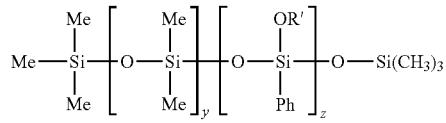

(V)

in which formula (V) Me is methyl and Ph is phenyl, OR' represents a group —$OSiMe_3$ and y is 0 or ranges between 1 and 1000, and z ranges between 1 and 1000, such that the compound (V) is a non-volatile oil.

According to a first embodiment, y ranges between 1 and 1000. Use may be made, for example, of trimethyl siloxyphenyl dimethicone, sold in particular under the reference Belsil PDM 1000 sold by the company Wacker.

According to a second embodiment, y is equal to 0. Use may be made, for example, of phenyl trimethylsiloxy trisiloxane, sold in particular under the reference Dow Corning 556 Cosmetic Grade Fluid;
- the phenyl silicone oils corresponding to formula (VI) below, and mixtures thereof:

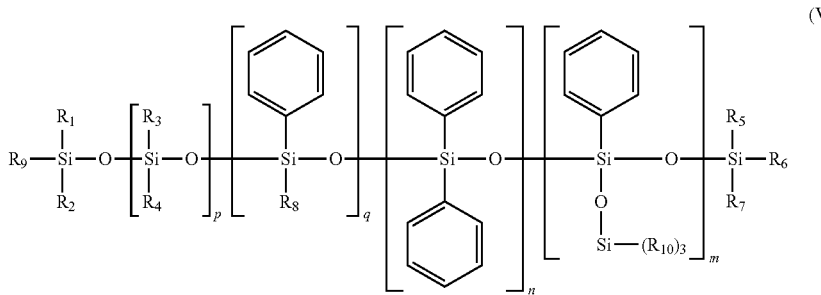

(VI)

in which formula (VI):

R$_1$ to R$_{10}$, independently of each other, are saturated or unsaturated, linear, cyclic or branched C$_1$-C$_{30}$ hydrocarbon-based radicals, m, n, p and q are, independently of each other, integers between 0 and 900, with the proviso that the sum m+n+q is other than 0.

Preferably, the sum m+n+q is between 1 and 100. Preferably, the sum m+n+p+q is between 1 and 900 and even better still between 1 and 800. Preferably, q is equal to 0;

the phenyl silicone oils corresponding to formula (VII) below, and mixtures thereof:

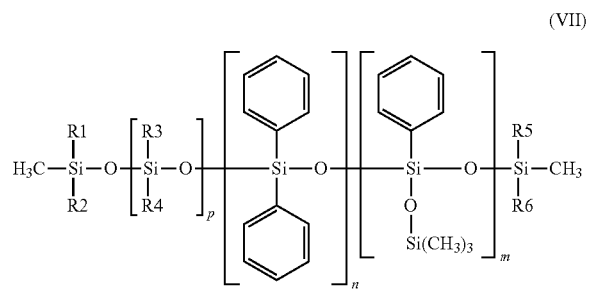

(VII)

in which formula (VII):

R$_1$ to R$_6$, independently of each other, are saturated or unsaturated, linear, cyclic or branched C$_1$-C$_{30}$ hydrocarbon-based radicals, m, n and p are, independently of each other, integers between 0 and 100, with the proviso that the sum n+m is between 1 and 100.

Preferably, R$_1$ to R$_6$, independently of each other, represent a saturated, linear or branched C$_1$-C$_{30}$ and in particular C$_1$-C$_{12}$ hydrocarbon-based radical and in particular a methyl, ethyl, propyl or butyl radical.

R$_1$ to R$_6$ may in particular be identical, and in addition may be a methyl radical.

Preferably, m=1 or 2 or 3, and/or n=0 and/or p=0 or 1 may apply, in formula (VII);

the phenyl silicone oils corresponding to formula (VIII), and mixtures thereof:

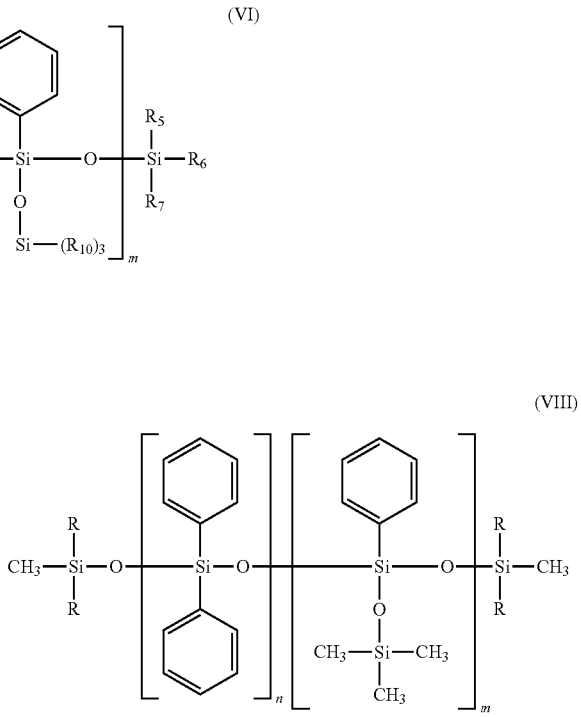

(VIII)

in which formula (VIII):

R is a C$_1$-C$_{30}$ alkyl radical, an aryl radical or an aralkyl radical, n is an integer ranging from 0 to 100, and m is an integer ranging from 0 to 100, with the proviso that the sum n+m ranges from 1 to 100.

In particular, the radicals R of formula (VIII) and R$_1$ to R$_{10}$ defined previously may each represent a linear or branched, saturated or unsaturated alkyl radical, in particular of C$_2$-C$_{20}$, in particular C$_3$-C$_{16}$ and more particularly C$_4$-C$_{10}$, or a monocyclic or polycyclic C$_6$-C$_{14}$ and in particular C$_{10}$-C$_{13}$ aryl radical, or an aralkyl radical whose aryl and alkyl residues are as defined previously.

Preferably, R of formula (VIII) and R$_1$ to R$_{10}$ may each represent a methyl, ethyl, propyl, isopropyl, decyl, dodecyl or octadecyl radical, or alternatively a phenyl, tolyl, benzyl or phenethyl radical.

According to one embodiment, use may be made of a phenyl silicone oil of formula (VIII) with a viscosity at 25° C. of between 5 and 1500 mm$^2$/s (i.e. 5 to 1500 cSt), preferably with a viscosity of between 5 and 1000 mm$^2$/s (i.e. 5 to 1000 cSt).

As phenyl silicone oil of formula (VIII), it is in particular possible to use phenyl trimethicones such as DC556 from Dow Corning (22.5 cSt), the oil Silbione 70663V30 from Rhône-Poulenc (28 cSt) or diphenyl dimethicones such as Belsil oils, in particular Belsil PDM1000 (1000 cSt), Belsil PDM 200 (200 cSt) and Belsil PDM 20 (20 cSt) from Wacker. The values in parentheses represent the viscosities at 25° C.;

the phenyl silicone oils corresponding to the following formula, and mixtures thereof:

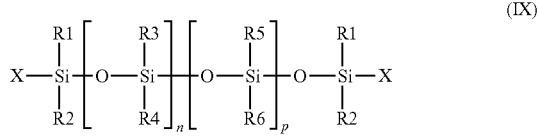

(IX)

in which formula (IX):

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms or an aryl radical, X is an alkyl radical containing from 1 to 6 carbon atoms, a hydroxyl radical or a vinyl radical, n and p being chosen so as to give the oil a weight-average molecular weight of less than 200 000 g/mol, preferably less than 150 000 g/mol and more preferably less than 100 000 g/mol.

The phenyl silicones that are most particularly suitable for the invention are those corresponding to formula (II) and in particular to formulae (III), (V) and (VIII) hereinabove.

More particularly, the phenyl silicones are chosen from phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and mixtures thereof.

Preferably, the weight-average molecular weight of the non-volatile phenyl silicone oil according to the invention ranges from 500 to 10 000 g/mol.

Preferably, the oily phase comprises at least one non-volatile silicone oil chosen from polydimethylsiloxanes, phenyl silicones of formula (II), and in particular of formulae (III), (V) and (VIII), in particular (V), and more particularly a phenyltrimethylsiloxytrisiloxane, and mixture(s) thereof. Preferably, this (these) oil(s) has (have) a viscosity of between 10 and 20 cSt.

Preferably, said oily phase comprises at least one non-volatile silicone oil chosen from linear or phenyl, preferably phenyl, non-volatile silicone oils, the total content of one (of) such non-volatile silicone oil(s) preferably representing from 1% to 20% by weight, relative to the total weight of the composition, preferably from 2% to 15% by weight and better still from 4% to 13% by weight, relative to the total weight of the composition.

Volatile Oil

The oily phase may optionally comprise at least one volatile oil.

The term "volatile oil" is intended to mean an oil (or non-aqueous medium) capable of evaporating on contact with the skin in less than one hour, at ambient temperature and atmospheric pressure. The volatile oil is a volatile cosmetic oil which is liquid at ambient temperature. More specifically, a volatile oil exhibits an evaporation rate of between 0.01 and 200 mg/cm²/min, limits included.

In order to measure this evaporation rate, 15 g of oil or of oil mixture to be tested are introduced into a crystallizing dish with a diameter of 7 cm placed on a balance in a large chamber of approximately 0.3 m³ which is regulated in temperature, at a temperature of 25° C., and regulated in hygrometry, at a relative humidity of 50%. The liquid is allowed to freely evaporate, without stirring it, while providing ventilation by means of a fan (Papst-Motoren, reference 8550 N, rotating at 2700 revolutions per minute) placed in a vertical position above the crystallizing dish containing said oil or said mixture, the blades being directed towards the crystallizing dish and at a distance of 20 cm with respect to the bottom of the crystallizing dish. The weight of oil remaining in the crystallizing dish is measured at regular intervals. The evaporation rates are expressed in mg of oil evaporated per unit of surface area (cm²) and per unit of time (minute).

This volatile oil may be a hydrocarbon-based oil, silicone oil or fluoro oil. It is preferably a hydrocarbon-based oil.

The term "hydrocarbon-based oil" is intended to mean an oil mainly containing hydrogen and carbon atoms.

The term "silicone oil" is intended to mean an oil containing at least one silicon atom, and in particular containing Si—O groups. According to one embodiment, said composition comprises less than 10% by weight of non-volatile silicone oil(s), relative to the total weight of the composition, better still less than 5% by weight, or even is free of silicone oil.

The term "fluoro oil" is intended to mean an oil comprising at least one fluorine atom.

The oils may optionally comprise oxygen, nitrogen, sulfur and/or phosphorus atoms, for example in the form of hydroxyl or acid radicals.

The volatile oils may be chosen from hydrocarbon-based oils containing from 8 to 16 carbon atoms, and in particular $C_8$-$C_{16}$ branched alkanes (also known as isoparaffins), for instance isododecane, isodecane and isohexadecane.

The volatile hydrocarbon-based oil may also be a linear volatile alkane comprising 7 to 17 carbon atoms, in particular 9 to 15 carbon atoms and more particularly 11 to 13 carbon atoms. Mention may be made in particular of n-nonadecane, n-decane, n-undecane, n-dodecane, n-tridecane, n-tetradecane, n-pentadecane and n-hexadecane, and mixtures thereof.

Preferably, the oily phase is free of volatile oil. Such an absence of volatile oil makes it possible, where appropriate, to dispense with a perfectly leaktight conditioning assembly for said composition.

Additional Volatile Solvent

A volatile solvent, or volatile oil; as previously described may be used in order to prepare the suspension to be formed. This solvent is described as additional since it is not intended to be kept in the cosmetic composition, being simply used during at least one step of manufacturing said composition.

Such an additional volatile solvent is thus advantageously removed from said composition by suctioning and/or heating.

Such an additional volatile solvent is preferably chosen from volatile oils which can be chosen from hydrocarbon-based oils containing from 8 to 16 carbon atoms, and in particular $C_8$-$C_{16}$ branched alkanes (also known as isoparaffins), for instance isododecane, isodecane and isohexadecane.

Such an additional volatile solvent can be introduced according to a ratio such that between 20 g and 50 g of isododecane are, for example, added per 100 g of composition prepared.

Hydrophobic Film-Forming Polymers

For the purposes of the invention, the term "polymer" is intended to mean a compound corresponding to the repetition of one or more units (these units being derived from compounds known as monomers). This or these unit(s) are repeated at least twice and preferably at least 3 times.

For the purposes of the present invention, the term "hydrophobic film-forming polymer" is intended to denote a film-forming polymer that has no affinity for water and, in this respect, does not lend itself to a formulation in the form of a solute in an aqueous medium. In particular, the term "hydrophobic polymer" is intended to mean a polymer having a solubility in water at 25° C. of less than 1% by weight.

The term "film-forming" polymer is intended to mean a polymer capable of forming, by itself or in the presence of an auxiliary film-forming agent, a macroscopically continuous film on a support, in particular on keratin materials, and preferably a cohesive film, and better still a film of which the cohesion and mechanical properties are such that said film may be isolable and manipulable in isolation, for example when said film is prepared by pouring onto a non-stick surface, for instance a Teflon-coated or silicone-coated surface.

In a preferred embodiment, the hydrophobic film-forming polymer is a polymer chosen from the group comprising:

film-forming polymers that are soluble in an organic solvent medium, in particular liposoluble polymers; this means that the polymer is soluble or miscible in the organic medium and will form a single homogeneous phase when it is incorporated into the medium, film-forming polymers that are dispersible in an organic solvent medium, which means that the polymer forms an insoluble phase in the organic medium, the polymer remaining stable and/or compatible once incorporated into this medium. In particular, such polymers may be in the form of non-aqueous dispersions of polymer particles, preferably dispersions in silicone oils or hydrocarbon-based oils; in one embodiment, the non-aqueous polymer dispersions comprise polymer particles stabilized on their surface with at least one stabilizer; these non-aqueous dispersions are often referred to as NADs;

film-forming polymers in the form of aqueous dispersions of polymer particles, which means that the polymer forms an insoluble phase in water, the polymer remaining stable and/or compatible once incorporated into the water, the polymer particles possibly being stabilized at their surface with at least one stabilizer. These polymer particles are often referred to as "lattices"; in this case, the composition must comprise an aqueous phase.

As hydrophobic film-forming polymer, mention may in particular be made of homopolymers and copolymers of a compound comprising an ethylenic unit, acrylic polymers and copolymers, polyurethanes, polyesters, polyureas, cellulose-based polymers such as nitrocellulose, silicone polymers such as silicone resins, silicone polyamides, polymers with a non-silicone organic backbone grafted with monomers containing a polysiloxane, polyamide polymers and copolymers, polyisoprenes, hydrocarbon-based block copolymers comprising at least one block comprising at least one styrene group and at least one block with at least one olefin.

Preferably, the film-forming polymer(s) is (are) chosen from hydrocarbon-based block copolymers, which are preferably amorphous, comprising a block with at least one styrene group and at least one block with at least one olefin.

A cosmetic composition according to the invention preferably comprises a (total) content of hydrophobic film-forming polymer(s), preferably of hydrocarbon-based block copolymer(s), greater than or equal to 0.1% by weight, in particular greater than or equal to 0.5% by weight relative to the total weight of the composition, preferably between 0.8% and 10% by weight relative to the total weight of the composition and better still between 1% and 8% by weight relative to the total weight of the composition.

Advantageously, the hydrophobic film-forming polymer(s) and the liquid fatty phase are present in a respective total content such that the weight ratio of the hydrophobic film-forming polymer(s) to the oily phase ranges from 2/98 to 30/70, from 5/95 to 20/80, from 10/90 to 25/75.

As hydrophobic film-forming polymers that are quite particularly suitable for the invention, mention is advantageously made of:

polyamide silicone block polymers, block ethylenic polymers, vinyl polymers comprising at least one carbosiloxane dendrimer derivative, copolymers comprising carboxylate groups and polydimethylsiloxane groups, silicone resins (T resin, MQ resin), lipodispersible polymers in the form of non-aqueous dispersions of polymer particles, hydrocarbon-based block copolymers, which are preferably amorphous, comprising a block with at least one styrene group and at least one block with at least one olefin, and mixtures thereof.

Silicone Resins

According to one embodiment variant, a composition according to the invention may comprise, as hydrophobic film-forming polymer, at least one silicone resin.

More generally, the term "resin" is intended to mean a compound whose structure is three-dimensional. "Silicone resins" are also referred to as "siloxane resins". Thus, for the purposes of the present invention, a polydimethylsiloxane is not a silicone resin.

The nomenclature of silicone resins (also known as siloxane resins) is known under the name "MDTQ", the resin being described as a function of the various siloxane monomer units it comprises, each of the letters "MDTQ" characterizing a type of unit.

The letter M represents the monofunctional unit of formula $R1R2R3SiO_{1/2}$, the silicon atom being bonded to only one oxygen atom in the polymer comprising this unit.

The letter D means a difunctional unit $R1R2SiO_{2/2}$ in which the silicon atom is bonded to two oxygen atoms.

The letter T represents a trifunctional unit of formula $R1SiO_{3/2}$.

Such resins are described, for example, in the *Encyclopedia of Polymer Science and Engineering*, vol. 15, John Wiley & Sons, New York, (1989), pp. 265-270, and U.S. Pat. Nos. 2,676,182, 3,627,851, 3,772,247, 5,248,739 or U.S. Pat. Nos. 5,082,706, 5,319,040, 5,302,685 and 4,935,484.

In the units M, D and T defined previously, R, namely R1 and R2, represents a hydrocarbon-based radical (in particular alkyl) containing from 1 to 10 carbon atoms, a phenyl group, a phenylalkyl group or else a hydroxyl group.

Finally, the letter Q means a tetrafunctional unit $SiO_{4/2}$ in which the silicon atom is bonded to four oxygen atoms, which are themselves bonded to the rest of the polymer.

Various silicone resins with different properties may be obtained from these different units, the properties of these polymers varying as a function of the type of monomer (or unit), the nature and number of the radical R, the length of the polymer chain, the degree of branching and the size of the pendent chains.

As silicone resins that may be used in the compositions according to the invention, use may be made, for example, of silicone resins of MQ type, of T type or of MQT type.

MQ Resins:

As examples of silicone resins of MQ type, mention may be made of the alkyl siloxysilicates of formula $[(R1)_3SiO_{1/2}]_x(SiO_{4/2})_y$ (MQ units) in which x and y are integers ranging from 50 to 80, and such that the group R1 represents a radical as defined previously, and is preferably an alkyl group containing from 1 to 8 carbon atoms or a hydroxyl group, preferably a methyl group.

As examples of solid silicone resins of MQ type of trimethyl siloxysilicate type, mention may be made of those sold under the reference SR1000 by the company General Electric, under the reference TMS 803 by the company Wacker, or under the name KF-7312J by the company Shin-Etsu or DC 749 or DC 593 by the company Dow Corning.

As silicone resins comprising MQ siloxysilicate units, mention may also be made of phenylalkylsiloxysilicate resins, such as phenylpropyldimethylsiloxysilicate (Silshine 151 sold by the company General Electric). The preparation of such resins is described in particular in U.S. Pat. No. 5,817,302.

T Resins:

Examples of silicone resins of type T that may be mentioned include the polysilsesquioxanes of formula $(RSiO_{3/2})_x$ (units T) in which x is greater than 100 and such that the group R is an alkyl group containing from 1 to 10 carbon atoms, said polysilsesquioxanes also possibly comprising Si—OH end groups.

Polymethylsilsesquioxane resins that may preferably be used are those in which R represents a methyl group, for instance those sold:

by the company Wacker under the reference Resin MK, such as Belsil PMS MK: polymer comprising $CH_3SiO_{3/2}$ repeating units (units T), which may also comprise up to 1% by weight of $(CH_3)_2SiO_{2/2}$ units (units D) and having an average molecular weight of about 10 000 g/mol, or by the company Shin-Etsu under the reference KR220L, which are composed of units T of formula $CH_3SiO_{3/2}$ and have Si—OH (silanol) end groups, under the reference KR242A, which comprise 98% of units T and 2% of dimethyl units D and have Si—OH end groups, or alternatively under the reference KR251 comprising 88% of units T and 12% of dimethyl units D and have Si—OH end groups.

MQT Resins:

Resins comprising MQT units that are in particular known are those mentioned in document U.S. Pat. No. 5,110,890.

A preferred form of resins of MQT type are MQT-propyl (also known as MQTpr) resins. Such resins that may be used in the compositions according to the invention are in particular those described and prepared in patent application WO 2005/075 542, the content of which is incorporated herein by reference.

The MQ-T-propyl resin preferably comprises the units:
(i) $(R1_3SiO_{1/2})_a$.
(ii) $(R2_2SiO_{2/2})_b$
(iii) $(R3SiO_{3/2})_c$ and
(iv) $(SiO_{4/2})_d$
with
R1, R2 and R3 independently representing a hydrocarbon-based radical (in particular alkyl) containing from 1 to 10 carbon atoms, a phenyl group, a phenylalkyl group or else a hydroxyl group and preferably an alkyl radical containing from 1 to 8 carbon atoms or a phenyl group,
a being between 0.05 and 0.5,
b being between zero and 0.3,
c being greater than zero,
d being between 0.05 and 0.6,
a+b+c+d=1, and a, b, c and d being molar fractions,
on condition that more than 40 mol % of the groups R3 of the siloxane resin are propyl groups.

Preferably, the siloxane resin comprises the units:
(i) $(R1_3SiO_{1/2})_a$.
(iii) $(R3SiO_{3/2})_c$ and
(iv) $(SiO_{4/2})_d$
with
R1 and R3 independently representing an alkyl group containing from 1 to 8 carbon atoms, R1 preferably being a methyl group and R3 preferably being a propyl group,
a being between 0.05 and 0.5 and preferably between 0.15 and 0.4,
c being greater than zero, preferably between 0.15 and 0.4,
d being between 0.05 and 0.6, preferably between 0.2 and 0.6 or alternatively between 0.2 and 0.55,
a+b+c+d=1, and a, b, c and d being molar fractions,
on condition that more than 40 mol % of the groups R3 of the siloxane resin are propyl groups.

The siloxane resins that may be used according to the invention may be obtained via a process comprising the reaction of:

A) an MQ resin comprising at least 80 mol % of units $(R1_3SiO_{1/2})_a$ and $(SiO_{4/2})_d$,
R1 representing an alkyl group containing from 1 to 8 carbon atoms, an aryl group, a carbinol group or an amino group,
a and d being greater than zero,
the ratio a/d being between 0.5 and 1.5;
and B) a T-propyl resin comprising at least 80 mol % of units $(R3SiO_{3/2})_c$,
R3 representing an alkyl group containing from 1 to 8 carbon atoms, an aryl group, a carbinol group or an amino group,
c being greater than zero,
on condition that at least 40 mol % of the groups R3 are propyl groups,
in which the mass ratio A/B is between 95/5 and 15/85 and preferably the mass ratio A/B is 30/70.

Advantageously, the mass ratio A/B is between 95/5 and 15/85. Preferably, the ratio A/B is less than or equal to 70/30. These preferred ratios have proven to allow comfortable deposits due to the absence of percolation of the rigid particles of MQ resin in the deposit.

Thus, preferably, the silicone resin is chosen from the group comprising:

a) a resin of MQ type, chosen in particular from (i) alkyl siloxysilicates, which may be trimethyl siloxysilicates, of formula $[(R1)_3SiO_{1/2}]_x(SiO_{4/2})_y$, in which x and y are integers ranging from 50 to 80, and such that the group R1 represents a hydrocarbon-based radical containing from 1 to 10 carbon atoms, a phenyl group, a phenylalkyl group or a hydroxyl group, and preferably is an alkyl group containing from 1 to 8 carbon atoms, preferably a methyl group, and (ii) phenylalkyl siloxysilicate resins, such as phenylpropyldimethyl siloxysilicate, and/or b) a resin of T type, chosen in particular from the polysilsesquioxanes of formula $(RSiO_{3/2})_x$, in which x is greater than 100 and the group R is an alkyl group containing from 1 to 10 carbon atoms, for example a methyl group, said polysilsesquioxanes also possibly comprising Si—OH end groups, and/or c) a resin of MQT type, in particular of MQT-propyl type, which may comprise units (i) $(R1_3SiO_{1/2})_a$, (ii) $(R2_2SiO_{2/2})_b$, (iii) $(R3SiO_{312})_c$ and (iv) $(SiO_{4/2})_d$,
with R1, R2 and R3 independently representing a hydrocarbon-based radical, in particular alkyl, containing from 1 to 10 carbon atoms, a phenyl group, a phenylalkyl group or else a hydroxyl group and preferably an alkyl radical containing from 1 to 8 carbon atoms or a phenyl group,
a being between 0.05 and 0.5,
b being between zero and 0.3,
c being greater than zero,
d being between 0.05 and 0.6,
a+b+c+d=1, and a, b, c and d being molar fractions,
on condition that more than 40 mol % of the groups R3 of the siloxane resin are propyl groups.

Lipodispersible Film-Forming Polymers in the Form of Non-Aqueous Dispersions of Polymer Particles, Also Known as NADs According to another embodiment variant, a composition according to the invention may comprise, as hydrophobic film-forming polymer, at least one polymer chosen from lipodispersible film-forming polymers in the form of non-aqueous dispersions of polymer particles, also known as NADs.

Non-aqueous dispersions of hydrophobic film-forming polymer that may be used include dispersions of particles of a grafted ethylenic polymer, preferably an acrylic polymer, in a liquid oily phase:
- either in the form of ethylenic polymer particles dispersed in the absence of additional stabilizer at the surface of the particles, as described in particular in document WO 04/055 081,
- or in the form of surface-stabilized particles dispersed in the liquid fatty phase. The dispersion of surface-stabilized polymer particles may be manufactured as described in document EP-A-749 747. The polymer particles may be surface-stabilized by means of a stabilizer that may be a block polymer, a grafted polymer and/or a random polymer, alone or as a mixture. Dispersions of film-forming polymer in the liquid fatty phase, in the presence of stabilizers or in particular described in documents EP-A-748 746, EP-A-924 928 and EP-A-930 060, the content of which is incorporated by way of reference into the present patent application.

Advantageously, dispersions of ethylenic polymer particles dispersed in the absence of additional stabilizer at the surface of said particles are used.

Examples of polymers of NAD type that may be mentioned more particularly include acrylic dispersions in isododecane, for instance Mexomer PAP® (acrylic copolymer as a dispersion in isododecane (25%) with pyrene/isoprene copolymer) sold by the company Chimex.

Block Ethylenic Copolymer

According to a first embodiment of the invention, the hydrophobic film-forming polymer is a block ethylenic copolymer, containing at least one first block with a glass transition temperature (Tg) of greater than or equal to 40° C. and being totally or partly derived from one or more first monomers, which are such that the homopolymer prepared from these monomers has a glass transition temperature of greater than or equal to 40° C., and at least one second block with a glass transition temperature of less than or equal to 20° C. and being derived totally or partly from one or more second monomers, which are such that the homopolymer prepared from these monomers has a glass transition temperature of less than or equal to 20° C., said first block and said second block being connected together via a random intermediate segment comprising at least one of said first constituent monomers of the first block and at least one of said second constituent monomers of the second block, and said block copolymer having a polydispersity index I of greater than 2.

The block polymer used according to the invention thus comprises at least one first block and at least one second block.

The term "at least one block" is intended to mean one or more blocks.

The term "block polymer" is intended to mean a polymer comprising at least 2 distinct blocks, preferably at least 3 distinct blocks.

The term "ethylenic polymer" is intended to mean a polymer obtained by polymerization of monomers comprising an ethylenic unsaturation.

The block ethylenic polymer used according to the invention is prepared exclusively from monofunctional monomers.

This means that the block ethylenic polymer used according to the present invention does not contain any multifunctional monomers, which make it possible to break the linearity of a polymer so as to obtain a branched or even crosslinked polymer, as a function of the content of multifunctional monomer. The polymer used according to the invention also does not contain any macromonomers (the term "macromonomer" is intended to mean a monofunctional monomer containing a pendent group of polymeric nature, and preferably having a molecular weight of greater than 500 g/mol, or alternatively a polymer comprising on only one of its ends a polymerizable (or ethylenically unsaturated) end group), which are used in the preparation of a grafted polymer.

It is pointed out that, in the text hereinabove and hereinbelow, the terms "first" and "second" blocks do not in any way condition the order of said blocks in the structure of the polymer.

The first block and the second block of the polymer used in the invention may be advantageously mutually incompatible.

The term "mutually incompatible blocks" is intended to mean that the mixture made up of a polymer corresponding to the first block and of a polymer corresponding to the second block is not miscible in the polymerization solvent, predominant by weight, of the block polymer, at ambient temperature (25° C.) and atmospheric pressure ($10^5$ Pa), for a content of the mixture of said polymers greater than or equal to 5% by weight, relative to the total weight of the mixture of said polymers and of said polymerization solvent, it being understood that:
i) said polymers are present in the mixture in a content such that the respective weight ratio ranges from 10/90 to 90/10, and that
ii) each of the polymers corresponding to the first and second blocks has an average (weight-average or number-average) molecular weight equal to that of the block polymer±15%.

In the case of a mixture of polymerization solvents, and in the event that two or more solvents are present in identical weight proportions, said polymer mixture is immiscible in at least one of them.

Needless to say, in the case of a polymerization performed in a single solvent, this solvent is the solvent that is in major amount.

The block polymer according to the invention comprises at least one first block and at least one second block that are connected together via an intermediate segment comprising at least one constituent monomer of the first block and at least one constituent monomer of the second block. The intermediate segment (also known as the intermediate block) has a glass transition temperature Tg that is between the glass transition temperatures of the first and second blocks.

The intermediate segment is a block comprising at least one constituent monomer of the first block and at least one constituent monomer of the second block of the polymer, which enables these blocks to be "compatibilized".

Advantageously, the intermediate segment comprising at least one constituent monomer of the first block and at least one constituent monomer of the second block of the polymer is a random polymer.

Preferably, the intermediate block is derived essentially from constituent monomers of the first block and of the second block.

The term "essentially" is intended to mean at least at 85%, preferably at least at 90%, better still at 95% and even better still at 100%.

The block polymer according to the invention is advantageously a film-forming block ethylenic polymer.

The term "ethylenic polymer" is intended to mean a polymer obtained by polymerization of monomers comprising an ethylenic unsaturation.

The term "film-forming polymer" is intended to mean a polymer that is capable of forming, by itself or in the presence of an auxiliary film-forming agent, a continuous deposit on a support, in particular on keratin materials.

Preferentially, the polymer according to the invention does not comprise any silicon atoms in its backbone. The term "backbone" is intended to mean the main chain of the polymer, as opposed to the pendent side chains.

Preferably, the polymer according to the invention is not water-soluble, i.e. the polymer is not soluble in water or in a mixture of water and linear or branched lower monoalcohols containing from 2 to 5 carbon atoms, for instance ethanol, isopropanol or n-propanol, without modifying the pH, at a dry matter content of at least 1% by weight, at ambient temperature (25° C.).

Preferably, the polymer according to the invention is not an elastomer.

The term "non-elastomeric polymer" is intended to mean a polymer which, when it is subjected to a stress intended to pull it (for example by 30% relative to its initial length), does not return to a length substantially identical to its initial length when the stress ceases.

More specifically, the term "non-elastomeric polymer" denotes a polymer with an instantaneous recovery $R_i$<50% and a delayed recovery $R_{2h}$<70% after having been subjected to a 30% elongation. Preferably, $R_i$ is <30% and $R_{2h}$<50%.

More specifically, the non-elastomeric nature of the polymer is determined according to the following protocol:

A polymer film is prepared by pouring a solution of the polymer in a Teflon-coated mould, followed by drying for 7 days in an environment conditioned at 23±5° C. and 50±10% relative humidity.

A film about 100 μm thick is thus obtained, from which are cut rectangular specimens (for example using a punch) 15 mm wide and 80 mm long.

This sample is subjected to a tensile stress using a machine sold under the reference Zwick, under the same temperature and humidity conditions as for the drying.

The specimens are pulled at a speed of 50 mm/min and the distance between the jaws is 50 mm, which corresponds to the initial length ($l_0$) of the specimen.

The instantaneous recovery Ri is determined in the following manner:
- the specimen is pulled by 30% ($\varepsilon_{max}$), i.e. about 0.3 times its initial length ($l_0$)
- the stress is released by applying a return speed equal to the tensile speed, i.e. 50 mm/min, and the residual elongation of the specimen is measured as a percentage, after returning to zero stress load ($\varepsilon_i$).

The percentage instantaneous recovery ($R_i$) is given by the following formula:

$$R_i=(\varepsilon_{max}-\varepsilon_{max}))\times100$$

To determine the delayed recovery, the percentage residual elongation of the specimen ($\varepsilon_{2h}$) is measured after 2 hours, 2 hours after returning to zero stress load.

The percentage delayed recovery ($R_{2h}$) is given by the following formula:

$$R_{2h}=(\varepsilon_{max}-\varepsilon_{2h}/\varepsilon_{max})\times100$$

Purely as a guide, a polymer according to one embodiment of the invention preferably has an instantaneous recovery $R_i$ of 10% and a delayed recovery $R_{2h}$ of 30%.

The polydispersity index of the polymer of the invention is greater than 2.

Advantageously, the block polymer used in the compositions according to the invention has a polydispersity index I of greater than 2, for example ranging from 2 to 9, preferably greater than or equal to 2.5, for example ranging from 2.5 to 8 and better still greater than or equal to 2.8, and in particular ranging from 2.8 to 6.

The polydispersity index I of the polymer is equal to the ratio of the weight-average mass Mw to the number-average mass Mn.

The weight-average molar mass (Mw) and number-average molar mass (Mn) are determined by gel permeation liquid chromatography (THF solvent, calibration curve established with linear polystyrene standards, refractometric detector).

The weight-average mass (Mw) of the polymer according to the invention is preferably less than or equal to 300 000; it ranges, for example, from 35 000 to 200 000 and better still from 45 000 to 150 000 g/mol.

The number-average mass (Mn) of the polymer according to the invention is preferably less than or equal to 70 000; it ranges, for example, from 10 000 to 60 000 and better still from 12 000 to 50 000 g/mol.

Preferably, the polydispersity index of the polymer according to the invention is greater than 2, for example ranging from 2 to 9, preferably greater than or equal to 2.5, for example ranging from 2.5 to 8, and better still greater than or equal to 2.8, and in particular ranging from 2.8 to 6.

First Block with a Tg of Greater than or Equal to 40° C.

The block with a Tg of greater than or equal to 40° C. has, for example, a Tg ranging from 40 to 150° C., preferably greater than or equal to 50° C., for example ranging from 50° C. to 120° C., and better still greater than or equal to 60° C., for example ranging from 60° C. to 120° C.

The glass transition temperatures indicated for the first and second blocks may be theoretical Tg values determined from the theoretical Tg values of the constituent monomers of each of the blocks, which may be found in a reference manual such as the Polymer Handbook, 3rd Edition, 1989, John Wiley, according to the following relationship, known as Fox's law:

$$1/Tg=\Sigma(\omega_i/Tg_i),i$$

$\omega_i$ being the weight fraction of the monomer i in the block under consideration and $Tg_i$ being the glass transition temperature of the homopolymer of the monomer i.

Unless otherwise indicated, the Tg values indicated for the first and second blocks in the present patent application are theoretical Tg values.

The difference between the glass transition temperatures of the first and second blocks is generally greater than 10° C., preferably greater than 20° C. and better still greater than 30° C.

In the present invention, the expression "between . . . and . . . " is intended to denote a range of values for which the limits mentioned are excluded, and "from . . . to . . . " and "ranging from . . . to . . . " are intended to denote a range of values for which the limits are included.

The block with a Tg of greater than or equal to 40° C. may be a homopolymer or a copolymer.

The block with a Tg of greater than or equal to 40° C. may be derived totally or partially from one or more monomers which are such that the homopolymer prepared from these monomers has a glass transition temperature of greater than or equal to 40° C. This block may also be referred to as a "rigid block".

In the case where this block is a homopolymer, it is derived from monomers which are such that the homopolymers prepared from these monomers have glass transition temperatures of greater than or equal to 40° C. This first block may be a homopolymer consisting of only one type of monomer (for which the Tg of the corresponding homopolymer is greater than or equal to 40° C.).

In the case where the first block is a copolymer, it may be totally or partially derived from one or more monomers, the nature and concentration of which are chosen such that the Tg of the resulting copolymer is greater than or equal to 40° C.

The copolymer may comprise, for example:
monomers which are such that the homopolymers prepared from these monomers have Tg values of greater than or equal to 40° C., for example a Tg ranging from 40° C. to 150° C., preferably greater than or equal to 50° C., for example ranging from 50° C. to 120° C. and better still greater than or equal to 60° C., for example ranging from 60° C. to 120° C., and
monomers which are such that the homopolymers prepared from these monomers have Tg values of less than 40° C., chosen from the monomers with a Tg of between 20° C. and 40° C. and/or the monomers with a Tg of less than or equal to 20° C., for example a Tg ranging from −100° C. to 20° C., preferably less than 15° C., in particular ranging from −80° C. to 15° C. and better still less than 10° C., for example ranging from −50° C. to 0° C., as described later.

The first monomers whose homopolymers have a glass transition temperature of greater than or equal to 40° C. are chosen, preferably, from the following monomers, also known as the main monomers:
the methacrylates of formula $CH_2=C(CH_3)-COOR_1$
in which $R_1$ represents a linear or branched unsubstituted alkyl group containing from 1 to 4 carbon atoms, such as a methyl, ethyl, propyl or isobutyl group or $R_1$ represents a $C_4$ to $C_{12}$ cycloalkyl group, preferably a C8 to C12 cycloalkyl, such as isobornyl methacrylate,
the acrylates of formula $CH_2=CH-COOR_2$
in which $R_2$ represents a $C_4$ to $C_{12}$ cycloalkyl group such as an isobornyl group or a tert-butyl group,
the (meth)acrylamides of formula:

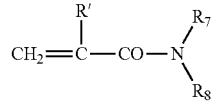

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group, and R' denotes H or methyl. Examples of monomers that may be mentioned include N-butylacrylamide, N-tert-butylacrylamide, N-isopropylacrylamide, N,N-dimethylacrylamide and N,N-dibutylacrylamide, and mixtures thereof.

The first block is advantageously obtained from at least one acrylate monomer of formula $CH_2=CH-COOR_2$ and from at least one methacrylate monomer of formula $CH_2=C(CH_3)-COOR_2$ in which $R_2$ represents a $C_4$ to $C_{12}$ cycloalkyl group, preferably a $C_8$ to $C_{12}$ cycloalkyl, such as isobornyl. The monomers and the proportions thereof are preferably chosen such that the glass transition temperature of the first block is greater than or equal to 40° C.

According to one embodiment, the first block is obtained from:
i) at least one acrylate monomer of formula $CH_2=CH-COOR_2$ in which $R_2$ represents a $C_4$ to $C_{12}$ cycloalkyl group, preferably a $C_8$ to $C_{12}$ cycloalkyl group, such as isobornyl,
ii) and at least one methacrylate monomer of formula $CH_2=C(CH_3)-COOR'_2$ in which $R'_2$ represents a $C_4$ to $C_{12}$ cycloalkyl group, preferably a $C_8$ to $C_{12}$ cycloalkyl group, such as isobornyl.

According to one embodiment, the first block is obtained from at least one acrylate monomer of formula $CH_2=CH-COOR_2$ in which $R_2$ represents a $C_8$ to $C_{12}$ cycloalkyl group, such as isobornyl, and from at least one methacrylate monomer of formula $CH_2=C(CH_3)-COOR'_2$ in which $R'_2$ represents a $C_8$ to $C_{12}$ cycloalkyl group, such as isobornyl.

Preferably, $R_2$ and $R'_2$ represents, independently or simultaneously, an isobornyl group.

Preferably, the block copolymer comprises from 50% to 80% by weight of isobornyl methacrylate/acrylate, from 10% to 30% by weight of isobutyl acrylate and from 2% to 10% by weight of acrylic acid.

The first block may be obtained exclusively from said acrylate monomer and from said methacrylate monomer.

The acrylate monomer and the methacrylate monomer are preferably in mass proportions of between 30/70 and 70/30, preferably between 40/60 and 60/40 and in particular of the order of 50/50.

The proportion of the first block advantageously ranges from 20% to 90% by weight of the polymer, better still from 30% to 80% and even better still from 60% to 80%.

According to one embodiment, the first block is obtained by polymerization of isobornyl methacrylate and isobornyl acrylate.

Second Block with a Glass Transition Temperature of Less than 20° C.

The second block advantageously has a glass transition temperature Tg of less than or equal to 20° C., for example has a Tg ranging from −100° C. to 20° C., preferably less than or equal to 15° C., in particular ranging from −80° C. to 15° C. and better still less than or equal to 10° C., for example ranging from −100° C. to 10° C., in particular ranging from −30° C. to 10° C.

The second block is totally or partially derived from one or more second monomers, which are such that the homopolymer prepared from these monomers has a glass transition temperature of less than or equal to 20° C.

This block may also be referred to as a "flexible block".

The monomer with a Tg of less than or equal to 20° C. (known as the second monomer) is preferably chosen from the following monomers:

the acrylates of formula $CH_2$=$CHCOOR_3$, $R_3$ representing a linear or branched $C_1$ to $C_{12}$ unsubstituted alkyl group, with the exception of the tert-butyl group, into which one or more heteroatoms chosen from O, N and S is (are) optionally inserted, the methacrylates of formula $CH_2$=$C(CH_3)$—$COOR_4$, $R_4$ representing a linear or branched $C_6$ to $C_{12}$ unsubstituted alkyl group, into which one or more heteroatoms chosen from O, N and S is (are) optionally inserted, the vinyl esters of formula $R_5$—CO—O—CH=$CH_2$ in which $R_5$ represents a linear or branched $C_4$ to $C_{12}$ alkyl group, ethers of vinyl alcohol and of a $C_4$ to $C_{12}$ alcohol, N—($C_4$ to $C_{12}$)alkyl acrylamides, such as N-octylacrylamide, and mixtures thereof.

The preferred monomers with a Tg of less than or equal to 20° C. are isobutyl acrylate, 2-ethylhexyl acrylate or mixtures thereof in all proportions.

Each of the first and second blocks may contain in small proportion at least one constituent monomer of the other block.

Thus, the first block may contain at least one constituent monomer of the second block, and vice versa.

Each of the first and/or second blocks may comprise, in addition to the monomers indicated above, one or more other monomers known as additional monomers, which are different from the main monomers mentioned above.

The nature and amount of this or these additional monomer(s) are chosen such that the block in which they are present has the desired glass transition temperature.

This additional monomer is chosen, for example, from:

ethylenically unsaturated monomers comprising at least one tertiary amine function, for instance 2-vinylpyridine, 4-vinylpyridine, dimethylaminoethyl methacrylate, diethylaminoethyl methacrylate and dimethylaminopropylmethacrylamide, and salts thereof, the methacrylates of formula $CH_2$=$C(CH_3)$—$COOR_6$, in which $R_6$ represents a linear or branched alkyl group containing from 1 to 4 carbon atoms, such as a methyl, ethyl, propyl or isobutyl group, said alkyl group being substituted with one or more substituents chosen from hydroxyl groups (for instance 2-hydroxypropyl methacrylate and 2-hydroxyethyl methacrylate) and halogen atoms (Cl, Br, I or F), such as trifluoroethyl methacrylate, the methacrylates of formula $CH_2$=$C(CH_3)$—$COOR_9$, $R_9$ representing a linear or branched $C_6$ to $C_{12}$ alkyl group, into which one or more heteroatoms chosen from O, N and S are optionally inserted, said alkyl group being substituted with one or more substituents chosen from hydroxyl groups and halogen atoms (Cl, Br, I or F), the acrylates of formula $CH_2$=$CHCOOR_{10}$, $R_{10}$ representing a linear or branched $C_1$ to $C_{12}$ alkyl group substituted with one or more substituents chosen from hydroxyl groups and halogen atoms (Cl, Br, I or F), such as 2-hydroxypropyl acrylate and 2-hydroxyethyl acrylate, or $R_{10}$ represents a $C_1$ to $C_{12}$ alkyl-O—POE (polyoxyethylene) with repetition of the oxyethylene unit 5 to 10 times, for example methoxy-POE, or $R_{10}$ represents a polyoxyethylenated group comprising from 5 to 10 ethylene oxide units.

In particular, the first block may comprise as additional monomer:

(meth)acrylic acid, preferably acrylic acid, tert-butyl acrylate, the methacrylates of formula $CH_2$=$C(CH_3)$—$COOR_1$, in which $R_1$ represents a linear or branched unsubstituted alkyl group containing from 1 to 4 carbon atoms, such as a methyl, ethyl, propyl or isobutyl group, (meth)acrylamides of formula:

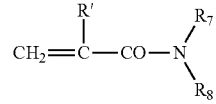

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group, and R' denotes H or methyl. Examples of monomers that may be mentioned include N-butylacrylamide, N-tert-butylacrylamide, N-isopropylacrylamide, N,N-dimethylacrylamide and N,N-dibutylacrylamide, and mixtures thereof.

The additional monomer may represent 0.5% to 30% by weight relative to the weight of the polymer. According to one embodiment, the polymer of the invention does not contain any additional monomer.

Preferably, the polymer of the invention comprises at least isobornyl acrylate and isobornyl methacrylate monomers in the first block and isobutyl acrylate and acrylic acid monomers in the second block.

Preferably, the polymer comprises at least isobornyl acrylate and isobornyl methacrylate monomers in equivalent weight proportion in the first block and isobutyl acrylate and acrylic acid monomers in the second block.

Preferably, the polymer comprises at least isobornyl acrylate and isobornyl methacrylate monomers in equivalent weight proportion in the first block, and isobutyl acrylate and acrylic acid monomers in the second block, the first block representing 70% by weight of the polymer.

Preferably, the polymer comprises at least isobornyl acrylate and isobornyl methacrylate monomers in equivalent weight proportion in the first block and isobutyl acrylate and acrylic acid monomers in the second block. Preferably, the block with a Tg of greater than 40° C. represents 70% by weight of the polymer, and acrylic acid represents 5% by weight of the polymer.

According to one embodiment, the first block does not comprise any additional monomer.

According to one preferred embodiment, the second block comprises acrylic acid as additional monomer. In particular, the second block is advantageously obtained from an acrylic acid monomer and from at least one other monomer with a Tg of less than or equal to 20° C.

The block copolymer may advantageously comprise more than 2% by weight of acrylic acid monomers, and in particular from 2% to 15% by weight, for example from 3% to 15% by weight, in particular from 4% to 15% by weight or even from 4% to 10% by weight of acrylic acid monomers, relative to the total weight of said copolymer.

The constituent monomers of the second block and the proportions thereof are chosen such that the glass transition temperature of the second block is less than or equal to 20° C.

Intermediate Segment

The intermediate segment (also known as the intermediate block) connects the first block and the second block of the polymer used according to the present invention. The intermediate segment results from the polymerization:

i) of the first monomer(s), and optionally of the additional monomer(s), which remain available after their polymerization to a maximum degree of conversion of 90% to form the first block, ii) and of the second monomer(s), and optionally of the additional monomer(s), added to the reaction mixture.

The formation of the second block is initiated when the first monomers no longer react or are no longer incorporated into the polymer chain either because they are all consumed or because their reactivity no longer allows them to be.

Thus, the intermediate segment comprises the first available monomers, resulting from a degree of conversion of these first monomers of less than or equal to 90%, during the introduction of the second monomer(s) during the synthesis of the polymer.

The intermediate segment of the block polymer is a random polymer (which may also be referred to as a random block). This means that it comprises a random distribution of the first monomer(s) and of the second monomer(s) and also of the additional monomer(s) that may be present.

Thus, the intermediate segment is a random block, as are the first block and the second block if they are not homopolymers (i.e. if they are both formed from at least two different monomers).

Process for Preparing the Copolymer

The block ethylenic copolymer according to the invention is prepared by free radical polymerization, according to the techniques that are well known for this type of polymerization.

The free radical polymerization is performed in the presence of an initiator whose nature is adapted, in a known manner, as a function of the desired polymerization temperature and of the polymerization solvent. In particular, the initiator may be chosen from initiators bearing a peroxide function, redox couples or other free radical polymerization initiators known to those skilled in the art.

In particular, examples of initiators bearing a peroxide function that may be mentioned include:

a. peroxyesters such as tert-butyl peroxyacetate, tert-butyl perbenzoate, tert-butyl peroxy-2-ethylhexanoate (Trigonox 21S from Akzo Nobel) or 2,5-bis(2-ethyl-hexanoylperoxy)-2,5-dimethylhexane (Trigonox 141 from Akzo Nobel);
b. peroxydicarbonates such as diisopropyl peroxydicarbonate;
c. peroxy ketones such as methyl ethyl ketone peroxide;
d. hydroperoxides such as aqueous hydrogen peroxide solution ($H_2O_2$) or tert-butyl hydroperoxide;
e. diacyl peroxides such as acetyl peroxide or benzoyl peroxide;
f. dialkyl peroxides such as di-tert-butyl peroxide;
g. inorganic peroxides such as potassium peroxodisulfate ($K_2S_2O_8$).

As initiator in the form of a redox couple, mention may be made of the potassium thiosulfate+potassium peroxodisulfate couple, for example.

According to one preferred embodiment, the initiator is chosen from organic peroxides comprising from 8 to 30 carbon atoms. Preferably, the initiator used is 2,5-bis(2-ethylhexanoylperoxy)-2,5-dimethylhexane sold under the reference Trigonox® 141 by the company Akzo Nobel.

The block copolymer used according to the invention is prepared by free radical polymerization and not by controlled or living polymerization. In particular, the polymerization of the block ethylenic copolymer is performed in the absence of control agents, and in particular in the absence of control agents conventionally used in living or controlled polymerization processes, such as nitroxides, alkoxyamines, dithioesters, dithiocarbamates, dithiocarbonates or xanthates, trithiocarbonates or copper-based catalysts, for example.

As mentioned previously, the intermediate segment is a random block, as are the first block and the second block if they are not homopolymers (i.e. if they are both formed from at least two different monomers).

The block copolymer may be prepared by free radical polymerization, and in particular by a process that consists in mixing, in the same reactor, a polymerization solvent, an initiator, at least one monomer with a glass transition temperature of greater than or equal to 40° C., at least one monomer with a glass transition temperature of less than or equal to 20° C., according to the following sequence:

some of the polymerization solvent and optionally some of the initiator and of the monomers for the first addition are poured into the reactor, and the mixture is heated to a reaction temperature of between 60° C. and 120° C., said at least one first monomer with a Tg of greater than or equal to 40° C. and optionally some of the initiator are then poured in, in a first addition, and the mixture is left to react for a time T corresponding to a maximum degree of conversion of said monomers of 90%, further polymerization initiator and said at least one second monomer with a glass transition temperature of less than or equal to 20° C. are then poured into the reactor, in a second addition, and the mixture is left to react for a time T' after which the degree of conversion of said monomers reaches a plateau, the reaction mixture is cooled to ambient temperature.

Preferably, the copolymer may be prepared by free radical polymerization, in particular by a process that consists in mixing, in the same reactor, a polymerization solvent, an initiator, an acrylic acid monomer, at least one monomer with a glass transition temperature of less than or equal to 20° C., at least one acrylate monomer of formula $CH_2=CH-COOR_2$ in which $R_2$ represents a $C_4$ to $C_{12}$ cycloalkyl group and at least one methacrylate monomer of formula $CH_2=C(CH_3)-COOR'_2$ in which $R'_2$ represents a $C_4$ to $C_{12}$ cycloalkyl group, according to the following sequence of steps:

some of the polymerization solvent and optionally some of the initiator and of the monomers for the first addition are poured into the reactor, and the mixture is heated to a reaction temperature of between 60° C. and 120° C., said at least one acrylate monomer of formula $CH_2=CH-COOR_2$ and said at least one methacrylate monomer of formula $CH_2=C(CH_3)-COOR'_2$, as monomers with a Tg of greater than or equal to 40° C., and optionally some of the initiator, are then poured in, in a first addition, and the mixture is left to react for a time T corresponding to a maximum degree of conversion of said monomers of 90%, further polymerization initiator, the acrylic acid monomer and said at least one monomer with a glass transition temperature of less than or equal to 20° C. are then poured into the reactor, in a second addition, and the mixture is left to react for a time T' after which the degree of conversion of said monomers reaches a plateau, the reaction mixture is cooled to ambient temperature.

The term "polymerization solvent" is intended to mean a solvent or a mixture of solvents. In particular, as polymerization solvents that may be used, mention may be made of:

ketones that are liquid at ambient temperature, such as methyl ethyl ketone, methyl isobutyl ketone, diisobutyl ketone, isophorone, cyclohexanone or acetone;

propylene glycol ethers that are liquid at ambient temperature, such as propylene glycol monomethyl ether, propylene glycol monomethyl ether acetate or dipropylene glycol n-butyl monoether;

short-chain esters (containing from 3 to 8 carbon atoms in total), such as ethyl acetate, methyl acetate, propyl acetate, n-butyl acetate or isopentyl acetate;

ethers that are liquid at ambient temperature, such as diethyl ether, dimethyl ether or dichlorodiethyl ether;

alkanes that are liquid at ambient temperature, such as decane, heptane, dodecane, isododecane, cyclohexane and isohexadecane.

aromatic cyclic compounds that are liquid at ambient temperature, such as toluene and xylene; aldehydes that are liquid at ambient temperature, such as benzaldehyde and acetaldehyde, and mixtures thereof.

Conventionally, the polymerization solvent is a volatile oil with a flash point of less than 80° C. The flash point is measured in particular according to standard ISO 3679.

The polymerization solvent may be chosen in particular from ethyl acetate, butyl acetate, alcohols such as isopropanol or ethanol, and aliphatic alkanes such as isododecane, and mixtures thereof. Preferably, the polymerization solvent is a mixture of butyl acetate and isopropanol or isododecane.

According to another embodiment, the copolymer may be prepared by free radical polymerization according to a preparation process that consists in mixing, in the same reactor, a polymerization solvent, an initiator, at least one monomer with a glass transition temperature of less than or equal to 20° C. and at least one monomer with a Tg of greater than or equal to 40° C., according to the following sequence of steps:

some of the polymerization solvent and optionally some of the initiator and of the monomers for the first addition are poured into the reactor, and the mixture is heated to a reaction temperature of between 60° C. and 120° C., said at least one monomer with a glass transition temperature of less than or equal to 20° C. and optionally some of the initiator are then poured in, in a first addition, and the mixture is left to react for a time T corresponding to a maximum degree of conversion of said monomers of 90%, further polymerization initiator and said at least one monomer with a Tg of greater than or equal to 40° C. are then poured into the reactor, in a second addition, and the mixture is left to react for a time T' after which the degree of conversion of said monomers reaches a plateau, the reaction mixture is cooled to ambient temperature.

According to one preferred embodiment, the copolymer may be prepared by free radical polymerization according to a preparation process that consists in mixing, in the same reactor, a polymerization solvent, an initiator, an acrylic acid monomer, at least one monomer with a glass transition temperature of less than or equal to 20° C., at least one monomer with a Tg of greater than or equal to 40° C., and in particular, as monomers with a Tg of greater than or equal to 40° C., at least one acrylate monomer of formula $CH_2$=CH—$COOR_2$ in which $R_2$ represents a $C_4$ to $C_{12}$ cycloalkyl group and at least one methacrylate monomer of formula $CH_2$=$C(CH_3)$—$COOR'_2$ in which $R'_2$ represents a $C_4$ to $C_{12}$ cycloalkyl group, according to the following sequence of steps:

some of the polymerization solvent and optionally some of the initiator and of the monomers for the first addition are poured into the reactor, and the mixture is heated to a reaction temperature of between 60° C. and 120° C., the acrylic acid monomer and said at least one monomer with a glass transition temperature of less than or equal to 20° C. and optionally some of the initiator are then poured in, in a first addition, and the mixture is left to react for a time T corresponding to a maximum degree of conversion of said monomers of 90%, further polymerization initiator, said at least one acrylate monomer of formula $CH_2$=CH—$COOR_2$ and said at least one methacrylate monomer of formula $CH_2$=$C(CH_3)$—$COOR'_2$, as monomer with a Tg of greater than or equal to 40° C., are then poured into the reactor, in a second addition, and the mixture is left to react for a time T' after which the degree of conversion of said monomers reaches a plateau, the reaction mixture is cooled to ambient temperature.

The polymerization temperature is preferably about 90° C.

The reaction time after the second addition is preferably between 3 and 6 hours.

Preferably, the block ethylenic copolymer is present in the composition in a dry matter content ranging from 0.1% to 60%, better still from 0.5% to 50%, better still from 1% to 30% and even better still from 1% to 40% by weight relative to the total weight of the composition.

Distillation of the Synthesis Solvent

It is possible to perform a step of total or partial removal of said volatile oil or solvent (conventionally isododecane). This is then performed in particular by distillation, optionally under vacuum, and optional addition of non-volatile hydrocarbon-based ester oil comprising at least 16 carbon atoms and having a molar mass of less than 650 g/mol, such as octyldodecyl neopentanoate (in particular 2-octyldodecyl neopentanoate).

This step is performed at elevated temperature and optionally under vacuum to distil off a maximum amount of volatile synthesis solvent, and is known to those skilled in the art.

Polyamide Silicone Block Polymer

According to another embodiment variant, a composition according to the invention comprises, as hydrophobic film-forming polymer, at least one polyamide silicone block polymer, also known as a silicone polyamide.

The silicone polyamides are preferably solid at ambient temperature (25° C.) and atmospheric pressure (760 mmHg).

For the purposes of the invention, the term "polymer" is intended to mean a compound containing at least 2 repeating units, preferably at least 3 repeating units and even better still 10 repeating units.

The silicone polyamides of the composition of the invention may be polymers of the polyorganosiloxane type, for instance those described in documents U.S. Pat. Nos. 5,874,069, 5,919,441, 6,051,216 and 5,981,680. According to the invention, the silicone polymers may belong to the following two families:

(1) polyorganosiloxanes comprising at least two amide groups, these two groups being located in the polymer chain, and/or (2) polyorganosiloxanes comprising at least two amide groups, these two groups being located on grafts or branches.

According to a first variant, the silicone polymers are polyorganosiloxanes as defined above and in which the units capable of establishing hydrogen interactions are located in the polymer chain.

The silicone polymers may be more particularly polymers comprising at least one unit corresponding to general formula I:

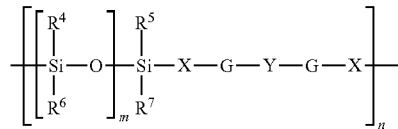

in which:

$R^4$, $R^5$, $R^6$ and $R^7$, which may be identical or different, represent a group chosen from:

linear, branched or cyclic, saturated or unsaturated, $C_1$ to $C_{40}$ hydrocarbon-based groups, possibly containing in their chain one or more oxygen, sulfur and/or nitrogen atoms, and possibly being partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulfur and/or nitrogen atoms, the groups X, which may be identical or different, represent a linear or branched $C_1$ to $C_{30}$ alkylenediyl group, possibly containing in its chain one or more oxygen and/or nitrogen atoms, Y is a saturated or unsaturated $C_1$ to $C_{50}$ linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl, $C_1$ to $C_3$ hydroxyalkyl and $C_1$ to $C_6$ aminoalkyl groups, or Y represents a group corresponding to the formula:

in which:

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^8$ represents a linear or branched $C_1$-$C_{50}$ alkyl group or a polyorganosiloxane chain, possibly comprising one or more ester, amide, urethane, thiocarbamate, urea, thiourea and/or sulfonamide groups, which may possibly be linked to another chain of the polymer, the groups G, which may be identical or different, represent divalent groups chosen from:

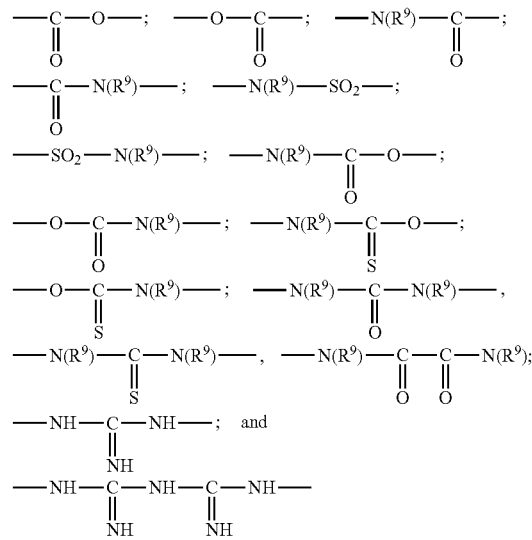

in which $R^9$ represents a hydrogen atom or a linear or branched $C_1$ to $C_{20}$ alkyl group, on condition that at least 50% of the groups $R^9$ of the polymer represent a hydrogen atom and that at least two of the groups G of the polymer are a group other than:

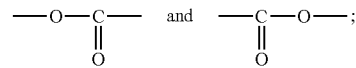

n is an integer ranging from 2 to 500 and preferably from 2 to 200, and m is an integer ranging from 1 to 1000, preferably from 1 to 700 and even better still from 6 to 200.

According to the invention, 80% of the groups $R^4$, $R^5$, $R^6$ and $R^7$ of the polymer are preferably chosen from methyl, ethyl, phenyl and 3,3,3-trifluoropropyl groups.

According to the invention, Y can represent various divalent groups, optionally comprising, in addition, one or two free valencies to establish bonds with other units of the polymer or copolymer. Preferably, Y represents a group chosen from:

$C_1$ to $C_{20}$, preferably $C_1$ to $C_{10}$, linear alkylene groups, branched $C_{30}$ to $C_{56}$ alkylene groups possibly comprising rings and unconjugated unsaturations, $C_5$-$C_6$ cycloalkylene groups, phenylene groups optionally substituted with one or more $C_1$ to $C_{40}$ alkyl groups, $C_1$ to $C_{20}$ alkylene groups comprising from 1 to 5 amide groups, $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, polyorganosiloxane chains of formula:

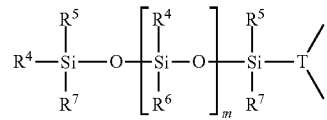

in which $R^4$, $R^5$, $R^6$, $R^7$, T and m are as defined above, and polyorganosiloxane chains of formula:

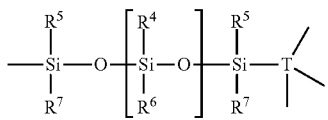

According to the second variant, the polyorganosiloxanes may be polymers comprising at least one unit corresponding to formula (II):

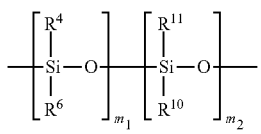
(II)

in which:

$R^4$ and $R^6$, which may be identical or different, are as defined above for formula (I), $R^{10}$ represents a group as defined above for $R^4$ and $R^6$, or represents the group of formula —X-G-$R^{12}$ in which X and G are as defined above for formula (I) and $R^{12}$ represents a hydrogen atom or a linear, branched or cyclic, saturated or unsaturated $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^{11}$ represents the group of formula —X-G-$R^{12}$ in which X, G and $R^{12}$ are as defined above, $m_1$ is an integer ranging from 1 to 998, and $m_2$ is an integer ranging from 2 to 500.

According to the invention, the silicone polymer used as structuring agent may be a homopolymer, that is to say a polymer comprising several identical units, in particular units of formula (I) or of formula (II).

According to the invention, it is also possible to use a silicone polymer made up of a copolymer comprising several different units of formula (I), that is to say a polymer in which at least one of $R^4$, $R^5$, $R^6$, $R^7$, X, G, Y, m and n is different in one of the units. The copolymer may also be made up of several units of formula (II), in which at least one of $R^4$, $R^6$, $R^{10}$, $R^{11}$, $m_1$ and $m_2$ is different in at least one of the units.

It is also possible to use a polymer comprising at least one unit of formula (I) and at least one unit of formula (II), the units of formula (I) and the units of formula (II) possibly being identical to or different from each other.

According to one variant of the invention, it is also possible to use a polymer furthermore comprising at least one hydrocarbon-based unit comprising two groups capable of establishing hydrogen interactions, chosen from ester, amide, sulfonamide, carbamate, thiocarbamate, urea, urethane, thiourea, oxamido, guanidino and biguanidino groups, and combinations thereof.

These copolymers may be block polymers or grafted polymers.

According to one advantageous embodiment of the invention, the groups capable of establishing hydrogen interactions are amide groups of formulae —C(O)NH— and —HN—C(O)—. In this case, the structuring agent may be a polymer comprising at least one unit of formula (III) or (IV):

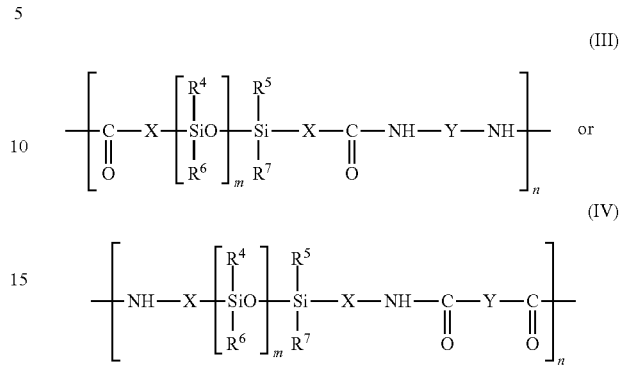

in which $R^4$, $R^5$, $R^6$, $R^7$, X, Y, m and n are as defined above.

Such a unit may be obtained:

either by a condensation reaction between a silicone containing α,ω-carboxylic acid ends and one or more diamines, according to the following reaction scheme:

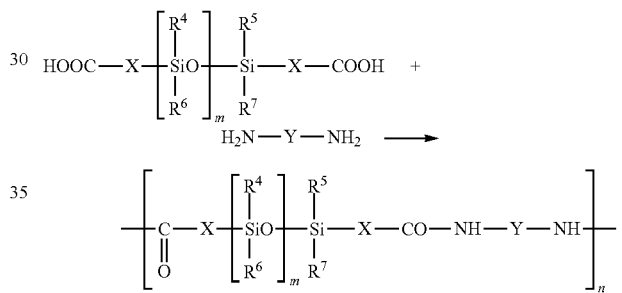

or by reaction of two molecules of α-unsaturated carboxylic acid with a diamine according to the following reaction scheme:

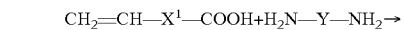

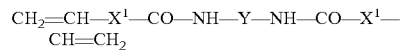

followed by the addition of a siloxane to the ethylenic unsaturations, according to the following scheme:

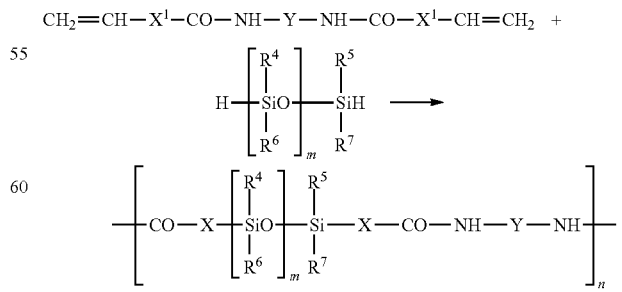

in which $X^1$—$(CH_2)_2$— corresponds to the X defined above and Y, $R^4$, $R^5$, $R^6$, $R^7$ and m are as defined above, or by reaction of a silicone containing α,ω-NH$_2$ ends and a diacid of formula HOOC—Y—COOH according to the following reaction scheme:

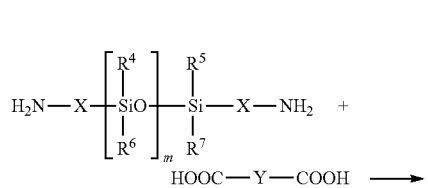
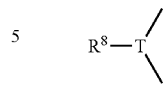

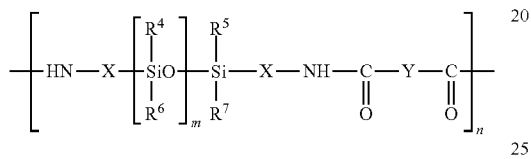

In these polyamides of formula (III) or (IV), m ranges from 1 to 700, in particular from 15 to 500 and especially from 50 to 200, and n ranges in particular from 1 to 500, preferably from 1 to 100 and better still from 4 to 25, X is preferably a linear or branched alkylene chain containing from 1 to 30 carbon atoms, in particular 1 to 20 carbon atoms, especially from 5 to 15 carbon atoms and more particularly 10 carbon atoms, and Y is preferably an alkylene chain that is linear or branched, or which may comprise rings and/or unsaturations, containing from 1 to 40 carbon atoms, in particular from 1 to 20 carbon atoms and better still from 2 to 6 carbon atoms, in particular 6 carbon atoms.

In formulae (III) and (IV), the alkylene group representing X or Y can optionally contain in its alkylene part at least one of the following components:

1 to 5 amide, urea, urethane or carbamate groups, a C$_5$ or C$_6$ cycloalkyl group, and a phenylene group optionally substituted with 1 to 3 identical or different C$_1$ to C$_3$ alkyl groups.

In formulae (III) and (IV), the alkylene groups may also be substituted with at least one component chosen from the group consisting of:

a hydroxyl group, a C$_3$ to C$_8$ cycloalkyl group, one to three C$_1$ to C$_{40}$ alkyl groups, a phenyl group optionally substituted with one to three C$_1$ to C$_3$ alkyl groups, a C$_1$ to C$_3$ hydroxyalkyl group, and a C$_1$ to C$_6$ aminoalkyl group.

In these formulae (III) and (IV), Y may also represent:

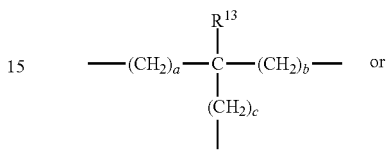

in which R$^8$ represents a polyorganosiloxane chain, and T represents a group of formula:

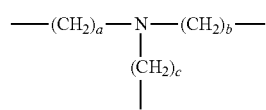

in which a, b and c are, independently, integers ranging from 1 to 10, and R$^{13}$ is a hydrogen atom or a group such as those defined for R$^4$, R$^5$, R$^6$ and R$^7$.

In formulae (III) and (IV), R$^4$, R$^5$, R$^6$ and R$^7$ preferably represent, independently, a linear or branched C$_1$ to C$_{40}$ alkyl group, preferably a CH$_3$, C$_2$H$_5$, n-C$_3$H$_7$ or isopropyl group, a polyorganosiloxane chain or a phenyl group optionally substituted with one to three methyl or ethyl groups.

As has been seen previously, the polymer may comprise identical or different units of formula (III) or (IV).

Thus, the polymer may be a polyamide containing several units of formula (III) or (IV) of different lengths, i.e. a polyamide corresponding to formula (V):

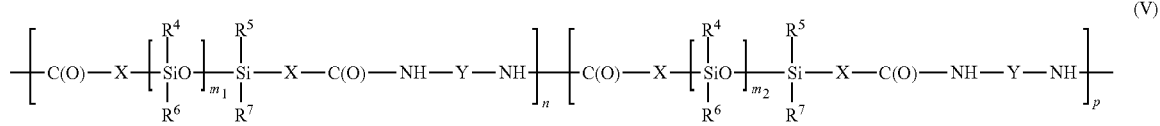

in which X, Y, n, and R$^4$ to R$^7$ have the meanings given above, m$_1$ and m$_2$, which are different, are chosen in the range from 1 to 1000, and p is an integer ranging from 2 to 300.

In this formula, the units may be structured to form either a block copolymer, or a random copolymer or an alternating copolymer. In this copolymer, the units may be not only of different lengths, but also of different chemical structures, for example containing different groups Y. In this case, the polymer may correspond to formula VI:

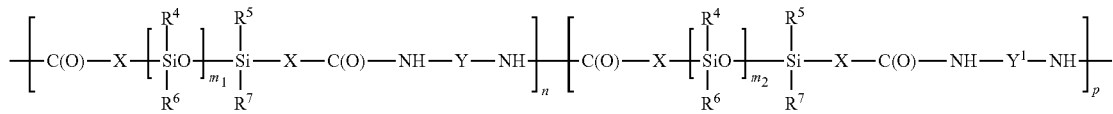

(VI)

in which $R^4$ to $R^7$, X, Y, $m_1$, $m_2$, n and p have the meanings given above and $Y^1$ is different from Y but chosen from the groups defined for Y. As previously, the various units may be structured to form either a block copolymer, or a random copolymer or an alternating copolymer.

In this first embodiment of the invention, the structuring agent may also consist of a grafted copolymer. Thus, the polyamide containing silicone units may be grafted and optionally crosslinked with silicone chains containing amide groups. Such polymers may be synthesized with trifunctional amines.

In this case, the polymer may comprise at least one unit of formula (VII):

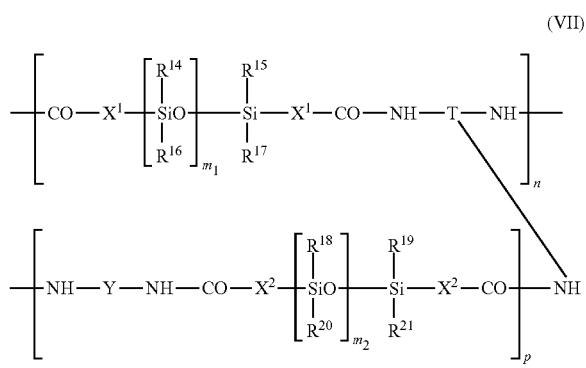

(VII)

in which $X^1$ and $X^2$, which are identical or different, have the meaning given for X in formula (I), n is as defined in formula (I), Y and T are as defined in formula (I), $R^{14}$ to $R^{21}$ are groups chosen from the same group as the groups $R^4$ to $R^7$, $m_1$ and $m_2$ are numbers in the range from 1 to 1000, and p is an integer ranging from 2 to 500.

In formula (VII), it is preferred that:
p is in the range from 1 to 25 and even better still from 1 to 7,
$R^{14}$ to $R^{21}$ are methyl groups,
T corresponds to one of the following formulae:

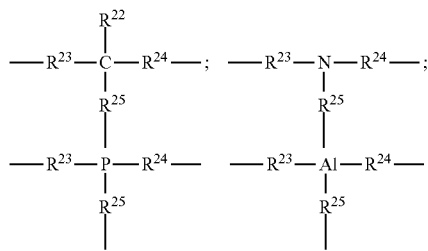

in which $R^{22}$ is a hydrogen atom or a group chosen from the groups defined for $R^4$ to $R^7$, and $R^{23}$, $R^{24}$ and $R^{25}$ are, independently, linear or branched alkylene groups, and more preferably corresponds to the formula:

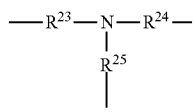

in particular with $R^{23}$, $R^{24}$ and $R^{25}$ representing —CH$_2$—CH$_2$—,
$m_1$ and $m_2$ are in the range from 15 to 500 and even better still from 15 to 45,
$X^1$ and $X^2$ represent —(CH$_2$)$_{10}$—, and
Y represents —CH$_2$—.

These polyamides containing a grafted silicone unit of formula (VII) may be copolymerized with polyamide silicones of formula (II) to form block copolymers, alternating copolymers or random copolymers. The weight percentage of grafted silicone units (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to one embodiment variant of the invention, a copolymer of silicone polyamide and of hydrocarbon-based polyamide, or a copolymer comprising units of formula (III) or (IV) and hydrocarbon-based polyamide units, may be used. In this case, the polyamide-silicone units may be located at the ends of the hydrocarbon-based polyamide.

According to one preferred embodiment, the silicone polyamide comprises units of formula III, preferably in which the groups $R^4$, $R^5$, $R^6$ and $R^7$ represent methyl groups, one from among X and Y represents an alkylene group of 6 carbon atoms and the other represents an alkylene group of 11 carbon atoms, n representing the degree of polymerization, DP, of the polymer. By way of example of such silicone polyamides, mention may be made of the compounds sold by the company Dow Corning under the names DC 2-8179 (DP 100) and DC 2-8178 (DP 15), the INCI name of which is Nylon-611/dimethicone copolymers.

Advantageously, the composition according to the invention comprises at least one polydimethylsiloxane block polymer of general formula (I) with an m index value of about 15.

More preferably, the composition according to the invention comprises at least one polymer comprising at least one unit of formula (III) in which m ranges from 5 to 100, in particular from 10 to 75 and more particularly is about 15; more preferably, $R^4$, $R^5$, $R^6$ and $R^7$ represent, independently, a linear or branched $C_1$ to $C_{40}$ alkyl group, preferably a CH$_3$, $C_2H_5$, n-$C_3H_7$ or isopropyl group in formula (III).

According to a preferred mode, use is made of the silicone polyamide polymer sold by the company Dow Corning under the name DC 2-8179 (DP 100).

As an example of a silicone polymer that may be used, mention may be made of one of the silicone polyamides obtained in accordance with Examples 1 to 3 of U.S. Pat. No. 5,981,680.

Vinyl Polymer Comprising at Least One Carbosiloxane Dendrimer-Based Unit

According to one particular embodiment, a composition used according to the invention may comprise, as hydrophobic film-forming polymer, at least one vinyl polymer comprising at least one carbosiloxane dendrimer-based unit.

The vinyl polymer used according to the invention in particular has a backbone and at least one side chain, which comprises a carbosiloxane dendrimer-based unit having a carbosiloxane dendrimer structure.

Vinyl polymers comprising at least one carbosiloxane dendrimer unit as described in patent applications WO 03/045 337 and EP 963 751 by the company Dow Corning may be used in particular.

The term "carbosiloxane dendrimer structure" in the context of the present invention represents a molecular structure with branched groups of high molecular weights, said structure having high regularity in the radial direction starting from the bond to the backbone. Such carbosiloxane dendrimer structures are described in the form of a highly branched siloxane-silylalkylene copolymer in the laid-open Japanese patent application Kokai 9-171 154.

A vinyl polymer according to the invention may contain carbosiloxane dendrimer-based units that may be represented by the following general formula:

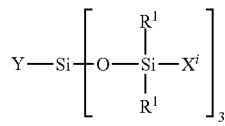

in which $R^1$ represents an aryl group or an alkyl group containing from 1 to 10 carbon atoms, and $X^i$ represents a silylalkyl group which, when i=1, is represented by the formula:

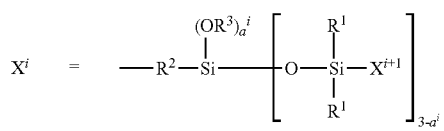

in which $R^1$ is as defined above, $R^2$ represents an alkylene group containing from 2 to 10 carbon atoms, $R^3$ represents an alkyl group containing from 1 to 10 carbon atoms, $X^{i+1}$ represents a hydrogen atom, an alkyl group containing from 1 to 10 carbon atoms, an aryl group, or the silylalkyl group defined above with i=i+1; i is an integer from 1 to 10 which represents the generation of said silylalkyl group, and $a^i$ is an integer from 0 to 3; Y represents a radical-polymerizable organic group chosen from:

organic groups containing a methacrylic group or an acrylic group and that are represented by the formulae:

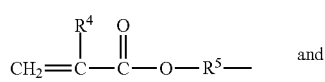

and

-continued

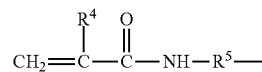

in which $R^4$ represents a hydrogen atom or an alkyl group, $R^5$ represents an alkylene group containing from 1 to 10 carbon atoms, such as a methylene group, an ethylene group, a propylene group or a butylene group, the methylene group and the propylene group being preferred; and organic groups containing a styryl group and that are represented by the formula:

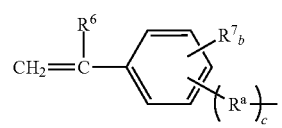

in which $R^6$ represents a hydrogen atom or an alkyl group, $R^7$ represents an alkyl group containing from 1 to 10 carbon atoms, such as a methyl group, an ethyl group, a propyl group or a butyl group, the methyl group being preferred, $R^8$ represents an alkylene group containing from 1 to 10 carbon atoms, such as a methylene group, an ethylene group, a propylene group or a butylene group, the ethylene group being preferred, b is an integer from 0 to 4, and c is 0 or 1 such that if c is 0, $—(R^8)_c—$ represents a bond.

According to one embodiment, $R^1$ may represent an aryl group or an alkyl group containing from 1 to 10 carbon atoms. The alkyl group may preferably be represented by a methyl group, an ethyl group, a propyl group, a butyl group, a pentyl group, an isopropyl group, an isobutyl group, a cyclopentyl group or a cyclohexyl group. The aryl group may preferably be represented by a phenyl group and a naphthyl group. The methyl and phenyl groups are more particularly preferred, and the methyl group is preferred among all.

A vinyl polymer containing at least one carbosiloxane dendrimer-based unit has a molecular side chain containing a carbosiloxane dendrimer structure, and may be the product of polymerization of:

(A) from 0 to 99.9 parts by weight of a vinyl monomer; and (B) from 100 to 0.1 parts by weight of a carbosiloxane dendrimer containing a radical-polymerizable organic group, represented by the general formula:

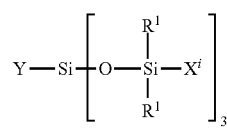

in which Y represents a radical-polymerizable organic group, $R^1$ represents an aryl group or an alkyl group containing from 1 to 10 carbon atoms, and $X^i$ represents a silylalkyl group which, when i=1, is represented by the formula:

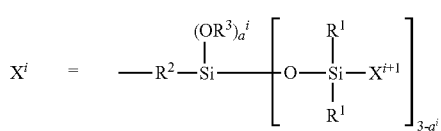

in which $R^1$ is as defined above, $R^2$ represents an alkylene group containing from 2 to 10 carbon atoms, $R^3$ represents an alkyl group containing from 1 to 10 carbon atoms, $X^{i+1}$ represents a hydrogen atom, an alkyl group containing from 1 to 10 carbon atoms, an aryl group, or the silylalkyl group defined above with i=i+1; i is an integer from 1 to 10 which represents the generation of said silylalkyl group, and $a^i$ is an integer from 0 to 3; in which said radical-polymerizable organic group contained in the component (B) is chosen from:

organic groups containing a methacrylic group or an acrylic group and that are represented by the formulae:

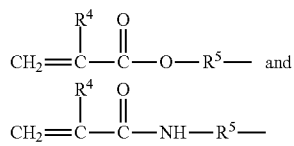

in which $R^4$ represents a hydrogen atom or an alkyl group, $R^5$ represents an alkylene group containing from 1 to 10 carbon atoms; and organic groups containing a styryl group and that are represented by the formula:

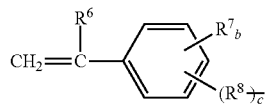

in which $R^6$ represents a hydrogen atom or an alkyl group, $R^7$ represents an alkyl group containing from 1 to 10 carbon atoms, $R^8$ represents an alkylene group containing from 1 to 10 carbon atoms, b is an integer from 0 to 4, and c is 0 or 1, such that if c is 0, —$(R^8)_c$— represents a bond.

The monomer of vinyl type that is the component (A) in the vinyl polymer is a monomer of vinyl type that contains a radical-polymerizable vinyl group.

There is no particular limitation as regards such a monomer.

The following are examples of this monomer of vinyl type: methyl methacrylate, ethyl methacrylate, n-propyl methacrylate, isopropyl methacrylate or a methacrylate of a lower alkyl analogue; glycidyl methacrylate; butyl methacrylate, butyl acrylate, n-butyl methacrylate, isobutyl methacrylate, tert-butyl acrylate, tert-butyl methacrylate, n-hexyl methacrylate, cyclohexyl methacrylate, 2-ethylhexyl acrylate, 2-ethylhexyl methacrylate, octyl methacrylate, lauryl methacrylate, stearyl acrylate, stearyl methacrylate or a higher-analogue methacrylate; vinyl acetate, vinyl propionate or a vinyl ester of a lower fatty acid analogue; vinyl caproate, vinyl 2-ethylhexoate, vinyl laurate, vinyl stearate or an ester of a higher fatty acid analogue; styrene, vinyltoluene, benzyl methacrylate, phenoxyethyl methacrylate, vinylpyrrolidone or similar vinylaromatic monomers; methacrylamide, N-methylolmethacrylamide, N-methoxymethylmethacrylamide, isobutoxymethoxymethacrylamide, N,N-dimethylmethacrylamide or similar monomers of vinyl type containing amide groups; hydroxyethyl methacrylate, hydroxypropyl alcohol methacrylate or similar monomers of vinyl type containing hydroxyl groups; acrylic acid, methacrylic acid, itaconic acid, crotonic acid, fumaric acid, maleic acid or similar monomers of vinyl type containing a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl vinyl ether, cetyl vinyl ether, 2-ethylhexyl vinyl ether or a similar monomer of vinyl type with ether bonds; methacryloxypropyltrimethoxysilane, polydimethylsiloxane containing a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

Multifunctional vinyl monomers may also be used.

The following represent examples of such compounds: trimethylolpropane trimethacrylate, pentaerythrityl trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropanetrioxyethyl methacrylate, tris(2-hydroxyethyl)isocyanurate dimethacrylate, tris(2-hydroxyethyl)isocyanurate trimethacrylate, polydimethylsiloxane capped with styryle groups having divinylbenzene groups on both ends, or similar silicone compounds having unsaturated groups.

A carbosiloxane dendrimer, which is the component (B), may be represented by the following formula:

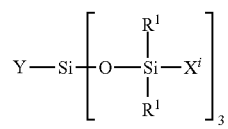

in which Y represents a radical-polymerizable organic group as defined previously.

The following represent the preferred examples of radical-polymerizable organic group Y: an acryloxymethyl group, a 3-acryloxypropyl group, a methacryloxymethyl group, a 3-methacryloxypropyl group, a 4-vinylphenyl group, a 3-vinylphenyl group, a 4-(2-propenyl)phenyl group, a 3-(2-propenyl)phenyl group, a 2-(4-vinylphenyl) ethyl group, a 2-(3-vinylphenyl)ethyl group, a vinyl group, an allyl group, a methallyl group, and a 5-hexenyl group.

R' is as defined previously.

$X^i$ represents a silylalkyl group that is represented by the following formula, when i is equal to 1:

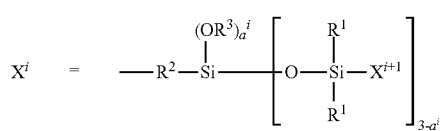

in which $R^1$ is as defined above.

$R^2$ represents an alkylene group containing from 2 to 10 carbon atoms, such as an ethylene group, a propylene group, a butylene group, a hexylene group or a similar linear alkylene group; a methylmethylene group, a methylethylene group, a 1-methylpentylene group, a 1,4-dimethylbutylene group or a similar branched alkylene group.

Ethylene, methylethylene, hexylene, 1-methylpentylene and 1,4-dimethylbutylene groups are preferred among all of them.

$R^3$ represents an alkyl group containing from 1 to 10 carbon atoms, such as methyl, ethyl, propyl, butyl and isopropyl groups.

$X^{i+1}$ represents a hydrogen atom, an alkyl group containing from 1 to 10 carbon atoms, an aryl group or the silylalkyl group with i=i+1, $a^i$ is an integer from 0 to 3, and i is an integer from 1 to 10 that indicates the generation number, which represents the number of repetitions of the silylalkyl group.

For example, when the generation number is equal to 1, the carbosiloxane dendrimer may be represented by the first general formula shown below, in which Y, $R^1$, $R^2$ and $R^3$ are as defined above, $R^{12}$ represents a hydrogen atom or is identical to $R^1$; $a^1$ is identical to $a^i$. Preferably, the total average number of groups $OR^3$ in a molecule is within the range from 0 to 7.

When the generation number is equal to 2, the carbosiloxane dendrimer may be represented by the second general formula shown below, in which Y, $R^1$, $R^2$, $R^3$ and $R^{12}$ are the same as defined above; $a^1$ and $a^2$ represent the $a^i$ of the indicated generation. Preferably, the total average number of groups $OR^3$ in a molecule is within the range from 0 to 25.

When the generation number is equal to 3, the carbosiloxane dendrimer is represented by the third general formula shown below, in which Y, $R^1$, $R^2$, $R^3$ and $R^{12}$ are the same as defined above; $a^1$, $a^2$ and $a^3$ represent the $a^i$ of the indicated generation. Preferably, the total average number of groups $OR^3$ in a molecule is within the range from 0 to 79.

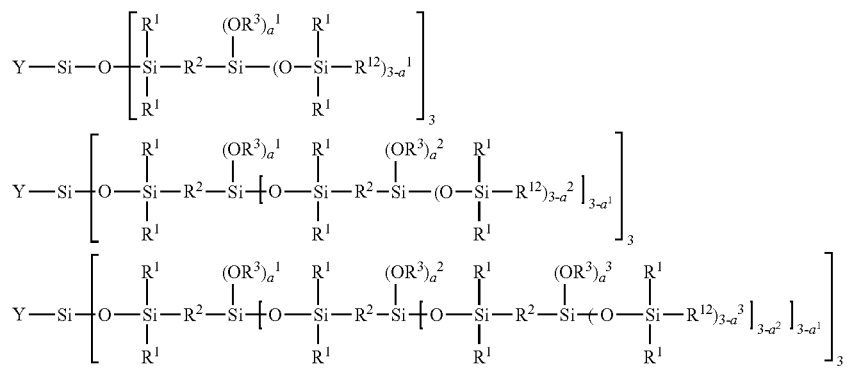

A carbosiloxane dendrimer that contains a radical-polymerizable organic group may be represented by the following mean structural formulae:

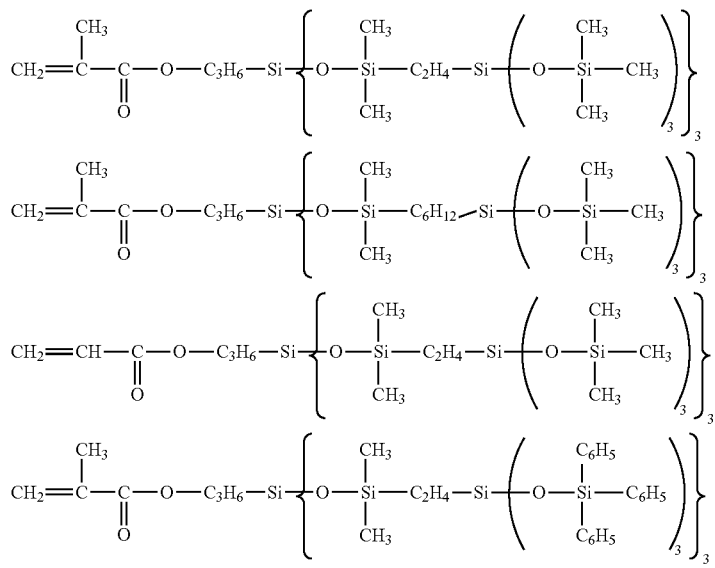

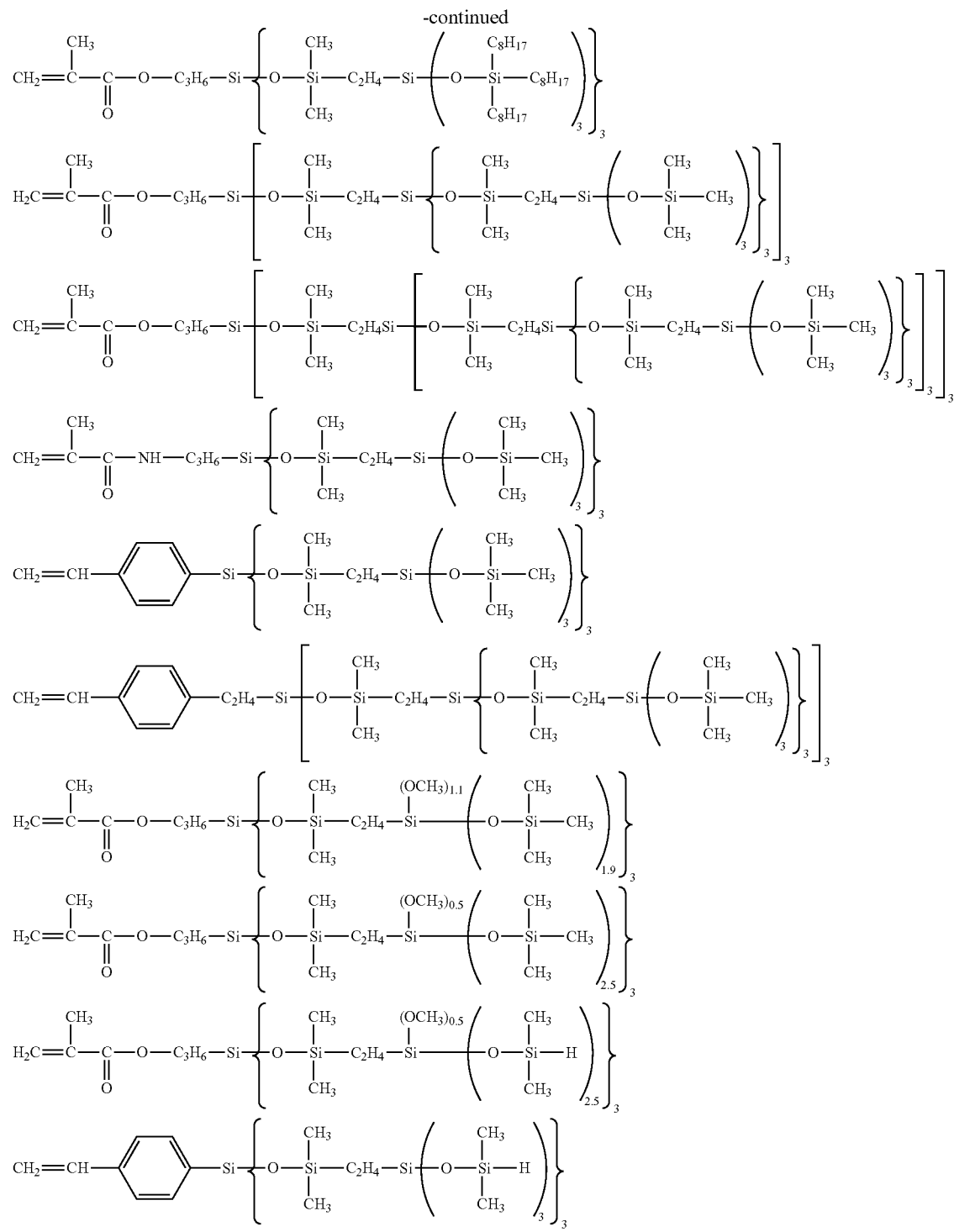

The carbosiloxane dendrimer may be manufactured according to the process for manufacturing a branched silalkylene siloxane described in Japanese patent application Hei 9-171 154.

For example, it may be produced by subjecting an organosilicon compound containing a hydrogen atom linked to a silicon atom, represented by the following general formula:

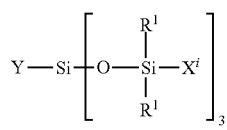

and an organosilicon compound containing an alkenyl group, to a hydrosilylation reaction.

In the above formula, the organosilicon compound may be represented by 3-methacryloxypropyltris(dimethylsiloxy)silane, 3-acryloxypropyltris—may be chosen from polymers such that the carbosiloxane dendrimer-based unit is (dimethylsiloxy)silane, and 4-vinylphenyltris(dimethylsiloxy)silane. The organosilicon compound which contains an alkenyl group may be represented by vinyltris(trimethylsiloxy)silane, vinyltris(dimethylphenylsiloxy)silane, and 5-hexenyltris(trimethylsiloxy)silane.

The hydrosilylation reaction is performed in the presence of a chloroplatinic acid, a complex of vinylsiloxane and of platinum, or a similar transition metal catalyst.

A vinyl polymer containing at least one carbosiloxane dendrimer-based unit may be chosen from polymers such that the carbosiloxane dendrimer-based unit is a carbosiloxane dendritic structure represented by formula (I):

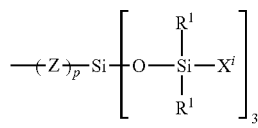

in which Z is a divalent organic group, "p" is 0 or 1, $R^1$ is an aryl or alkyl group having from 1 to 10 carbon atoms and $X^i$ is a silylalkyl group represented by formula (II):

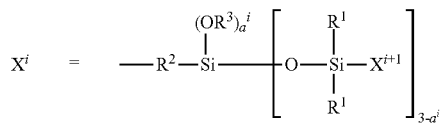

in which $R^1$ is as defined above, $R^2$ is an alkylene group containing from 1 to 10 carbon atoms, $R^3$ is an alkyl group containing from 1 to 10 carbon atoms and $X^{i+1}$ is a group chosen from the group comprising hydrogen atoms, aryl groups and alkyl groups containing up to 10 carbon atoms, and silylalkyl groups $X^i$ in which the power "i" is an integer from 1 to 10 indicating the generation of the starting silylalkyl group in each carbosiloxane dendritic structure with a value of 1 for the group $X^i$ in formula (I) and the index "$a^i$" is an integer from 0 to 3.

In a vinyl polymer containing at least one carbosiloxane dendrimer-based unit, the polymerization ratio between the components (A) and (B), in terms of the weight ratio between (A) and (B), may be within a range from 0/100 to 99.9/0.1, or even from 0.1/99.9 to 99.9/0.1 and preferably within a range from 1/99 to 99/1. A ratio between the components (A) and (B) of 0/100 means that the compound becomes a homopolymer of component (B).

A vinyl polymer containing at least one carbosiloxane dendrimer-based unit may be obtained by copolymerization of the components (A) and (B), or by polymerization of the component (B) alone.

The polymerization may be a free-radical polymerization or an ionic polymerization, but free-radical polymerization is preferred.

The polymerization may be performed by bringing about a reaction between the components (A) and (B) in a solution for a period of from 3 to 20 hours in the presence of a radical initiator at a temperature of from 50° C. to 150° C.

A suitable solvent for this purpose is hexane, octane, decane, cyclohexane or a similar aliphatic hydrocarbon; benzene, toluene, xylene or a similar aromatic hydrocarbon; diethyl ether, dibutyl ether, tetrahydrofuran, dioxane or similar ethers; acetone, methyl ethyl ketone, methyl isobutyl ketone, diisobutyl ketone or similar ketones; methyl acetate, ethyl acetate, butyl acetate, isobutyl acetate or similar esters; methanol, ethanol, isopropanol, butanol or similar alcohols; octamethylcyclotetrasiloxane, decamethylcyclopentasiloxane, hexamethyldisiloxane, octamethyltrisiloxane or a similar organosiloxane oligomer.

A radical initiator may be any compound known in the art for standard free-radical polymerization reactions. The specific examples of such radical initiators are 2,2'-azobis(isobutyronitrile), 2,2'-azobis(2-methylbutyronitrile), 2,2'-azobis(2,4-dimethylvaleronitrile) or similar compounds of azobis type; benzoyl peroxide, lauroyl peroxide, tert-butyl peroxybenzoate, tert-butyl peroxy-2-ethylhexanoate or a similar organic peroxide. These radical initiators may be used alone or in a combination of two or more. The radical initiators may be used in an amount of from 0.1 to 5 parts by weight per 100 parts by weight of the components (A) and (B). A chain-transfer agent may be added. The chain-transfer agent may be 2-mercaptoethanol, butylmercaptan, n-dodecylmercaptan, 3-mercaptopropyltrimethoxysilane, a polydimethylsiloxane containing a mercaptopropyl group or a similar compound of mercapto type; methylene chloride, chloroform, carbon tetrachloride, butyl bromide, 3-chloropropyltrimethoxysilane, or a similar halogenated compound.

In the manufacture of the polymer of vinyl type, after the polymerization, the unreacted residual vinyl monomer may be removed under conditions of heating under vacuum.

To facilitate the preparation of the mixture of the starting material of cosmetic products, the number-average molecular weight of the vinyl polymer containing a carbosiloxane dendrimer may be chosen within the range between 3000 and 2 000 000 and preferably between 5000 and 800 000. It may be a liquid, a gum, a paste, a solid, a powder, or any other form. The preferred forms are solutions consisting of the dilution of a dispersion or of a powder in solvents.

The vinyl polymer may be a dispersion of a polymer of vinyl type having a carbosiloxane dendrimer structure in its molecular side chain, in a liquid such as a silicone oil, an organic oil, an alcohol or water.

The silicone oil may be a dimethylpolysiloxane having the two molecular ends capped with trimethylsiloxy groups, a copolymer of methylphenylsiloxane and of dimethylsiloxane having the two molecular ends capped with trimethylsiloxy groups, a copolymer of methyl-3,3,3-trifluoropropylsiloxane and of dimethylsiloxane having the two molecular ends capped with trimethylsiloxy groups, or similar unreactive linear silicone oils, and also hexamethylcyclotrisiloxane, octamethylcyclotetrasiloxane, decamethylcyclopentasiloxane, dodecamethylcyclohexasiloxane or a similar cyclic compound. In addition to the unreactive silicone oils, modified polysiloxanes containing functional groups such as silanol groups, amino groups and polyether groups on the ends or within the side molecular chains may be used.

The organic oils may be isododecane, liquid paraffin, isoparaffin, hexyl laurate, isopropyl myristate, myristyl myristate, cetyl myristate, 2-octyldodecyl myristate; isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil, almond oil, olive oil, cocoa oil, jojoba oil, gum oil, sunflower oil, soybean oil, *camellia* oil, squalane, castor oil, cottonseed oil, coconut oil, egg yolk oil, polypropylene glycol monooleate, neopentyl glycol 2-ethylhexanoate or a similar glycol ester oil; triglyceryl isostearate, the triglyceride of a fatty acid of coconut oil, or a similar oil of a polyhydric alcohol ester; polyoxyethylene lauryl ether, polyoxypropylene cetyl ether or a similar polyoxyalkylene ether.

The alcohol may be any type that is suitable for use in combination with a cosmetic product starting material. For example, it may be methanol, ethanol, butanol, isopropanol or similar lower alcohols.

A solution or a dispersion of the alcohol should have a viscosity within the range from 10 to $10^9$ mPa at 25° C. To improve the sensory use properties when used in a cosmetic product, the viscosity should be within the range from 100 to $5 \times 10^8$ mPa·s.

The solutions and dispersions may be readily prepared by mixing a vinyl polymer containing at least one carbosiloxane dendrimer-based unit with a silicone oil, an organic oil, an alcohol or water. The liquids may be present in the step of polymerization of a vinyl polymer containing at least one carbosiloxane dendrimer-based unit. In this case, the unreacted residual vinyl monomer should be completely removed by heat treatment of the solution or dispersion under atmospheric pressure or reduced pressure.

In the case of a dispersion, the dispersity of the polymer of vinyl type may be improved by adding a surfactant.

Such an agent may be hexylbenzenesulfonic acid, octylbenzenesulfonic acid, decylbenzenesulfonic acid, dodecylbenzenesulfonic acid, cetylbenzenesulfonic acid, myristylbenzenesulfonic acid or anionic surfactants of the sodium salts of these acids; octyltrimethylammonium hydroxide, dodecyltrimethylammonium hydroxide, hexadecyltrimethylammonium hydroxide, octyldimethylbenzylammonium hydroxide, decyldimethylbenzylammonium hydroxide, dioctadecyldimethylammonium hydroxide, beef tallowtrimethylammonium hydroxide, coconut oil-trimethylammonium hydroxide, or a similar cationic surfactant; a polyoxyalkylene alkyl ether, a polyoxyalkylenealkylphenol, a polyoxyalkylene alkyl ester, the sorbitol ester of polyoxyalkylene, polyethylene glycol, polypropylene glycol, an ethylene oxide additive of diethylene glycol trimethylnonanol, and nonionic surfactants of polyester type, and also mixtures.

In addition, the solvents and dispersions may be combined with iron oxide suitable for use with cosmetic products, or a similar pigment, and also zinc oxide, titanium oxide, silicon oxide, mica, talc or similar inorganic oxides in powder form. In the dispersion, a mean particle diameter of the polymer of vinyl type may be within a range of between 0.001 and 100 microns and preferably between 0.01 and 50 microns. The reason for this is that, outside the recommended range, a cosmetic product mixed with the emulsion will not have a nice enough feel on the skin or to the touch, nor sufficient spreading properties nor a pleasant feel.

A vinyl polymer contained in the dispersion or the solution may have a concentration within a range of between 0.1% and 95% by weight and preferably between 5% and 85% by weight. However, to facilitate the handling and the preparation of the mixture, the range should preferably be between 10% and 75% by weight.

According to one preferred mode, a vinyl polymer that is suitable for use in the invention may be one of the polymers described in the examples of patent application EP 0 963 751.

According to one preferred embodiment, a vinyl polymer grafted with a carbosiloxane dendrimer may be the product of polymerization of:
(A) from 0.1 to 99 parts by weight of one or more acrylate or methacrylate monomer(s); and (B) from 100 to 0.1 parts by weight of an acrylate or methacrylate monomer of a tris[tri(trimethylsiloxy)silylethyldimethylsiloxy]silylpropyl carbosiloxane dendrimer.

According to one embodiment, a vinyl polymer containing at least one carbosiloxane dendrimer-based unit may comprise a tris[tri(trimethylsiloxy)silylethyldimethylsiloxy]silylpropyl carbosiloxane dendrimer-based unit corresponding to one of the formulae:

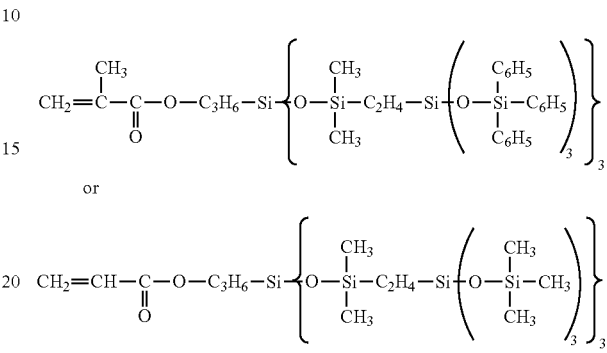

According to one preferred mode, a vinyl polymer containing at least one carbosiloxane dendrimer-based unit used in the invention comprises at least one butyl acrylate monomer.

According to one embodiment, a vinyl polymer may also comprise at least one fluoro organic group. A fluoro vinyl polymer may be one of the polymers described in the examples of patent application WO 03/045 337.

According to one preferred embodiment, a vinyl polymer grafted in the sense of the present invention may be conveyed in an oil or a mixture of oils, which is/are preferably volatile, chosen in particular from silicone oils and hydrocarbon-based oils, and mixtures thereof.

According to one particular embodiment, a silicone oil that is suitable for use in the invention may be cyclopentasiloxane.

According to another particular embodiment, a hydrocarbon-based oil that is suitable for use in the invention may be isododecane.

Vinyl polymers grafted with at least one carbosiloxane dendrimer-based unit that may be particularly suitable for use in the present invention are the polymers sold under the names TIB 4-100, TIB 4-101, TIB 4-120, TIB 4-130, TIB 4-200, FA 4002 ID (TIB 4-202), TIB 4-220 and FA 4001 CM (TIB 4-230) by the company Dow Corning. The polymers sold under the names FA 4002 ID (TIB 4-202) and FA 4001 CM (TIB 4-230) by the company Dow Corning will preferably be used.

Preferably, the vinyl polymer grafted with at least one carbosiloxane dendrimer-based unit that may be used in a composition of the invention is an acrylate/polytrimethylsiloxymethacrylate copolymer, in particular the product sold in isododecane under the name Dow Corning FA 4002 ID Silicone Acrylate by the company Dow Corning.

Silicone Acrylate Copolymers

According to one particular embodiment, a composition used according to the invention may comprise, as hydrophobic film-forming polymer, at least one copolymer comprising carboxylate groups and polydimethylsiloxane groups.

In the present patent application, the term "copolymer comprising carboxylate groups and polydimethylsiloxane groups" is intended to mean a copolymer obtained from (a)

one or more carboxylic (acid or ester) monomers, and (b) one or more polydimethylsiloxane (PDMS) chains.

In the present patent application, the term "carboxylic monomer" is intended to mean both carboxylic acid monomers and carboxylic acid ester monomers. Thus, the monomer (a) may be chosen, for example, from acrylic acid, methacrylic acid, maleic acid, fumaric acid, itaconic acid, crotonic acid, esters thereof and mixtures of these monomers. Esters that may be mentioned include the following monomers: acrylate, methacrylate, maleate, fumarate, itaconoate and/or crotonoate. According to one preferred embodiment of the invention, the monomers in ester form are more particularly chosen from linear or branched, preferably $C_1$-$C_{24}$ and better still $C_1$-$C_{22}$ alkyl acrylates and methacrylates, the alkyl radical preferentially being chosen from methyl, ethyl, stearyl, butyl and 2-ethylhexyl radicals, and mixtures thereof.

Thus, according to one particular embodiment of the invention, the copolymer comprises as carboxylate groups at least one group chosen from acrylic acid and methacrylic acid, and methyl, ethyl, stearyl, butyl or 2-ethylhexyl acrylates or methacrylates, and mixtures thereof.

In the present patent application, the term "polydimethylsiloxanes" (also known as organopolysiloxanes or abbreviated as PDMSs) is intended to denote, in accordance with what is generally accepted, any organosilicon polymer or oligomer of linear structure, of variable molecular weight, obtained by polymerization and/or polycondensation of suitably functionalized silanes, and consisting essentially of a repetition of main units in which the silicon atoms are linked together via oxygen atoms (siloxane bond ≡Si—O—Si≡), comprising trimethyl radicals directly linked via a carbon atom to said silicon atoms. The PDMS chains that may be used to obtain the copolymer used according to the invention comprise at least one polymerizable radical group, preferably located on at least one of the ends of the chain, i.e. the PDMS may contain, for example, a polymerizable radical group on the two ends of the chain or one polymerizable radical group on one end of the chain and one trimethylsilyl end group on the other end of the chain. The radical-polymerizable group may in particular be an acrylic or methacrylic group, in particular a group $CH_2$=$CR_1$—CO—O—$R_2$, in which $R_1$ represents a hydrogen or a methyl group and $R_2$ represents —$CH_2$—, —$(CH_2)_n$— with n=3, 5, 8 or 10, —$CH_2$—CH($CH_3$)—$CH_2$—, $CH_2$—$CH_2$—O—$CH_2$—$CH_2$—, —$CH_2$—$CH_2$—O—$CH_2$—$CH_2$—CH($CH_3$)—$CH_2$—, —$CH_2$—$CH_2$—O—$CH_2$ $CH_2$—O—$CH_2$—$CH_2$—$CH_2$—.

The copolymers used in the composition of the invention are generally obtained according to the usual methods of polymerization and grafting, for example by free-radical polymerization (A) of a PDMS comprising at least one polymerizable radical group (for example on one of the ends of the chain or on both ends) and (B) of at least one carboxylic monomer, as described, for example, in documents U.S. Pat. Nos. 5,061,481 and 5,219,560.

The copolymers obtained generally have a molecular weight ranging from about 3000 to 200 000 and preferably from about 5000 to 100 000.

The copolymer used in the composition of the invention may be in its native form or in dispersed form in a solvent such as lower alcohols comprising from 2 to 8 carbon atoms, for instance isopropyl alcohol, or oils, for instance volatile silicone oils (for example cyclopentasiloxane).

As copolymers that may be used in the composition of the invention, mention may be made, for example, of copolymers of acrylic acid and of stearyl acrylate containing polydimethylsiloxane grafts, copolymers of stearyl methacrylate containing polydimethylsiloxane grafts, copolymers of acrylic acid and of stearyl methacrylate containing polydimethylsiloxane grafts, copolymers of methyl methacrylate, butyl methacrylate, 2-ethylhexyl acrylate and stearyl methacrylate containing polydimethylsiloxane grafts. As copolymers that may be used in the composition of the invention, mention may be made in particular of the copolymers sold by the company Shin-Etsu under the names KP-561 (CTFA name: acrylates/dimethicone), KP-541 in which the copolymer is dispersed at 60% by weight in isopropyl alcohol (CTFA name: acrylates/dimethicone and isopropyl alcohol), and KP-545 in which the copolymer is dispersed at 30% in cyclopentasiloxane (CTFA name: acrylates/dimethicone and cyclopentasiloxane). According to one preferred embodiment of the invention, KP561 is preferably used; this copolymer is not dispersed in a solvent, but is in waxy form, its melting point being about 30° C.

Mention may also be made of the grafted copolymer of polyacrylic acid and dimethylpolysiloxane dissolved in isododecane, sold by the company Shin-Etsu under the name KP-550.

Hydrocarbon-Based Block Copolymer which is Preferably Amorphous

The composition according to the invention preferably comprises at least one hydrocarbon-based block copolymer which is preferably amorphous, also called amorphous hydrocarbon-based block copolymer, preferably a block copolymer that is soluble or dispersible in the liquid fatty phase.

The hydrocarbon-based block copolymer may in particular be a diblock, triblock, multiblock, radial or star copolymer, or mixtures thereof.

Such hydrocarbon-based block copolymers are described in patent application US-A-2002/005562 and in U.S. Pat. No. 5,221,534.

The copolymer may contain at least one block whose glass transition temperature is preferably less than 20° C., preferably less than or equal to 0° C., preferably less than or equal to −20° C. and more preferably less than or equal to −40° C. The glass transition temperature of said block may be between −150° C. and 20° C. and in particular between 100° C. and 0° C.

The hydrocarbon-based block copolymer present in the composition according to the invention is preferably an amorphous copolymer formed by polymerization of an olefin. The olefin may in particular be an ethylenically unsaturated monomer.

Examples of olefins that may be mentioned include ethylenic carbide monomers, in particular containing one or two ethylenic unsaturations and containing from 2 to 5 carbon atoms, such as ethylene, propylene, butadiene, isoprene or pentadiene.

Advantageously, the hydrocarbon-based block copolymer is an amorphous block copolymer of styrene and of an olefin.

Block copolymers comprising at least one styrene block and at least one block comprising units chosen from butadiene, ethylene, propylene, butylene and isoprene or a mixture thereof are in particular preferred.

According to one preferred embodiment, the hydrocarbon-based block copolymer is hydrogenated to reduce the residual ethylenic unsaturations after the polymerization of the monomers.

In particular, the hydrocarbon-based block copolymer is an optionally hydrogenated copolymer, containing styrene blocks and ethylene/$C_3$-$C_4$ alkylene blocks.

Diblock copolymers, which are preferably hydrogenated, that may be mentioned include styrene-ethylene/propylene copolymers, styrene/ethylene-propylene copolymers, styrene-ethylene/isoprene copolymers, styrene-ethylene/butadiene copolymers and styrene-ethylene/butylene copolymers. Diblock polymers are in particular sold under the name Kraton® G1701E by the company Kraton Polymers.

Triblock copolymers, which are preferably hydrogenated, that may be mentioned include styrene-ethylene/propylene-styrene copolymers, styrene-ethylene/butadiene-styrene copolymers, styrene-ethylene/butylene-styrene copolymers, styrene-isoprene-styrene copolymers and styrene-butadiene-styrene copolymers. Triblock polymers are in particular sold under the names Kraton® G1650, Kraton® G1652, Kraton® D1101, Kraton® D1102 and Kraton® D1160 by the company Kraton Polymers.

According to one particular embodiment of the invention, it is in particular possible to use a mixture of a styrene-butylene/ethylene-styrene triblock copolymer and of a styrene-ethylene/butylene diblock copolymer, in particular those sold under the name Kraton® G1657M by the company Kraton Polymers.

According to one preferred embodiment of the present invention, the hydrophobic film-forming polymer(s) is (are) chosen from amorphous hydrocarbon-based block copolymer(s) chosen from a styrene-ethylene/butylene diblock copolymer, a styrene/ethylene-propylene diblock copolymer, a styrene-ethylene/isoprene diblock copolymer, a styrene-ethylene/propylene diblock copolymer, a styrene-ethylene/butylene-styrene triblock copolymer, and mixture(s) thereof, even more preferably from a styrene/ethylene-propylene diblock copolymer, a styrene-ethylene/butylene-styrene triblock copolymer, and a mixture thereof.

Preferably, a composition according to the invention comprises at least one hydrocarbon-based block copolymer; the hydrocarbon-based block copolymer(s) is (are) present in a (total) content greater than or equal to 0.1% by weight, in particular greater than or equal to 0.5% by weight relative to the total weight of the composition, preferably between 0.8% and 10% by weight relative to the total weight of the composition and better still between 1% and 8% by weight relative to the total weight of the composition.

Hydrocarbon-Based Resin

The composition according to the invention may comprise at least one hydrocarbon-based resin, advantageously in combination with at least one hydrocarbon-based block copolymer, which is preferably amorphous, as previously described.

The resin used in the composition according to the invention (also called tackifying resin) preferably has a number-average molecular weight of less than or equal to 10 000 g/mol, in particular ranging from 250 to 10 000 g/mol, preferably less than or equal to 5000 g/mol, in particular ranging from 250 to 5000 g/mol, better still less than or equal to 2000 g/mol, in particular ranging from 250 to 2000 g/mol and even better still less than or equal to 1000 g/mol, in particular ranging from 250 to 1000 g/mol.

The number-average molecular weights (Mn) are determined by gel permeation liquid chromatography (THF solvent, calibration curve established with linear polystyrene standards, refractometric detector).

The resin of the composition according to the invention is advantageously a tackifying resin. Such resins are described in particular in the Handbook of Pressure Sensitive Adhesive, edited by Donatas Satas, 3rd edition, 1989, pp. 609-619.

The hydrocarbon-based resins are chosen from low molecular weight polymers that may be classified, according to the type of monomer they comprise, as:

indene hydrocarbon-based resins, preferably such as resins derived from the polymerization in major proportion of an indene monomer and in minor proportion of a monomer chosen from styrene, methylindene and methylstyrene, and mixtures thereof. These resins may optionally be hydrogenated. These resins may have a molecular weight ranging from 290 to 1150 g/mol.

Examples of indene resins that may be mentioned include those sold under the reference Escorez 7105 by the company Exxon Chem., Nevchem 100 and Nevex 100 by the company Neville Chem., Norsolene 5105 by the company Sartomer, Picco 6100 by the company Hercules and Resinall by the company Resinall Corp., or the hydrogenated indene/methylstyrene/styrene copolymers sold under the name "Regalite" by the company Eastman Chemical, in particular Regalite R1100, Regalite R1090, Regalite R7100, Regalite R1010 Hydrocarbon Resin and Regalite R1125 Hydrocarbon Resin;

aliphatic pentanediene resins such as those derived from the majority polymerization of the 1,3-pentanediene (trans- or cis-piperylene) monomer and of minor monomers chosen from isoprene, butene, 2-methyl-2-butene, pentene and 1,4-pentanediene, and mixtures thereof. These resins may have a molecular weight ranging from 1000 to 2500 g/mol.

Such 1,3-pentanediene resins are sold, for example, under the references Piccotac 95 by the company Eastman Chemical, Escorez 1304 by the company Exxon Chemicals, Nevtac 100 by the company Neville Chem. or Wingtack 95 by the company Goodyear;

mixed resins of pentanediene and of indene, which are derived from the polymerization of a mixture of pentanediene and indene monomers such as those described above, for instance the resins sold under the reference Escorez 2101 by the company Exxon Chemicals., Nevpene 9500 by the company Neville Chem., Hercotac 1148 by the company Hercules., Norsolene A 100 by the company Sartomer, Wingtack 86, Wingtack Extra and Wingtack Plus by the company Goodyear;

diene resins of cyclopentanediene dimers such as those derived from the polymerization of first monomers chosen from indene and styrene, and of second monomers chosen from cyclopentanediene dimers such as dicyclopentanediene, methyldicyclopentanediene and other pentanediene dimers, and mixtures thereof. These resins generally have a molecular weight ranging from 500 to 800 g/mol, for instance those sold under the reference Betaprene BR 100 by the company Arizona Chemical Co., Neville LX-685-125 and Neville LX-1000 by the company Neville Chem., PiccodienE 2215 by the company Hercules, Petro-Rez 200 by the company Lawter or Resinall 760 by the company Resinall Corp.;

diene resins of isoprene dimers such as terpenic resins derived from the polymerization of at least one monomer chosen from α-pinene, β-pinene and limonene, and mixtures thereof. These resins can have a molecular weight ranging from 300 to 2000 g/mol. Such resins are sold, for example, under the names Piccolyte A115 and 5125 by the company Hercules or Zonarez 7100 or Zonatac 105 Lite by the company Arizona Chem;

hydrogenated $C_6$-$C_{20}$ polyolefins such as those sold under the names Eastotac H-142W, Eastotac H-142R, and Eastotac H-100W by the company Eastman Chemical Co.

According to one preferred embodiment, the hydrocarbon-based resin is chosen from indene hydrocarbon-based resins, in particular hydrogenated indene/methylstyrene/styrene copolymers, such as those sold under the name Regalite by the company Eastman Chemical, such as Regalite R1100, Regalite R1090, Regalite R7100, Regalite R1010 Hydrocarbon Resin and Regalite R1125 Hydrocarbon Resin.

The hydrocarbon-based resin may be present in the composition according to the invention in a content ranging from 0.1% to 10% by weight, relative to the total weight of the composition, preferably ranging from 0.5% to 8% by weight and more preferentially ranging from 1% to 5% by weight.

Preferably, the composition according to the invention comprises at least 1% by weight of hydrocarbon-based resin relative to the total weight of the composition.

Aqueous Phase

The composition according to the invention may comprise an aqueous phase.

This aqueous phase, when present, is used in an amount that is compatible with the pulverulent galenical form required according to the invention.

The aqueous phase may be a demineralized water or alternatively a floral water such as cornflower water and/or a mineral water such as Vittel water, Lucas water or La Roche Posay water and/or a spring water.

The aqueous phase can also comprise a polyol which is miscible with water at ambient temperature (25° C.) chosen in particular from polyols containing in particular from 2 to 20 carbon atoms, preferably containing from 2 to 10 carbon atoms and preferentially having from 2 to 6 carbon atoms, such as glycerol, propylene glycol, butylene glycol, pentylene glycol, hexylene glycol, dipropylene glycol or diethylene glycol; glycol ethers (in particular having from 3 to 16 carbon atoms), such as mono-, di- or tripropylene glycol ($C_1$-$C_4$)alkyl ethers, mono-, di- or triethylene glycol ($C_1$-$C_4$)alkyl ethers; and mixtures thereof.

The composition according to the invention may comprise a polyol that is water-miscible at ambient temperature. Such polyols may promote the moisturization of the surface of the skin on which the composition is applied.

In addition, the composition according to the invention may comprise a monoalcohol containing from 2 to 6 carbon atoms, such as ethanol or isopropanol.

A composition according to the invention advantageously comprises less than 5% by weight of aqueous phase, and in particular of water, relative to the total weight of the composition. Preferentially, a composition according to the invention is free of aqueous phase, and in particular free of water.

Adjuvants

The composition may comprise other ingredients (adjuvants) commonly used in cosmetics, such as preserving agents, cosmetic active agents, moisturizers, UV-screening agents, thickeners and fragrances.

Of course, those skilled in the art will take care to choose the optional adjuvant or adjuvants added to the composition according to the invention so that the advantageous properties intrinsically attached to the composition in accordance with the invention are not, or not substantially, detrimentally affected by the envisaged addition.

Process for Manufacture Via the "Wet Process"

In the description of this process which follows, the fatty phase refers to the oily phase, optionally comprising one or more film-forming polymer(s).

The cosmetic composition in accordance with the invention can preferably be obtained via the "wet process", is more preferentially obtained via the "wet process", and comprises the steps of:
  mixing the fatty phase, the pulverulent phase and at least one additional volatile solvent in order to prepare a suspension;
  forming the composition resulting therefrom, by pressing, preferably inclusively between 2 and 20 bar, better still between 2 and 20 bar and more preferentially between 2 and 10 bar;
  removing, preferably completely, the additional volatile solvent(s).

The additional volatile solvent is preferably organic, in particular a volatile hydrocarbon-based solvent such as isododecane.

The step of removing the additional volatile solvent(s) is advantageously carried out by suctioning.

The process used advantageously comprises an additional step of drying, for example in an oven, at a temperature for example of between 30° C. and 100° C.

The term "preferably completely" should be understood to mean that the volatile solvent is removed such that only traces may remain in the composition, being present in a content less than 1% by weight relative to the total weight of the composition, and is preferably free of said cosmetic composition resulting from this preparation process.

Preferably, the additional solvent content used is greater than 20 g per 100 g of composition prepared, and preferably is between 20 and 50 g per 100 g of composition prepared.

Preferably, the process used is distinct from the "semi-wet processes" in which a small amount of additional solvent is used, for example less than 10 g per 100 g of composition, not making it possible to form a suspension within the meaning of the present invention.

Preferably, the process used is distinct from processes in which the suspension is dried before being compacted. Thus, the process used is preferably distinct from processes in which the volatile solvent used is removed from the composition before pressing.

Mixing Step

In this step, the compounds of the fatty phase, the compounds of the pulverulent phase and the additional volatile solvent(s) are mixed so as to prepare a suspension or dispersion of pulverulent materials in the solvent.

Preferably, the pulverulent phase is milled by any appropriate means before being mixed with the fatty phase.

The mixing step may, for example, be carried out by means of an extruder, a Henschel mixer or any other appropriate means.

According to one particular embodiment, the compounds of the fatty phase and of the pulverulent phase are mixed so as to form a mixture, and one or more additional volatile solvent(s) is (are) then mixed with said fatty phase-pulverulent phase mixture.

According to another embodiment, the compounds of the fatty phase and the additional volatile solvent(s) are mixed so as to form a mixture, and the pulverulent phase is then mixed with said fatty phase-additional volatile solvent(s) mixture.

The oily phase, preferably more generally the fatty phase, and the pulverulent phase are present in a respective content such that the weight ratio of said oily phase, preferably more generally the fatty phase, to said pulverulent phase ranges from 20:18 to 50:50, preferably from 25:75 to 45:65, and more preferably from 30:70 to 40:60.

The additional volatile solvent(s) is (are) chosen from water, lower alcohols such as ethanol and isopropanol, ethers, fluorocarbons, linear or cyclic volatile silicone oils, and volatile hydrocarbon-based oils, preferably from volatile hydrocarbon-based oils.

If necessary, a degassing step can take place during the mixing step.

Forming Step

In this step, the suspension is formed in a container or case by pressing, optionally accompanied by a suctioning step.

Preferably, the container receiving the composition may have holes which are intended for removing the residual volatile solvent(s), but which prevent the composition from passing through.

The method for placing the fatty phase-pulverulent phase-additional volatile solvent(s) suspension in the container is not limited. This step can be carried out by pouring, top injection (via the top of the container) or else back-injection (via the bottom of the container).

The step of pressing the suspension in the container can be carried out by any means, and in particular by mechanical means such as a press, or plate, which has a flat surface, or is embossed (if effect desired at the surface of the composition), which comes into contact with the suspension for the purpose of tapping said composition.

The suctioning step may be carried out by reducing the pressure in the container, for example by applying a vacuum. The suctioning step can be repeated several times. If necessary, a vibration can be performed.

The pressing step and/or the suctioning step allow(s) at least partial, preferably total, removal of the additional volatile solvent(s) so as to solidify the composition.

Drying Step

In this step, the formed suspension can be dried in order to remove the residual additional volatile solvent(s). The temperature and the time of this drying will depend in particular on the nature of the additional volatile solvent(s) used. This drying step can thus, for example, be carried out at a temperature between 30° C. and 100° C. The required time can, for example, range from ½ h to 48 h.

Although the "wet process" manufacturing process is preferred and more advantageous for manufacturing a composition in accordance with the invention, a more conventional "dry process" manufacturing process can be carried out in order to prepare a formula in accordance with the present invention.

Assembly

According to another aspect, the invention also relates to a cosmetic assembly comprising:

i) a container delimiting one or more compartment(s), said container being closed by a closing member and optionally not being leaktight; and ii) a makeup and/or care composition in accordance with the invention placed inside said compartment(s).

The container can, for example, be in the form of a pot or a case.

The closing member can be in the form of a lid comprising a cap mounted so as to be able to move by translation or by pivoting relative to the container housing said makeup and/or care composition(s).

EXAMPLES

Several examples intended to illustrate the invention in a non-limiting manner will now be described.

Solid cosmetic compositions, in the form of pressed powders, of face powders according to the invention were prepared as follows, and then tested according to various, in particular sensory, cosmetic evaluation criteria.

Examples 1 to 9 of formulations prepared employ various examples of face powder using spherical fillers, alone or as a mixture, in equivalent or different contents, and are compared with an example comprising only lamellar fillers.

| | Ingredients with % content | Ex. 1 | Ex. 2 | Ex. 3 | Ex. 4 |
|---|---|---|---|---|---|
| P | Mica | q.s. for 100 | q.s. for 100 | q.s. for 100 | q.s. for 100 |
| | Talc | 18 | 18 | 18 | 20 |
| | Pigments | 8 | 8 | 8 | 8 |
| | Powder of hexamethylene/trimethylol hexyl lactone copolymer containing silica (Plastic Powder D 400) | 18 | — | — | — |
| | Crosslinked polydimethylsiloxane gum beads coated with silsesquioxane resin (KSP 101 from Shin Etsu) | — | 18 | — | — |
| | Perlite powder (Optimat 2550 OR from World Minerals) | — | — | 18 | — |
| | Methylsilsesquioxane resin microbeads (Tospearl 145 from Momentive Performance) | — | — | — | 18 |
| F | Styrene-ethylene/butylene-styrene block copolymer (Kraton G1657M) | 1 | 1 | 1 | 1 |
| | $C_{12}$-$C_{15}$ alkyl benzoate (Tegosoft TN from Evonik Goldschmidt) | 26 | 26 | 26 | 26 |
| | Phenyltrimethylsiloxytrisiloxane (DC556 from Dow Corning) | 12 | 12 | 12 | 12 |

| | Preserving system | 0.5 | 0.5 | 0.5 | 0.5 | | |
|---|---|---|---|---|---|---|---|
| | Ingredients with % content | Ex. 5 | Ex. 6 | Ex. 7 | Ex. 8 | Ex. 9 | Ex. 10 |
| P | Mica | q.s. for 100 | q.s. for 100 | q.s. for 100 | q.s. for 100 | q.s. for 100 | q.s. for 100 |
| | Talc | 18 | 0 | 3 | 1 | 13 | 18 |
| | Pigments | 8 | 8 | 8 | 8 | 8 | 8 |
| | Crosslinked PMMA hemisphere (Microsphere M-310 from Matsumoto Yushi-Seiyaku) | 9.75 | 18.60 | 18.60 | 24.80 | 12.40 | — |
| | Nylon 12 powder (Orgasol 2002 EXD NAT COS from Arkema) | 4.55 | 8.70 | 8.70 | 11.60 | 5.80 | — |
| | Acrylate/ethylhexyl acrylate powder (Techpolymer ACP-8C from Sekisui Plastics) | 4.55 | 8.70 | 8.70 | 11.60 | 5.80 | — |
| F | Styrene-ethylene/butylene-styrene block copolymer (Kraton G1657M) | 1 | 1 | 1 | 1 | 1 | 1 |
| | $C_{12}$-$C_{15}$ alkyl benzoate (Tegosoft TN from Evonik Goldschmidt) | 26 | 26 | 26 | 26 | 26 | 26 |
| | Phenyltrimethylsiloxytrisiloxane (DC556 from Dow Corning) | 12 | 12 | 12 | 12 | 12 | 12 |
| | Preserving system | 0.5 | 0.5 | 0.5 | 0.5 | 0.5 | 0.5 |

The procedure below was used to prepare the compositions according to the invention.

1—Preparation of Phase P:

The compounds of phase P (pulverulent phase) are weighed out and then dispersed in a Novamix 1 L mixer-disperser for 3 minutes 30 seconds with paddle stirring at 3000 rpm and decaking at 2700 rpm. The nacres are then introduced into the mixer and dispersed for 3 minutes with paddle stirring at 3000 rpm.

2—Preparation of Phase F:

The compounds of phase F (fatty phase) are weighed out in a heating pan and then heated to 95° C., and homogenization is performed with stirring, using a deflocculator (Turbotest 33/300 PH—Rayneri, VMI Group). Once the mixture is homogeneous, it is cooled to 55° C. for the introduction of the compound of the preserving system.

3—Finalization of the Formula:

Phases P and F are brought together in a Kenwood Chef KM010 blender, with stirring, and then an organic volatile solvent such as isododecane is introduced according to a ratio such that at least 20 g of isododecane are added per 100 g of composition prepared. The mixture is then homogenized for approximately 2 minutes.

The preparation obtained is then pressed manually in a crucible. The isododecane rises by capillarity and is absorbed in a cloth.

A Nanyo machine can be used to carry out this preparation and in particular the pressing step optionally with suctioning.

According to an optional step, the composition may be heated by being placed in an oven or a furnace at a temperature of between 30° C. and 80° C. in order to accelerate or improve this step of removing the organic volatile solvent, for example at 45° C.

Evaluation of the Sensoriality

Evaluation Protocol:

An evaluation protocol was performed on a panel of 10 experienced individuals, with the result concerning:

the texture of the powder, the sensoriality and in particular the softness to the touch, the creaminess, the glide on uptake, the application (amount taken up, ease of application, adherence on application), the makeup result: uniformity, powdery effect, coverage, colour effect, mattness, comfort over the course of a day, wear property and ease of makeup removal of a composition according to the invention, evaluated by these same individuals.

Results

The tester panel brought to the fore in particular the aspect of a texture between a foundation and powder, more particularly the light texture in particular during disintegration and application, the ease of application, the absence of marks during application, the uniformity of the deposit, the matifying effect, the reduction of imperfections, the good wear property through the course of the day, the sensation of comfort the softness conferred on the skin, and a natural effect.

For formula 10 devoid of spherical filler(s), it exhibits in particular less glide on disintegration, and is rougher, drier and less comfortable, and confers less softness on the skin.

Measurement of the Impact Resistance

Measurement Principle

The machine used to perform such a measurement, known as a Package Drop-Test machine sold by the company Co Pack (Italy), makes it possible to perform drop tests on the solid compositions in compact powder form to measure their impact resistance. The drop height is 30 cm. By means of a small ruler, the size of the support that holds the compact is set (according to the size of the crucible) and the compact is then dropped by means of compressed air that actuates the aperture of the support.

This machine replaces the manual drop tests performed previously by the formulator using a 30 cm ruler. In this new manner, they are repeatable and thus more reliable. These drop tests show good resistance of the face powders, with a measured drop value greater than or equal to 1, in particular strictly greater than 1, and especially between 2 and 5 (no significant cracks or demoulding).

It is understood that, in the context of the present invention, the weight percentages given for a compound or a family of compounds are always expressed as weight of dry matter of the compound in question.

Throughout the patent application, the term "between" should be understood to mean "inclusively between", unless otherwise specified.

Throughout the patent application, the term "comprises one" or "includes one" should be understood to mean "comprising at least one" or "including at least one", unless otherwise specified.

The invention claimed is:

1. A solid cosmetic composition, comprising, in a physiologically acceptable medium:
   an oily phase greater than or equal to 30% by weight relative to a total weight of the composition, wherein the oily phase comprises a non-volatile oil in an amount of at least 30% by weight relative to the total weight of the composition,
   a pulverulent phase greater than or equal to 40% by weight relative to the total weight of the composition and comprising a spherical filler and a lamellar filler, and
   a hydrophobic film-forming polymer as the only film former in the solid cosmetic composition, wherein the hydrophobic film forming polymer is selected from the group consisting of a styrene-ethylene/butylene diblock copolymer, a styrene/ethylene-propylene diblock copolymer, a styrene-ethylene/isoprene diblock copolymer, a styrene-ethylene/propylene diblock copolymer, a styrene-ethylene/butylene-styrene triblock copolymer, and a mixture thereof
   wherein
   a content of the spherical filler is at least 10% by weight relative to the total weight of the composition,
   a sebum uptake of the spherical filler is at least 10 ml/100 g determined by measuring the amount of sebum adsorbed on to available surfaces of the spherical filler by measuring the wet point, and
   a weight ratio of the spherical filler to the lamellar filler is between 0.35 and 15,
   the solid composition is a pressed powder,
   the solid cosmetic composition is obtained by a process comprising:
   mixing the oily phase, the hydrophobic film-forming polymer, the pulverulent phase, and at least one additional volatile solvent to produce a suspension,
   subsequently pressing the suspension, and
   completely removing the at least one volatile solvent by suctioning.

2. The composition according to claim 1, wherein the pulverulent phase is present in a content of greater than or equal to 50% by weight, relative to the total weight of the composition.

3. The composition according to claim 1, wherein the spherical filler is selected from the group consisting of:
   silica powders;
   powders of acrylic polymer, copolymer, or a derivative thereof;
   polyurethane powders;
   silicone powders;
   polyamide powders;
   perlite powders;
   and any mixture thereof.

4. The composition according to claim 1, wherein the spherical filler is present in a total content of from 10 to 70% by weight, relative to the total weight of the composition.

5. The composition according to claim 1, wherein the lamellar filler is present in a total content greater than or equal to 1% by weight, relative to the total weight of the composition.

6. The composition according to claim 1, wherein the spherical filler and the lamellar filler are present in a total content greater than or equal to 20% by weight, relative to the total weight of the composition.

7. The composition according to claim 1, wherein the pulverulent phase further comprises a colouring agent in a content greater than or equal to 1% by weight, relative to the total weight of the composition.

8. The composition according to claim 1, wherein the oily phase comprises a non-volatile hydrocarbon-based oil of at least one synthetic ester of oils of formula $R_1COOR_2$,
   where
   $R_1$ represents a residue of at least one linear or branched fatty acid comprising from 1 to 40 carbon atoms,
   $R_2$ represents a hydrocarbon-based chain comprising from 1 to 40 carbon atoms, and
   $R_1+R_2$ is greater than or equal to 10.

9. The composition according to claim 1, wherein the oily phase comprises a silicone oil.

10. The composition according to claim 1, wherein the oily phase comprises a hydrocarbon-based oil, and a silicone oil.

11. The composition according to claim 1, wherein a content of the hydrophobic film-forming polymer is greater than or equal to 0.1% by weight, relative to the total weight of the composition.

12. The composition according to claim 1, which is a face powder.

13. The composition according to claim 1, wherein the hydrophobic film forming polymer is a styrene-ethylene/butylene-styrene block copolymer.

14. A process for manufacturing the cosmetic composition of claim 1, the process comprising:
   mixing an oily phase at a content of greater than or equal to 30% by weight relative to a total weight of the composition, wherein the oily phase comprises a non-volatile oil in an amount of at least 30% by weight relative to the total weight of the composition, a pulverulent phase at a content of greater than or equal to 40% by weight, the hydrophobic film-forming polymer, and at least one additional volatile solvent,
   pressing to form the composition, and
   completely removing the additional volatile solvent by suctioning to form a pressed powder, wherein
   the pulverulent phase comprises a spherical filler and a lamellar filler, a content of the spherical filler is at least 10% by weight relative to the total weight of the composition,
   a sebum uptake of the spherical filler is at least 10 ml/100 g determined by measuring the amount of sebum adsorbed on to available surfaces of the spherical filler by measuring the wet point, and
   a weight ratio of the spherical filler to the lamellar filler is between 0.35 and 15.

15. A process for coating a face with the composition according to claim 1, the process comprising: applying the composition to the face.

* * * * *